United States Patent
Cole et al.

(10) Patent No.: US 7,431,727 B2
(45) Date of Patent: Oct. 7, 2008

(54) MAGNETIC COMPONENTS FOR USE IN FORMING ANASTOMOSES, CREATING PORTS IN VESSELS AND CLOSING OPENINGS IN TISSUE

(75) Inventors: David H. Cole, San Mateo, CA (US); Samuel T. Crews, Redwood City, CA (US); Michael L. Reo, Redwood City, CA (US); Dean F. Carson, Mountain View, CA (US); Keke J. Lepulu, Redwood City, CA (US); Darin C. Gittings, Sunnyvale, CA (US)

(73) Assignee: Medtronic, Inc., Minneapolis, MN (US)

( * ) Notice: Subject to any disclaimer, the term of this patent is extended or adjusted under 35 U.S.C. 154(b) by 452 days.

(21) Appl. No.: 10/774,345

(22) Filed: Feb. 6, 2004

(65) Prior Publication Data

US 2005/0021059 A1 Jan. 27, 2005

Related U.S. Application Data

(63) Continuation of application No. 09/638,805, filed on Aug. 12, 2000, now Pat. No. 6,719,768, which is a continuation-in-part of application No. 09/562,599, filed on Apr. 29, 2000, now Pat. No. 6,352,543.

(51) Int. Cl.
*A61B 17/08* (2006.01)
(52) U.S. Cl. .................................. 606/153
(58) Field of Classification Search ............... 606/153, 606/151, 213, 215–217; 128/898; 600/9, 600/12; 623/1.15, 1.36, 23.64, 23.66
See application file for complete search history.

(56) References Cited

U.S. PATENT DOCUMENTS

| | | |
|---|---|---|
| 2,953,970 A | 9/1960 | Maynard |
| 3,041,697 A | 7/1962 | Budreck |
| 3,254,650 A | 6/1966 | Collito |
| 3,254,651 A | 6/1966 | Collito |
| 3,372,443 A | 3/1968 | Daddona, Jr. |

(Continued)

FOREIGN PATENT DOCUMENTS

DE 29513195 12/1996

(Continued)

OTHER PUBLICATIONS

Esformes, et al., "Biological Effects of Magnetic Fields Generated With CoSm Magnets," pp. 81-87.

(Continued)

*Primary Examiner*—Julian W Woo
(74) *Attorney, Agent, or Firm*—Mike Jaro; Jeffrey J. Hohenshell

(57) ABSTRACT

Methods and devices for forming an anastomosis between hollow bodies utilize magnetic force to couple anastomotic securing components and connect the lumens of the hollow bodies. End-to-side, side-to-side and end-to-end anastomoses can be created without using suture or any other type of mechanical fasteners, although such attachment means may be used in practicing some aspects of the invention. The securing components have the ability to produce a magnetic field and may include materials or assemblies. A component may also be used to form a port into the lumen of a vessel, the component being attached to the vessel by mechanical and/or magnetic means. Magnetic components may include means for concentrating the magnetic flux between respective components to increase the attraction force, thereby enhancing the security of the anastomosis. Also, rather than form a port communicating with a lumen of a vessel or other cavity, the components may have an occlusion surface and be used to close an opening in tissue, e.g., an atrial septal defect.

13 Claims, 37 Drawing Sheets

U.S. PATENT DOCUMENTS

| | | | |
|---|---|---|---|
| 3,519,187 A | 7/1970 | Kapitanov et al. |
| 3,727,658 A | 4/1973 | Eldridge, Jr. |
| 3,774,615 A | 11/1973 | Lim et al. |
| 3,952,334 A | 4/1976 | Bokros et al. |
| 3,986,493 A | 10/1976 | Hendren, III |
| 4,118,806 A | 10/1978 | Porier et al. |
| 4,154,226 A | 5/1979 | Hennig et al. |
| 4,210,132 A | 7/1980 | Perlin |
| 4,217,664 A | 8/1980 | Faso |
| 4,258,705 A | 3/1981 | Sorensen et al. |
| 4,350,160 A | 9/1982 | Kolesvo et al. |
| 4,352,358 A | 10/1982 | Angelchik |
| 4,366,819 A | 1/1983 | Kaster |
| 4,368,736 A | 1/1983 | Kaster |
| 4,397,311 A | 8/1983 | Kanshin et al. |
| 4,503,568 A | 3/1985 | Madras |
| 4,523,592 A | 6/1985 | Daniel |
| 4,534,761 A | 8/1985 | Raible |
| 4,553,542 A | 11/1985 | Schenck |
| 4,577,631 A | 3/1986 | Kreamer |
| 4,593,693 A | 6/1986 | Schenck |
| 4,607,637 A | 8/1986 | Berggren et al. |
| 4,624,255 A | 11/1986 | Schenck et al. |
| 4,624,257 A | 11/1986 | Berggren et al. |
| 4,657,019 A | 4/1987 | Walsh et al. |
| 4,665,906 A | 5/1987 | Jervis |
| 4,679,546 A | 7/1987 | van Waalwijk van Doorn et al. |
| 4,721,109 A | 1/1988 | Healey |
| 4,747,407 A | 5/1988 | Liu et al. |
| 4,784,646 A | 11/1988 | Feingold |
| 4,809,713 A | 3/1989 | Grayzel |
| 4,837,114 A | 6/1989 | Hamada et al. |
| 4,861,330 A | 8/1989 | Voss |
| 4,889,120 A | 12/1989 | Gordon |
| 4,899,744 A | 2/1990 | Fujitsuka et al. |
| 4,904,256 A | 2/1990 | Yamaguchi |
| 4,907,591 A | 3/1990 | Vasconcellos et al. |
| 4,917,087 A | 4/1990 | Walsh |
| 4,917,090 A | 4/1990 | Berggren et al. |
| 4,917,091 A | 4/1990 | Berggren et al. |
| 4,917,778 A | 4/1990 | Takada et al. |
| 4,935,080 A | 6/1990 | Hassell et al. |
| 5,013,411 A | 5/1991 | Minowa et al. |
| 5,015,238 A | 5/1991 | Solomon et al. |
| 5,089,006 A | 2/1992 | Stiles |
| 5,119,983 A | 6/1992 | Green et al. |
| 5,156,619 A | 10/1992 | Ehrenfeld |
| 5,178,634 A | 1/1993 | Ramos Martinez |
| 5,192,289 A | 3/1993 | Jessen |
| 5,211,683 A | 5/1993 | Maginot |
| 5,217,474 A | 6/1993 | Zacca et al. |
| 5,234,447 A | 8/1993 | Kaster et al. |
| 5,250,060 A | 10/1993 | Carbo et al. |
| 5,275,891 A | 1/1994 | Tagaya et al. |
| 5,304,220 A | 4/1994 | Maginot |
| 5,314,468 A | 5/1994 | Ramos Martinez |
| 5,316,595 A | 5/1994 | Hamada et al. |
| 5,330,486 A | 7/1994 | Wilk |
| 5,336,233 A | 8/1994 | Chen |
| 5,366,462 A | 11/1994 | Kaster et al. |
| 5,395,311 A | 3/1995 | Andrews |
| 5,411,508 A | 5/1995 | Bessler et al. |
| 5,425,763 A | 6/1995 | Stemmann |
| 5,441,507 A | 8/1995 | Wilk |
| 5,443,497 A | 8/1995 | Venbrux |
| 5,456,712 A | 10/1995 | Maginot |
| 5,456,714 A | 10/1995 | Owen |
| 5,464,449 A | 11/1995 | Ryan et al. |
| 5,478,354 A | 12/1995 | Tovey et al. |
| 5,507,629 A | 4/1996 | Jarvik |
| 5,522,834 A | 6/1996 | Fonger et al. |
| 5,556,405 A | 9/1996 | Lary |
| 5,571,167 A | 11/1996 | Maginot |
| 5,595,562 A | 1/1997 | Grier |
| 5,611,689 A | 3/1997 | Stemmann |
| 5,626,601 A | 5/1997 | Gershony et al. |
| 5,643,340 A | 7/1997 | Nunokawa |
| 5,669,918 A | 9/1997 | Balazs et al. |
| 5,676,670 A | 10/1997 | Kim |
| 5,681,260 A | 10/1997 | Ueda et al. |
| 5,690,656 A | 11/1997 | Cope et al. |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,380 A | 1/1998 | Hinchliffe et al. |
| 5,725,544 A | 3/1998 | Rygaard |
| 5,725,553 A | 3/1998 | Moenning |
| 5,758,663 A | 6/1998 | Wilk et al. |
| 5,797,920 A | 8/1998 | Kim |
| 5,817,113 A | 10/1998 | Gifford, III et al. |
| 5,830,224 A | 11/1998 | Cohn et al. |
| 5,868,763 A * | 2/1999 | Spence et al. ............... 606/153 |
| 5,895,404 A | 4/1999 | Ruiz |
| 5,904,147 A | 5/1999 | Conlan et al. |
| 5,906,579 A | 5/1999 | Vander Salm et al. |
| 5,916,226 A | 6/1999 | Tozzi |
| 5,968,089 A | 10/1999 | Krajicek |
| 5,997,467 A | 12/1999 | Connolly |
| 6,068,637 A | 5/2000 | Popov et al. |
| 6,074,416 A | 6/2000 | Berg et al. |
| 6,099,542 A | 8/2000 | Cohn et al. |
| 6,113,612 A * | 9/2000 | Swanson et al. ............ 623/1.15 |
| 6,152,937 A * | 11/2000 | Peterson et al. ............. 606/153 |
| 6,173,715 B1 | 1/2001 | Sinanan et al. |
| 6,179,849 B1 | 1/2001 | Yencho et al. |
| 6,187,020 B1 | 2/2001 | Zegdi et al. |
| 6,190,353 B1 | 2/2001 | Makower et al. |
| 6,206,913 B1 | 3/2001 | Yencho et al. |
| 6,241,743 B1 | 6/2001 | Levin et al. |
| 6,293,955 B1 | 9/2001 | Houser et al. |
| 6,296,604 B1 | 10/2001 | Garibaldi et al. |
| 6,352,543 B1 | 3/2002 | Cole |
| 6,419,681 B1 | 7/2002 | Vargas et al. |
| 6,428,550 B1 | 8/2002 | Vargas et al. |
| 6,491,705 B2 | 12/2002 | Gifford et al. |
| 6,558,400 B2 | 5/2003 | Deem et al. |
| 6,565,581 B1 * | 5/2003 | Spence et al. ............... 606/153 |
| 6,575,168 B2 | 6/2003 | LaFontaine et al. |
| 6,579,311 B1 | 6/2003 | Makower |
| 6,616,675 B1 | 9/2003 | Evard et al. |
| 6,632,229 B1 | 10/2003 | Yamanouchi |
| 6,652,540 B1 | 11/2003 | Cole et al. |
| 6,719,768 B1 | 4/2004 | Cole et al. |
| 6,802,847 B1 | 10/2004 | Carson et al. |
| 6,932,827 B2 | 8/2005 | Cole |
| 7,214,234 B2 | 5/2007 | Rapacki et al. |
| 7,232,449 B2 | 6/2007 | Sharkawy et al. |
| 7,241,300 B2 | 7/2007 | Sharkawy et al. |
| 2002/0143347 A1 | 10/2002 | Cole |
| 2002/0193782 A1 | 12/2002 | Ellis et al. |
| 2003/0014061 A1 | 1/2003 | Houser et al. |
| 2003/0014063 A1 | 1/2003 | Houser et al. |
| 2003/0065345 A1 | 4/2003 | Weadock |
| 2003/0167064 A1 | 9/2003 | Whayne |
| 2004/0215214 A1 | 10/2004 | Crews |
| 2005/0021059 A1 | 1/2005 | Cole |
| 2005/0080439 A1 | 4/2005 | Carson |
| 2005/0192603 A1 | 9/2005 | Cole |
| 2006/0161244 A1 | 7/2006 | Seguin |
| 2006/0282106 A1 | 12/2006 | Cole |
| 2007/0010834 A1 | 1/2007 | Sharkawy |

2007/0250084 A1  10/2007  Sharkawy

FOREIGN PATENT DOCUMENTS

| | | |
|---|---|---|
| DE | 29713335 | 7/1997 |
| FR | 2760627 | 9/1998 |
| RU | 2123300 | 12/1998 |
| SU | 736966 | 5/1980 |
| SU | 1025420 | 6/1983 |
| SU | 1179978 | 9/1985 |
| SU | 1438738 | 11/1988 |
| SU | 2018266 | 3/1989 |
| SU | 1537228 | 1/1990 |
| SU | 1595534 | 9/1990 |
| SU | 1629040 | 2/1991 |
| SU | 1635966 | 3/1991 |
| SU | 1277452 | 6/1991 |
| SU | 1708313 | 1/1992 |
| SU | 1361753 | 4/1992 |
| SU | 1725851 | 4/1992 |
| SU | 1766383 | 10/1992 |
| SU | 1969863 | 10/1992 |
| WO | 81/00668 | 3/1981 |
| WO | WO 81/00668 | 3/1981 |
| WO | WO 97/31578 | 2/1996 |
| WO | 97/31578 | 2/1997 |
| WO | WO 97/12555 | 4/1997 |
| WO | WO 97/13463 | 4/1997 |
| WO | WO 97/27897 | 8/1997 |
| WO | 98/40036 | 9/1998 |
| WO | WO 98/40036 | 9/1998 |
| WO | WO 99/40851 | 8/1999 |
| WO | WO 99/62415 | 12/1999 |
| WO | WO 99/63894 | 12/1999 |
| WO | WO 00/09040 | 2/2000 |
| WO | 00/24339 | 5/2000 |
| WO | WO 00/24339 | 5/2000 |
| WO | WO 00/27312 | 5/2000 |
| WO | WO 00/32241 | 6/2000 |
| WO | WO 00/33770 | 6/2000 |
| WO | WO 00/69364 | 11/2000 |
| WO | WO 00/74579 | 12/2000 |
| WO | WO 01/39672 | 6/2001 |
| WO | WO 01/82803 | 11/2001 |
| WO | WO 02/09594 | 2/2002 |
| WO | WO 02/19946 | 3/2002 |
| WO | WO 02/39878 | 5/2002 |
| WO | WO 02/094108 | 11/2002 |

OTHER PUBLICATIONS

Fuestel, et al., "Kontinente Kolostomie durch Magnetverschluβ," Dtsch. Med. Wschr. 100 (1975), pp. 1063-1064 (includes English Abstract).
Obora, et al., "Nonsuture Microvascular Anastomosis Using Magnet Rings: Preliminary Report," Surg. Neurol., vol. 9, Feb. 1978, pp. 117-120.
Kanshin, et al., "Sutureless anastomoses in gastrointestinal surgery with and without steady magnetic field," Arkh Patol, 1978; 40(8):56-61 (with English Abstract).
Pirusyan, et al., "Some Regularities of Tissue Squeezing and Regeneration Under Formation of "Unstitch" Anastomoses of the Alimentary Canal's Hollow Organs," 1979, pp. 13-17 (includes English abstract).
Obora, et al., "Nonsuture Microvascular Anastomosis using Magnet Rings," Jan. 16, 1980, pp. 497-505. (English translation is provided.)
Yanase, "An Experimental Study on Traumatic Changes in Microvessels Produced by Pressure Clamping," Aust N.Z. J. Surg. vol. 50-No. 4, Aug. 1980, pp. 423-428.
Jansen, et al., "Clinical Applications of Magnetic Rings in Colorectal Anastomosis," Surgery, Gynecology & Obstetrics, vol. 153, Oct. 1981, pp. 537-545.
Myshkin, et al., "Use of Permanent Magnets in Sutureless Anastomoses," 1987, pp. 47-52. (English translation is provided.).

Kanshin, et al., "A Goal-Oriented Local Approach to the Prevention of Postoperative Purulent Complications," 1991, pp. 24-27. (English abstract is provided.).
Stepanov, et al., "The treatment of intestinal fistulae in children by applying a by-pass anastomosis using magnetic devices," Khirugiia (Mosk), Nov.-Dec. 1992, pp. 11-12. (English abstract is provided.).
Fukumura, et al., "Development of a Magnetically Operated Artificial Urethral Sphincter," ASAIO Journal, 1993, pp. M283-M287.
Bondemark, et al., "Orthodontic Rare Earth Magnets—In Vitro Assessment of Cytotoxicity," British Journal of Orthodontia, vol. 21, No. 4, Nov. 1994, pp. 335-341.
Cope, "Evaluation of Compression of Cholecystogastric and Cholecystojejunal Anastomoses in Swine after Peroral and Surgical Introduction of Magnets," Journal of Vascular and Interventional Radiology, vol. 6, No. 4, Jul.-Aug. 1995, pp. 546-552.
Cope, "Creation of Compression Gastroenterostomy by Means of the Oral, Percutaneous, or Surgical Introduction of Magnets: Feasibility Study in Swine," Journal of Vascular and Interventional Radiology, vol. 6, No. 4, Jul.-Aug. 1995, pp. 539-545.
Bondemark, et al., "Long-term effects of orthodontic magnets on human buccal mucosa—a clinical, histological and immunohistochemical study," Eur J Orthod, 20(3): Jun. 1998, pp. 211-218.
Cope, "Stent Placement of Gastroenteric Anastomoses Formed by Magnetic Compression," Journal of Visceral Intervention, vol. 10, No. 10, Nov.-Dec. 1999, pp. 1379-1386.
Aharinejad S.H., et al., Microvascular Corrosion Casting in Scanning Electron Microscopy. Technique and Applications, Springer—Verlag/Wien, New York, pp. 12-23, 25, 28-39, 63-73, 75-81.
Ahn CY, Shaw WW, Berns S et al., "Clinical Experience With the 3M Microvascular Coupling Anastomotic Device in 100 Free-Tissue Transfer," Plastic and Reconstructive Surgery, Jun. 1994; 93(7):1481-84.
Angelini E, et al., "Corrosion under Static and Dynamic Conditions of Alloys Used for Magnetic Retention in Dentistry," J Prosthet Dent, 1991; 65:848-53.
ASM Metals Reference Book, Third Edition, Copyright 1993, p. 355.
Attai, et al., Aortic Valve Replacement in the Presence of Hufnagel Valve in the Descending Aorta, J. Thoracic Cardiovas. Surg., 1974, 68(1):112-115.
Attanasio SA, et al., "Corrosion of Rapidly Solidified Neodymion-Iron-Boron (Nd-Fe-B) Permanent Magnets and Protection via Sacrificial Zinc Coatings," Material Science and Engineering, 1995; A198:25-34.
Bala H, et al., "Effect of Impurities on the Corrosion Behavior of Neomydium," Journal of Applied Electrochemistry, 1993; 23(10):1017-1024.
Beppu, et al., A Computerized Control System for Cardiopulmonary Bypass, J. Thoracic Cardiovas. Surg., 1995, 109(3):428-438.
Bjork VO, Iert T, Landou C., "Angiographic changes in Internal Mammary Artery and Saphenous Vein Grafts, Two Weeks, One Year and Five Years After Coronary Bypass Surgery," Scand J Thor Cardiovasc Surg, 1981; 15:23-30.
Bornemisza G, Furka I., "Nonsuture Vascular Anastomosis," Acta Chirurgica Academiae Scientiarium Hungaricae, Tomus, 1971; 12(1):49-56.
Bourassa MG, Fisher LD, Campeau L, et al., "Long-Term Fate if Bypass Grafts: The Coronary Artery Surgery Study (CASS) and Montreal Heart Institute Experiences," Circ, Dec. 1985; 72(suppl V):71-77.
Brochure for "Neomax, Rare Earth Magnets," pp. 31-33, undated.
Buffolo E, de Andrade JCS, Branco JNR, et al., "Coronary Artery Bypass Grafting Without Cardiopulmonary Bypass," Ann Thorac Surg, 1996; 61:63-6.
Casanova R, Herrera GA, Vasconez EB, et al, "Microarterial Sutureless Sleeve Anastomosis Using a Polymeric Adhesive: An Experimental Study," J Reconstr Microsurg, Apr. 1987; 3(3):201-7.
Cha, et al., Silent Coronary Artery-Left Ventricular Fistula: A Disorder of the Thebesian System?, Angiology, 1978; 29(2):169-173.
Cheng CW, Cheng FT, Man HC, "Improvement of protective coatings on Nd-Fe-B magnet by pulse nickel plating," Journal of Applied Physics, Jun. 1, 1998; 83(11):6417-6419.

Cheng CW, et al., "Magnetic and Corrosion Characteristics of Nd-Fe-B Magnet with Various Surface Coatings," *IEEE Transactions on Magnetics*, 1997; 35(5):3910-3912 and CD-10.

Dake, et al., *Transluminal Placement of Endovascular Stent-Grafts for the Treatment of Descending Thoracic Aortic Aneurysms*, New England J. Med., 1994, 331(2):1729-1.

David JL, Limet R, "Antiplatelet Activity of Clopidogrel in Coronary Artery Bypass Graft Surgery Patients," *Thromb Haemost*, Nov. 1999; 82(5):417-21.

DeLacure MD, Kuriakose MA, Spies AL, "Clinical Experience in End-to-Side Venous Anastomosis With a Microvascular Anastomotic Coupling Device in Head and Neck Reconstruction," *Arch Otolaryngol Head Neck Surg*, Aug. 1999; 125:869-72.

Detweiler MB, Detweiler JG, Fenton J, et al., "Sutureless and Reduced Suture Anastomosis of Hollow Vessles with Fibrin Glue: A Review," *J Invest Surg*, Sep. 1999; 12(5):245-62.

Dormer KJ, Gan RZ, Santo R, "Middle Ear Titanium Transducer," *Society for Biomaterials*, Sixth World Biomaterials Congress Transactions; 2000: 1272.

Eckstein FS, Bonilla LF, Meyer B, et al., "Sutureless mechanical anastomosis of a saphenous vein graft to a coronary artery with a new connector device," *Lancet*, vol. 357, Mar. 24, 2001, pp. 931-932.

Endo K, et al., "Effects of Titanium Nitride Coatings on Surface and Corrosion Characteristics on Ni-Ti Alloy," *Dental Materials Journal*, 1994: 13(2):228-39.

Evans RD, et al., "Effect of Corrosion Products (neodymium Iron Boron) on Oral Fibroblast Proliferation," *J of Applied Biomater*, 1995; 6(3):199-202.

Frey RR, Bruschke AVG, Vermeulen FEE, "Serial Angiographic Evaluation 1 Year and 9 Years After Aorata-Coronary Bypass," *J Thorac Cardiovasc Surg*, 1984; 87(2):167-74.

Goldman S, Copeland J, Moritz T, et al., "Improvement in Early Saphenous Vein Graft Patency After Coronary Artery Bypass Surgery With Antiplatelet Therapy: Results of a Veterans Administration Cooperative Study," *Circulation*, Jun. 1988; 77(6):1324-32.

Goldman S, et al., "Starting aspirin therapy after operation—effects on early graft patency," *Circulation*, 1991; 84:520-526.

Goldman S, Zadina K, Krasnicka B, et al., "Predictors of Graft Patency 3 Years After Coronary Artery Bypass Graft Surgery," *J Am Coll Cardiol*, Jun. 1997; 29(7):1563-8.

Goy JJ, Kaufman U, Goy-Eggenberger D, et al., "A Prospective Randomized Trial Comparing Stenting to Internal Mammary Artery Grafting for Proximal, Isolated de novo Left Anterior Coronary Artery Stenosis: The SIMA Trial, *Stenting vs. Internal Mammary Artery,*" *Mayo Clin Proc*, Nov. 2000; 75(11):1116-23.

Grieb B, "New Corrosion Resistant Materials Based on Neodym-Iron-Boron," *Intermag Conference*, 1997; CD-08.

Group Arnold, The Magnetic Products Group of SPS Technologies, "Neodymium Magnets," Website: www.grouparnold.com, 4 pages (2008).

Gundry SR, Black K, Izuntani H, "Sutureless Coronary Artery Bypass with Biologic Glued Anastomosis: Preliminary In Vivo and In Vitro Results," *J Thorac Cardiovasc Surg*, Sep. 2000; 120(3):473-77.

Guyton RA, McClenathan JH, Michaelis LL, "A Mechanical Device for Sutureless Aorta-Saphenous Vein Anastomosis," *Ann Thorac Surg*, Oct. 1979; 28(4):342-5.

Heijmen RH, Borst C, van Dalen R, et al., "Temporary Luminal Arteriotomy Seal: II. Coronary Artery Bypass Grafting on the Beating Heart," *Ann Thorac Surg*, 1998; 66:471-6.

Heijmen RH, Hinchliffe P, Borst C, et al., "A Novel One-Shot Anastomotic Stapler Prototype for the Coronary Bypass Grafting on the Beating Heart: Feasibility on the Pig," *J Thorac and Cardiovasc Surg*, Jan. 1999; 117(1):117-25.

Ilia, R., *Coronary Angiography in Dextrocardia, Catheterization Cardio. Diag.*, 1991, 24 p. 150.

Jamieson, S.W., *Aortocoronary Saphenous Vein Bypass Grafting*, Operative Surgery, 4th Edition, pp. 454-470.

Kajiya, et al., *Mechanical Control of Coronary Arter Inflow and Vein Outflow*, Jap. Cir. J., 1989, 53:431-438.

Kitsugi A, et al., "The Corrosion Behavior of Nd2Fe14B and SmCo5 Magnets," *Dental Materials Journal*, 1992; 11(2):119-29.

Konerding MA, et al., "Scanning Electron Microscopy of Corrosion Casting in Medicine," *Scanning Microscopy*, 1991; 5(3):851-865.

Ku NC, et al., "Enhanced corrosion Resistance of NdFeB Type Permanent Magnet Coated by a Dual Layer of Either Ti/Al or Ni/Al Intermetallics," *IEEE Transactions on Magnetics*, 1997; 33(5):3913-5.

Ku NC, Qin C-D, Yu CC and Ng DHL, "Corrosion Reisstance of NdFeB magnets coated by Al," *IEEE Transactions on Magnetics*, Sep. 1996; 32(5):4407-4409.

Lamestschwandter A, et al., "Scanning Electron Microscopy of Vascular Corrosion Casts—Technique and Applications: Updated Review," *Scanning Microscopy*, 1990; 4(4):889-941.

Louagie, et al., *Operative Risk Assessment in Coronary Artery Bypass Surgery, 1990-1993: Evaluation of Perioperative Variables*, Thorac. Cardiovasc. Surg., 1995, 43:134-141.

Lytle BW, Loop FD, Cosgrove DM, et al., "Long-Term (5 to 12 Years) Serial Studies of Internal Mammary Artery and Saphenous Vein Coronary Bypass Grafts." *J Thorac and Cardiovasc Surg*, Feb. 1985; 89(2):248-58.

Magnet Sales and Manufacturing Company, Inc., "Neodymium Iron Boron," Website: www.magnetsales.com, 4 pages (2008).

Mattox DE, Wozniak JJ, "Sutureless Vascular Anastomosis with Biocompatible Heat-Shrink Tubing," *Arch Otolaryngol Head Neck Surg*, Nov. 1991; 117:1260-4.

Minowa T, Yoshikawa M, Honshima M, "Improvement of the corrosion resistance on Nd-Fe-B magnet with nickel plating," *IEEE Transactions on Magnetics*, Sep. 1989; 25(5):3776-3778.

Nataf P, Hinchliffe P, Manzo S, et al., "Facilitated Vascular Anastomoses: The One-Shot Device," *Ann Thorac Surg*, 1998; 66:1041-4.

Nataf P, Kirsch W, Hill AC, et al., "Nonpentrating Clips for Coronary Anastomosis," *Ann Thorac Surg*, 1997; 63:S135-7.

Noar JH, Whab A, Evans RD, Wojcik AG, "The durability of parylene coatings on neodymium-iron-boron magnets," *Eur J Orthod,*, Dec. 1999; 21(6):685-93.

Paz MA, Lupon J, Bosch X, et al., "Predictors of Early Saphenous Vein Aortocoronary Bypass Graft Occlusion. The GESIC Study Group," *Ann Thorac Surg*, Nov. 1993; 56(5):1101-6.

Pourbaix M, "Electrochemical Corrosion of Metallic Biomaterials," *Biomaterials*, 1984; 5:122-34.

Puskas JD, Wright CE, Ronson RS, et al., "Clinical Outcomes and Angiographic Patency in 125 Consecutive Off-Pump Coronary Bypass Patients," *The Heart Surgery Forum #999-95310*, May 1999; 2(3):216-21.

Reddy, et al., *Multiple Coronary Arteriosystemic Fistulas*, Amer. J. Cardiol., 1974, 33:304-306.

Riess, Friedrich-Christian, et al., "Clinical Experience with the CorLink Device for Proximal Anastomosis of the Saphenous Vein to the Aorata: A Clinical Prospective, and Randomized Study," *The Heart Surgery Forum*, #2002-71002, 5(4), 2002:345-353.

Rueland D, Schomacher PR, Mueller KM, et al., "Experimental Studies With a New Sutureless Anastomic Flange," *Trans AM Soc Artif Intern Organs*, 1979; 25:339-43.

Ryhanen J, et al., "Biocompatibility of Nickel-Titanium Shape Memory Metal and Its Corrosion Behavior in Human Cell Cultures," *JBMR*, 33 1997; 451-7.

Sanz G, Pajaron A, Algria E, et al., "Prevention of Early Aortocoronary Bypass Occlusion by Low-Dose Aspirin and Dipyridamole," *Circulation*, Sep. 1990; 82(3):765-73.

Sastri, et al., *Coronary Artery Left Ventricular Fistula*, Chest, 1975, 68(5):735-736.

Scheltes JS, Heikens M, Pistecky PV, et al., "Assessment of Patented Coronary End-to-Side Anastomotic Devices Using Micromechanical Bonding," *Ann Thorac Surg*, Jul. 2000; 70(1):218-21.

Segal, et al., *Alterations of Phasic Coronary Artery Flow Velocity in Humans During Percutaneous Coronary Angioplasty*, JACC, 1992, 20(2):276-286.

Seides SF, Borer JS, Kent KM, et al., "Long-Term Anatomic Fate of Coronary-Artery Bypass Grafts and Functional Status of Patients Five Years after Operation," *N Engl J Med*, 1978; 298(22):1213-17.

Senftle F, et al., "Electrolytic Corrosion of Gold and the Formation of Au2(SO4)3 in Concentrated Sulfuric Acid," *Journal of the Electrochemical Society*, 1985; 129-30.

Sethi GK, Copeland JG, Goldman S, et al., "Implications of Preoperative Administration of Aspirin in Patients Undergoing Coronary Artery Bypass Grafting. Department of Veterans Affairs Cooperative Study on Antiplatelet Therapy," *J Am Coll Cardiol*, Jan. 1990; 15(1):15-20.

Souza DSR, Bomfim V, Skoglund H, et al., "High Early Patency Saphenous Vein Graft for Coronary Artery Bypass Havested with Surrounding Tissue," *Ann Thorac Surg*, 2001; 71:797-800.

Stevens, et al., *Port-Access Coronary Artery Bypass Grafting: A Proposed Surgical Method*, J. Thorac. *J. Cardiovasc. Surg.*, 1996, 111(3):567-573.

Sugiura T., "Magnetic Compression Anastomosis of the Vascular System in Experimental Dog Models," 211, p. S141, 1 page English abstract and 12 page silde show.

Supplementary Partial European Search Report from European Patent Application No. 01959718.6 dated Jan. 7, 2005.

Takenaka H, Esato K, Ohara M, et al., "Sutureless Anastomosis of Blood Vessels Using Cyanoacrylate Adhesives," *Surg Today*, 1992; 22(1):46-54.

Thierry B, et al., "Effect of Surface Treatment and Sterilization Processes on the Corrosion Behavior of NiTi Shape Memory Alloy," *JBMR*, 51(4), 2000; 685-93.

von Segesser, L.K., *Arterial Grafting for Myocardial Revascularization*, 1990, pp. 3-140.

Weissberg D, Schwartz P, Goetz RH, Nonsuture End-to-Side Anastomoses of Small Blood Vessels, *Surgery, Gynecology & Obstetrics*, Aug. 1966; 341-46.

Werker P, Kon M, "Review of Facilitated approaches to Vascular Anastomosis Surgery," *Ann Thorac Surg*, 1997; 63:S122-7.

Whiffen JD, Boake WC, Gott VL, "Vessel Patency Following Nonsuture Anastomosis with Intravascular Rings," *Arch Surg*, Dec. 1965; 91(6):939-41.

Willman CJ, et al., "Corrosion Characteristics of RE-Fe-B Permanent Magnets," *J Appl Phys*, 1987; 61(8):3766-3768.

Yamagate S, Carter LP, Handa H, et al., "Experimental Studies in Nonsuture End-to-Side Microvascular Anastomosis," *Neurol Med Chiro (Tokyo)*, 1981; 21:701-08.

Zegdi R, Martinod E, Fabre O, et al., "Video-Assisted Replacement of Bypass Grafting of the Descending Thoracic Aorta With a New Sutureless Vascular Prostahesis: An Experimental Study," *J Vasc Surg*, 1999; 30:320-4.

\* cited by examiner

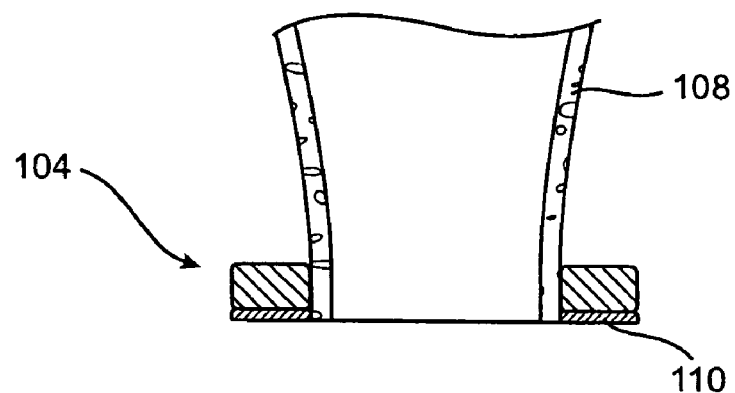
FIG. 10C
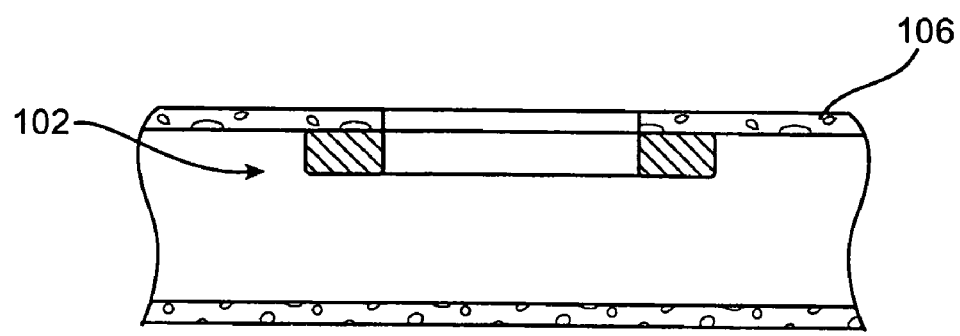
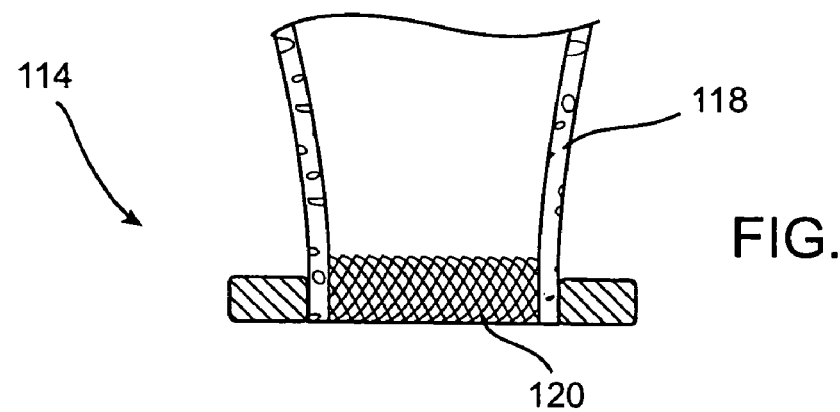
FIG. 10D
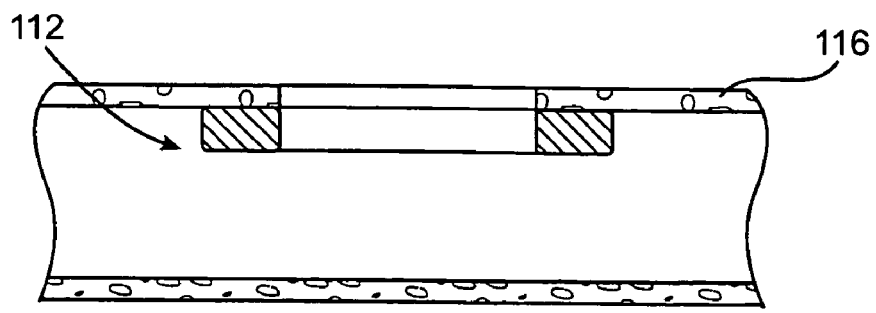

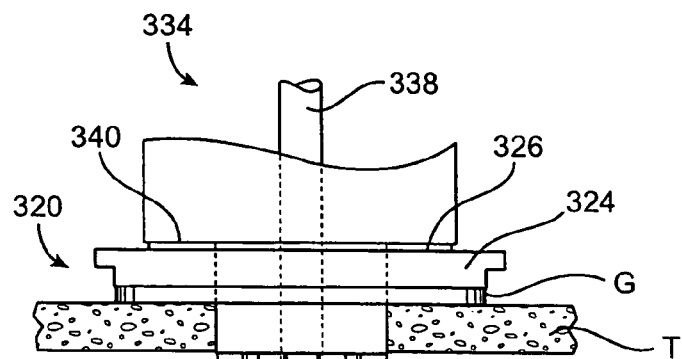
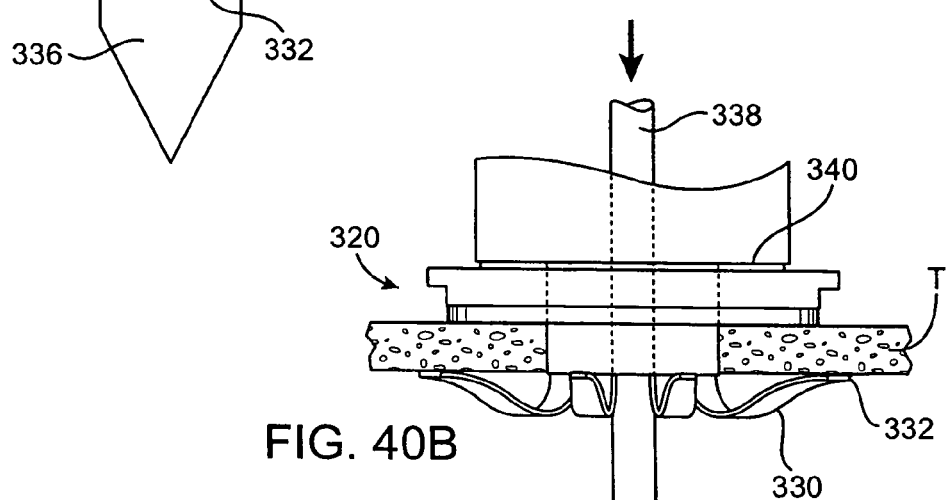
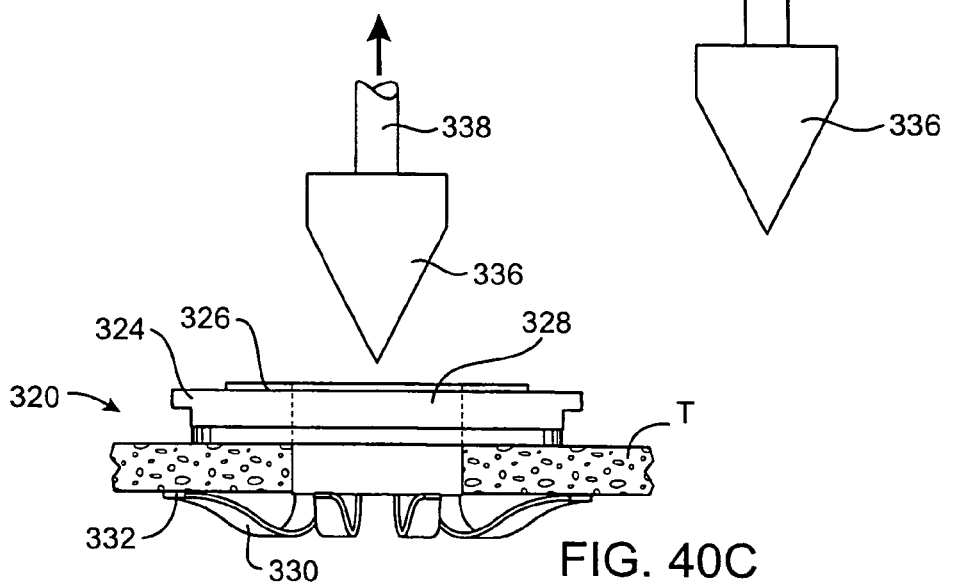
FIG. 40A
FIG. 40B
FIG. 40C

MAGNETIC COMPONENTS FOR USE IN FORMING ANASTOMOSES, CREATING PORTS IN VESSELS AND CLOSING OPENINGS IN TISSUE

CROSS-REFERENCE TO RELATED APPLICATIONS

This application is a continuation of U.S. application Ser. No. 09/638,805, filed on Aug. 12, 2000 now U.S. Pat. No. 6,719,768, which is a continuation-in-part of U.S. application Ser. No. 09/562,599, filed on Apr. 29, 2000, now U.S. Pat. No. 6,352,543, the entire disclosures of which are hereby incorporated by reference.

BACKGROUND OF THE INVENTION

1. Field of the Invention

The invention relates to methods and devices for forming anastomoses between two hollow bodies, creating magnetic ports in vessels, and closing openings in tissue, for example, atrial or ventricular septal defects.

2. Description of Related Art

Despite the considerable advances that have been realized in cardiology and cardiovascular surgery, heart disease remains the leading cause of death throughout much of the world. Coronary artery disease, or arteriosclerosis, is the single leading cause of death in the United States today. As a result, those in the cardiovascular field continue to search for new treatments and improvements to existing treatments.

Coronary artery disease is currently treated by interventional procedures such as percutaneous transluminal coronary angioplasty (PTCA), coronary stenting and atherectomy, as well as surgical procedures including coronary artery bypass grafting (CABG). The goal of these procedures is to reestablish or improve blood flow through occluded (or partially occluded) coronary arteries, and is accomplished, for example, by enlarging the blood flow lumen of the artery or forming a bypass that allows blood to circumvent the occlusion. What procedure(s) is used typically depends on the severity and location of the blockage. When successful, these procedures restore blood flow to myocardial tissue that had not been sufficiently perfused due to the occlusion.

Another proposed treatment places the target vessel, e.g., a coronary artery, in direct fluid communication with a heart chamber containing blood, for example, the left ventricle. Blood flows from the ventricle into a conduit that is in fluid communication with the artery; as such, this treatment may be described as a ventricular bypass procedure. Benefits of this procedure include obviating the need to manipulate the aorta, for example, as is done when a side-biting clamp is used in a typical CABG procedure to create a proximal anastomosis between the bypass graft and the aorta; Clamping or otherwise manipulating the aorta places the patient at risk in some cases due to the likelihood that such manipulation will release embolic material into the bloodstream. Some challenges associated with this procedure include delivering and deploying the conduit in the patient's body, properly positioning the conduit with respect to the heart chamber and the target vessel, and obtaining beneficial flow characteristics through the conduit and the target vessel.

A particularly challenging task that must be performed during CABG procedures (as well as some ventricular bypass procedures) is suturing the conduit to one or more vessels. As an example, one end of the conduit may be sutured to a source of blood, such as the aorta, a heart chamber or a blood vessel, while the other end of the conduit is sutured to the target vessel, such as a coronary artery or another blood vessel. The small diameter of the vessels involved (typically from 1 mm to 4 mm) makes creating a handsewn anastomosis a highly technical and time-consuming procedure. The difficulty in forming the sutured anastomosis is exacerbated when access to the target vessel is restricted or limited, as in a minimally invasive or percutaneous procedure. This problem also arises in non-cardiovascular applications that utilize handsewn anastomoses, for example, treating peripheral vascular disease or injury, creating AV (arteriovenous) shunts, etc.

While those in the art have proposed various anastomotic couplings intended to replace a sutured anastomosis, none has performed well enough to receive any significant level of acceptance in the field. Many of the proposed couplings penetrate or damage the target vessel wall acutely or chronically, do not remain patent, fail to produce a fluid-tight seal between the conduit and vessel, or are simply too cumbersome and difficult to deliver or deploy.

Accordingly, there is a need in the art for methods and devices for forming a reliable anastomosis between hollow bodies in a relatively quick, easy and repeatable manner, for creating a port in a vessel for use in forming the anastomosis, and for closing openings in tissue, either permanently or temporarily.

SUMMARY OF THE INVENTION

According to one embodiment the invention provides a device for forming a magnetic port in a hollow body having a lumen. The device includes a component capable of producing a magnetic field and having an opening configured to be placed in communication with the lumen of the hollow body, and a housing disposed on an exterior of the component. The housing provides a substantially sealed enclosure containing the component and is formed of a biocompatible material.

Another embodiment provides a device adapted to be coupled to tissue using magnetic force. The device includes a first securing component that is capable of producing a magnetic field and is adapted to attract a second securing component also capable of producing a magnetic field. A magnetic force-increasing mechanism is provided for increasing the magnetic force attracting the first and second securing components when they are positioned in proximity to each other.

Another embodiment provides a device adapted to be coupled to a blood vessel having a lumen so as to produce a magnetic field adjacent the blood vessel. The device includes at least one securing component that is sized and configured to be secured to a blood vessel having a lumen and is capable of producing a magnetic field. The securing component has an indicator that indicates the polarity of the magnetic field to a user carrying out a procedure on the blood vessel.

Another embodiment provides a device for forming a port in a first hollow body having a lumen. The device includes a securing component having an opening adapted to be placed in communication with an opening in the wall of the first hollow body e in communication with the lumen, and a mechanical attachment portion configured to secure the component to the first hollow body in a desired position. The securing component is configured to produce a magnetic field adjacent the opening in the first hollow body.

Another embodiment provides a delivery device in combination with a component for forming an anastomosis. The combination includes at least one component having an opening adapted to be placed in communication with a lumen of a vessel in a patient's body, the component being capable of producing a magnetic field, and a delivery device including a support portion supporting the component. The delivery device has a retaining portion that is movable with respect to the support portion and is placed in a first position to retain the component and moved from the first position to release the component. The retaining portion is movable with respect to the support portion in either an axial or rotary direction.

Another embodiment of the invention provides a method for increasing the magnetic force between first and second anastomotic securing components. The method is performed by providing first and second anastomotic securing components each of which is capable of producing a magnetic field, the first and second securing components having respective openings adapted to be placed in communication with each other, and increasing the magnetic force between the first and second securing components by concentrating magnetic flux therebetween.

According to another embodiment of the invention a method for coupling a securing component to a target vessel in order to form a magnetic port communicating with a lumen of the target vessel. This method is performed by providing at least one securing component capable of producing a magnetic field and having an opening adapted to be placed in communication with the lumen of the target vessel, coupling the one securing component to the target vessel with the opening in the one securing component communicating with the target vessel lumen, and, prior to completing the coupling step, confirming the orientation of the polarity of the magnetic field.

Another embodiment of the invention provides a method for forming a magnetic port in a first hollow body located within a patient, the first hollow body having a lumen. The method is carried out by forming an opening in a wall of the first hollow body, the opening extending into the lumen of the first hollow body, providing a first securing component capable of producing a magnetic field and having an opening adapted to be placed in communication with the opening in the wall of the first hollow body, and coupling the first securing component to the first hollow body by a mechanical attachment to form a magnetic port in the first hollow body.

BRIEF DESCRIPTION OF THE DRAWING FIGURES

Other features, aspects, benefits and advantages of the invention will be appreciated from the following detailed description of exemplary embodiments thereof taken in conjunction with the following Figures, wherein:

FIG. 10C is a section view similar to FIG. 10A but showing an alternative attachment between a hollow body and an anastomotic securing component;

FIG. 10D is a section view similar to FIG. 10C showing another alternative attachment between the hollow body and a securing component;

FIGS. 40A-40C are elevation views sequentially showing the device of FIGS. 36A-39C being deployed in a vessel having a lumen;

Figure 46A:
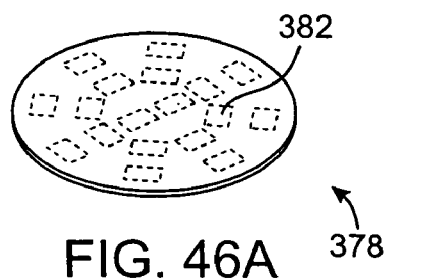
FIGS. 46A-46B shows alternative flexible magnetic components constructed according to additional embodiments of the invention.
Figure 46B:
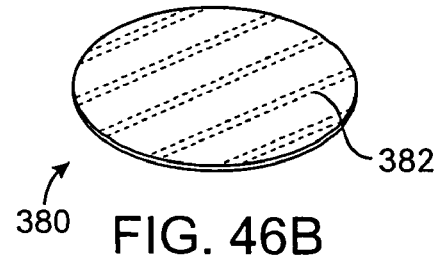
Figure 46C:
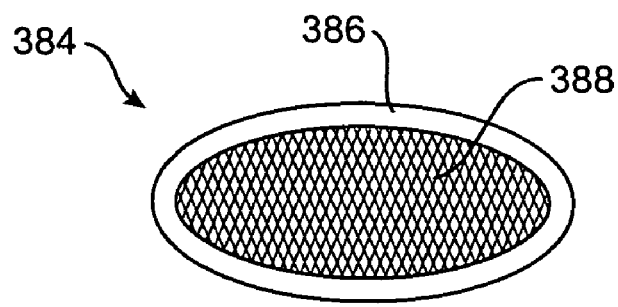
FIG. 46C is a perspective view of a flexible component with a magnetic core constructed according to yet another embodiment of the invention, the component being adapted to substantially or completely close an opening in tissue or another component.
Figure 46D:
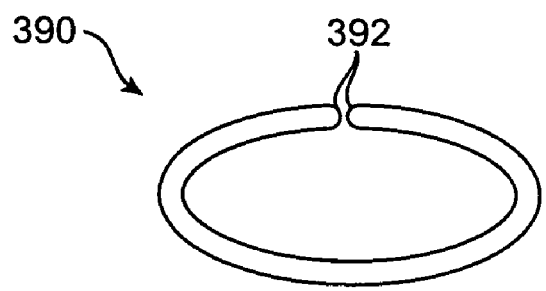
FIG. 46D is a perspective view of an alternative flexible magnetic component with a construction similar to the component of FIG. 46C but having an opening for placement in communication with the lumen of a vessel.
Figure 46E:
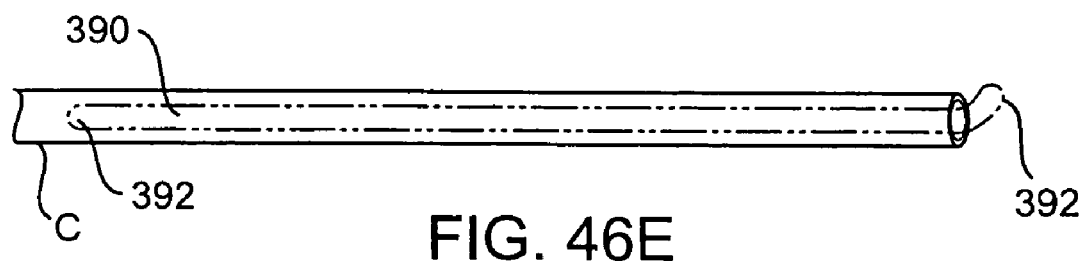
Figure 47A:
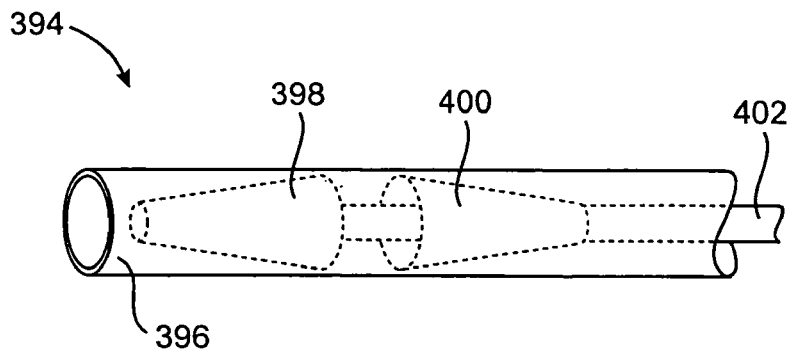
Figure 47B:
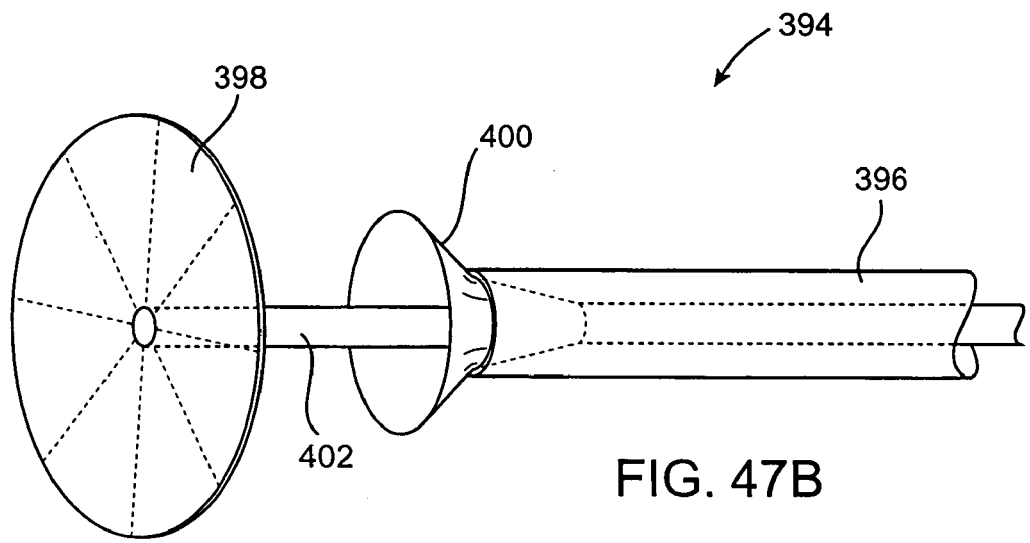
Figure 47C:
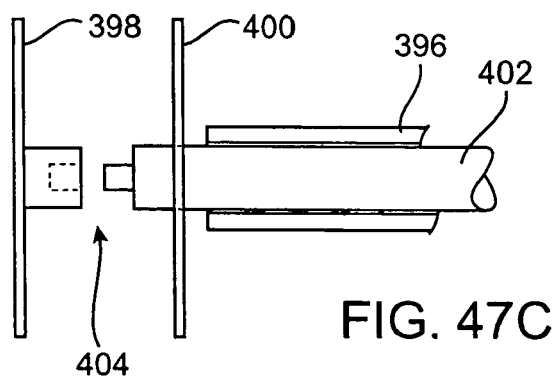
Figure 48A:
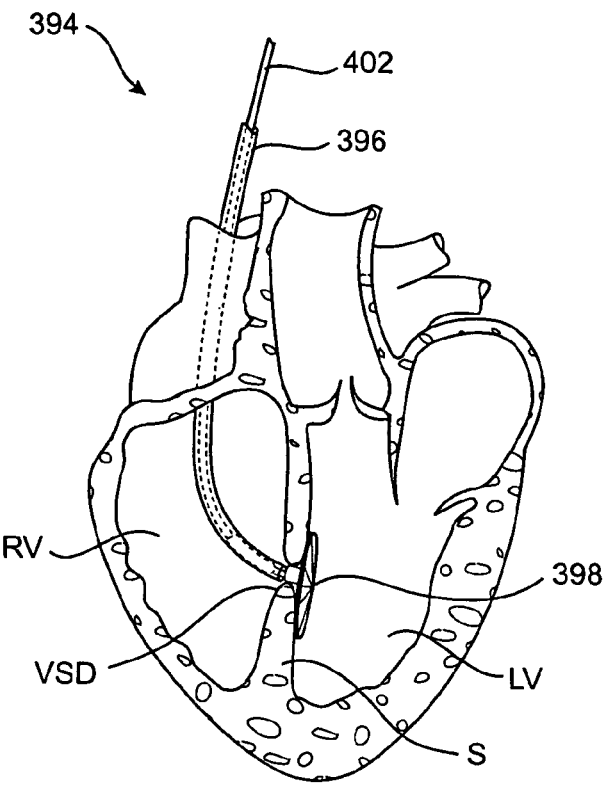
Figure 48B:
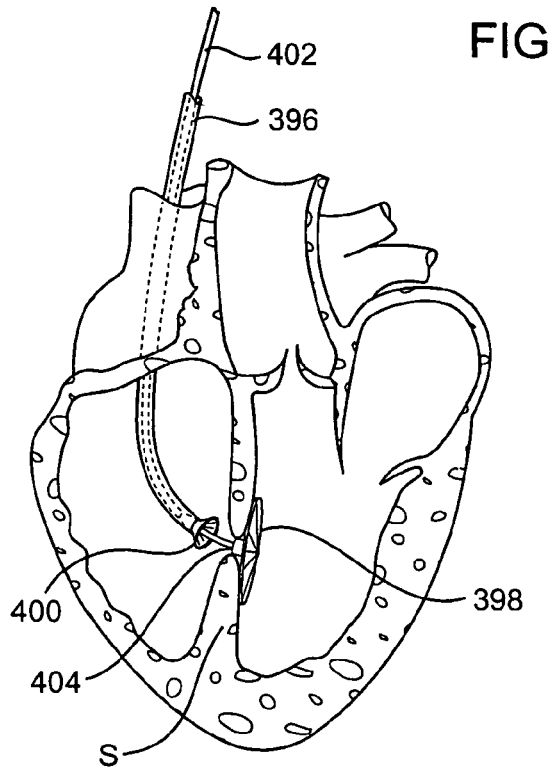
Figure 48C:
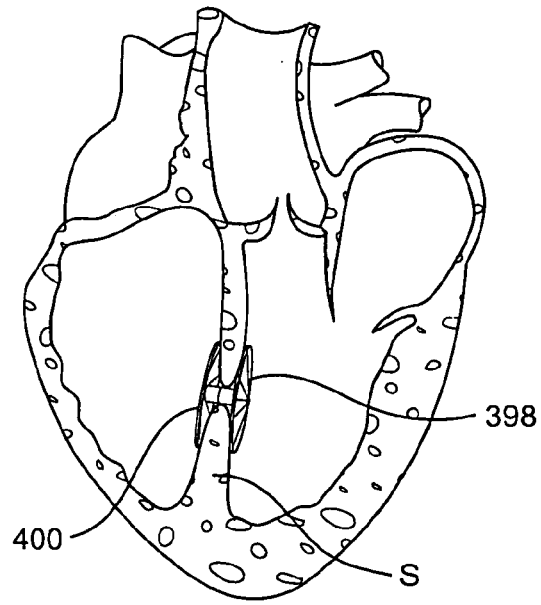

FIG. 46E schematically illustrates and exemplifies delivering the component shown in FIG. 46D in a low profile manner by way of a catheter or sheath;

FIGS. 47A-47B are perspective views showing a device constructed according to another embodiment of the invention for closing openings in tissue in a restrained position for delivery and a partially deployed position, respectively;

FIG. 47C is a fragmentary side elevation view of the device shown in FIGS. 47A-47B but with the device fully deployed; and FIGS. 48A-48C are elevation views sequentially showing the device of FIGS. 47A-47C being used to close a ventricular septal defect.

DETAILED DESCRIPTION OF THE DRAWING FIGURES

One aspect of the present invention relates to methods and devices for forming an anastomosis between first and second (or additional) hollow bodies located in a patient's body, for example, a connection between a graft vessel and coronary or peripheral blood vessels, viscera, reproductive ducts, etc. The anastomosis places the hollow bodies, more specifically the lumens of the hollow bodies, in communication. In the case of blood-carrying bodies (or other hollow bodies that carry fluid) the anastomosis places the bodies in fluid communication. The hollow bodies being joined may comprise native or autologous vessels, vessels formed of synthetic material such as ePTFE or DACRON®.

Figure 1:
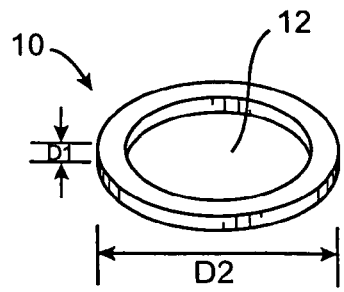
FIGS. 1-5 are perspective views of anastomotic securing components constructed according to various embodiments of the invention.

FIGS. 1-5 illustrate several exemplary embodiments of anastomotic securing components constructed according to the invention for use in forming an anastomosis between first and second hollow bodies. FIG. 1 shows a securing component 10 with an annular body and an opening 12 defined by the body. The component 10 is generally plate-shaped and circular in plan view with a constant (or substantially constant) thickness and width around its perimeter. The securing component 10 is sized and configured to be placed adjacent an opening of a first hollow body that has been prepared for anastomosis to a second hollow body. A second securing component would be placed adjacent an opening of the second hollow body for making the anastomotic connection.

Figure 2:
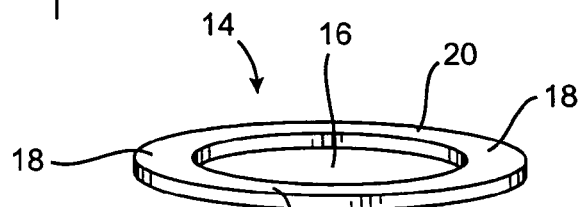
Figure 3:
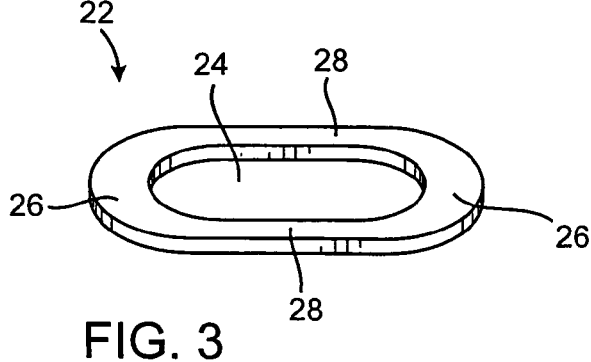
Figure 4:
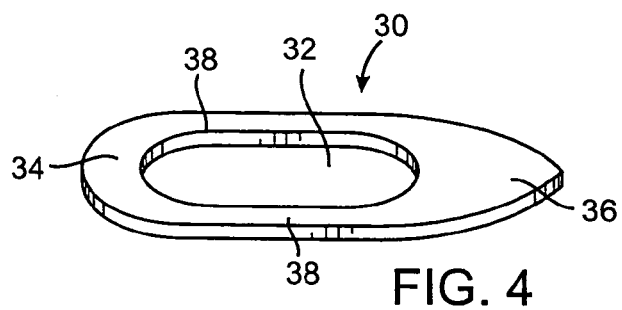

FIG. 2 shows an elliptically-shaped, anastomotic securing component 14 with an opening 16. The securing component 14 is generally plate-shaped and the opening 16 is configured to provide the securing component 14 with larger end portions 18 than side portions 20. FIG. 3 shows a racetrack-shaped securing component 22 with an opening 24. As in securing component 14, the opening 24 provides securing component 22 with larger end portions 26 than side portions 28. FIG. 4 shows a securing component 30 with an opening 32, two end portions 34, 36 and two side portions 38. The securing component 30 has a generally racetrack-shaped configuration, however, the end portion 36 is larger than the end portion 34 which provides the component 30 with an asymmetric configuration. Stated otherwise, the opening 32 is not centrally located with respect to the body of the component 30, unlike the openings 12, 16 and 24 of respective securing components 10, 14 and 22 shown in FIGS. 1-3. Also, the end 36 provides a tapered leading edge for easier introduction into a hollow body such as blood vessel.

It will be understood that the specific shape and size of the securing components may be varied from the exemplary configurations depicted in FIGS. 1-4. For example, the thickness or width of the securing component may vary along all or part of the body of the component. The anastomotic securing components of the invention are preferably, though not necessarily, plate-shaped, i.e., a first dimension D1 of the component is less than a second dimension D2 of the component (FIG. 1). Typically, the lesser dimension corresponds to a thickness of the component while the larger dimension corresponds to a width or length of the component (or diameter in the case of FIG. 1). Minimizing the thickness of the securing component may be desirable for applications in which one or more components are placed within the lumen of a relatively small hollow body, e.g., a coronary artery, to reduce the amount of foreign material in the bloodstream and minimize flow impedance.

It will be noted that the securing components shown in FIGS. 1-4 are generally flat; however, they could instead be curved or arcuate, or comprise a combination of flat and curved sections. Additionally, in the illustrated and preferred construction the shape of each securing component substantially corresponds to the opening therein. That is, the securing component and its opening preferably have complementary configurations (e.g., elliptical component, elliptical opening). Nevertheless, the securing component could have a non-complementarily-shaped opening. Finally, while each of the illustrated securing components includes only one opening, more than one opening could be used if desired.

According to preferred embodiments of the invention the anastomotic securing components are formed of or have incorporated therein a material capable of producing a magnetic field that acts to maintain the components in a desired positional relationship. The magnetic field results in the securing components maintaining the first and second hollow bodies in a desired position so as to be in fluid-tight communication. One or both securing components preferably has magnetic properties and may comprise permanent magnetic, ferro- or ferrimagnetic, or electromagnetic materials or assemblies.

Figure 5:
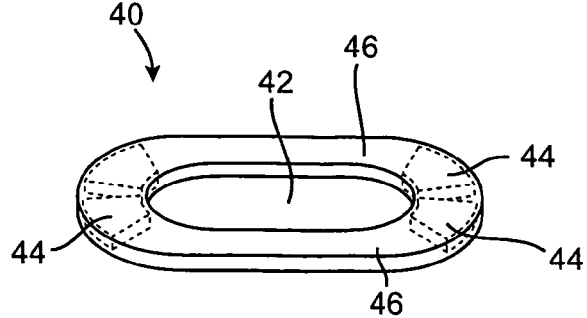

Each of the securing components shown in FIGS. 1-4 is formed substantially entirely of a suitable, magnetic field-producing material such that magnetic force may be generated over the entire area of the component. FIG. 5 shows an alternative embodiment wherein a securing component 40, which has an opening 42 and a racetrack-shaped configuration similar to securing component 22 of FIG. 3, has defined portions capable of producing a magnetic field. Specifically, the securing component 40 includes magnetic field-producing members 44 located at discrete areas which, in the illustrated embodiment, are at the ends of the component. The remaining areas 46 may thus be formed of a different material. It will be recognized that the members 44 could be located at alternative (or additional) areas of the securing component 40. An exemplary reason for providing the securing component 40 with areas 46 is to allow the use of a rigid magnetic material for the members 44 while still permitting the component to be partially or completely collapsed, for example, for delivery through a small incision or port, trocar, catheter, cannula, etc., by folding the areas 46.

Suitable materials that may be used to form an anastomotic securing component that is capable of producing a magnetic field include NdFeB (Neodymium Iron Boron), SmCo (Samarium Cobalt), and Alnico (Aluminum Nickel Cobalt). NdFeB is currently preferred for its force characteristics. The amount of force exerted will depend on various factors including the materials used, the size of the magnets and the number of magnets. In addition, different applications will call for different force ranges. For instance, it may be desirable to minimize the force as much as possible while still achieving a fluid-tight and secure attachment when treating small diameter blood vessels. As an example, in anastomosing coronary vessels, it is preferred to use anastomotic securing components that produce magnetic force in the area of less than 0.25 lbs, and more preferably approximately 0.15 lbs or less.

Figure 6:
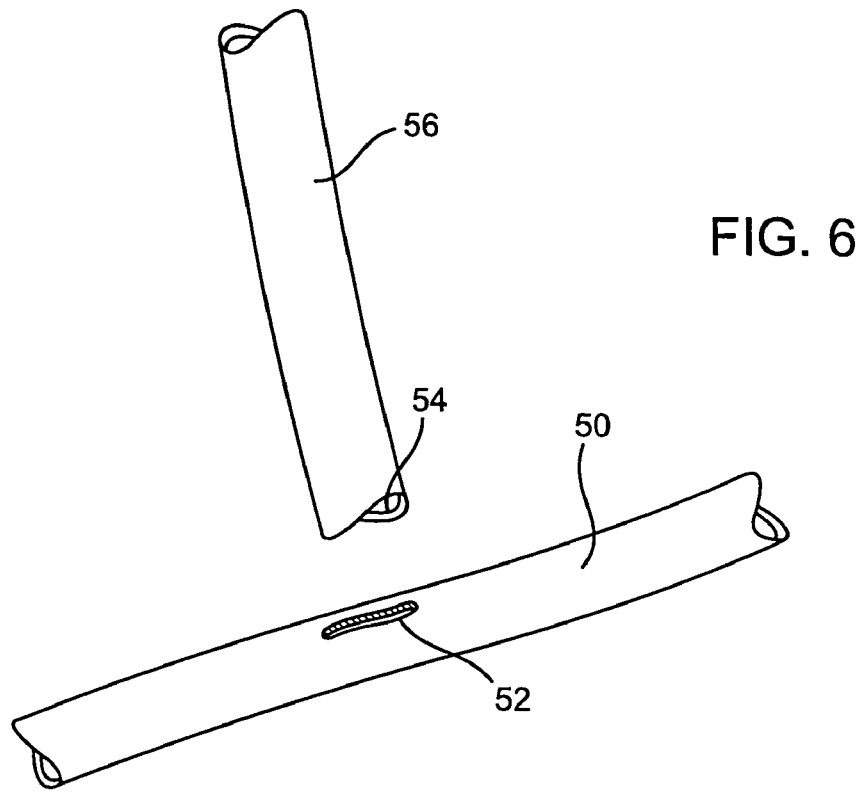
FIG. 6 is a perspective view showing two hollow bodies adapted to be joined in communication via an end-to-side anastomosis.
Figure 7:
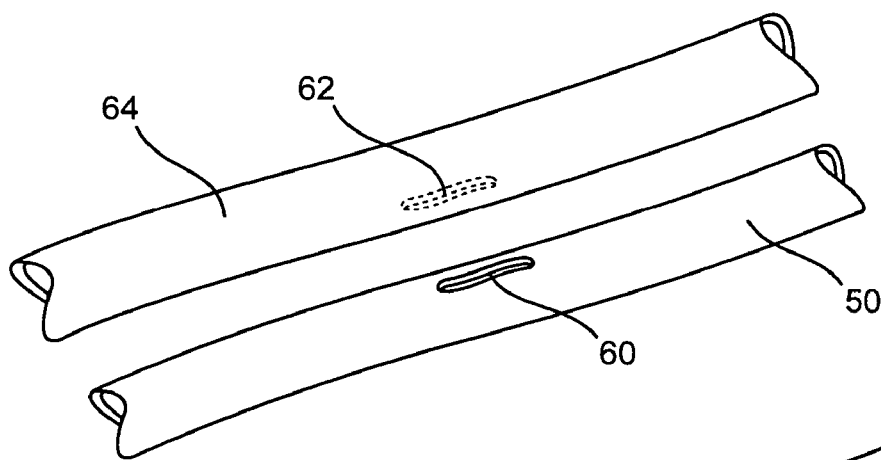
FIG. 7 is a perspective view showing two hollow bodies adapted to be joined in communication via a side-to-side anastomosis.
Figure 8:
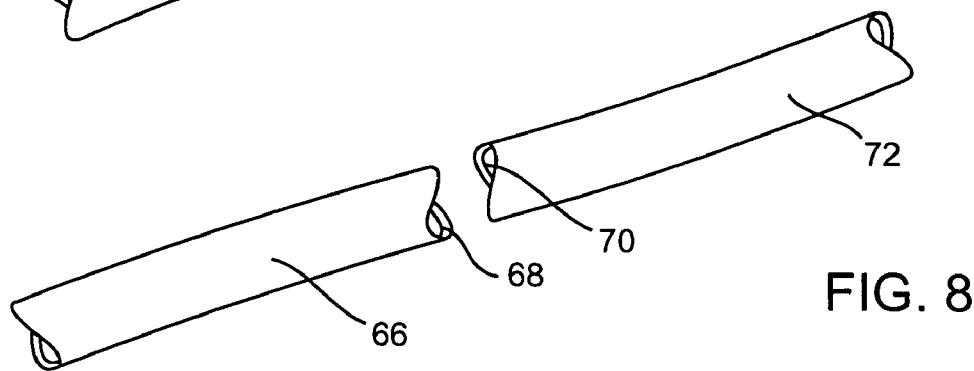
FIG. 8 is a perspective view showing two hollow bodies adapted to be joined in communication via an end-to-end anastomosis.

FIGS. 6-8 depict first and second hollow bodies that have been prepared for anastomosis in three different manners. FIG. 6 shows a first hollow body 50 with an opening 52 that is adapted to be joined to an opening 54 of a second hollow body 56 to form an end-to-side anastomosis. The completed anastomosis places the lumens of the respective hollow bodies in communication. The opening 52 is formed in the wall of the first hollow body 50, for example, by incising or punching the tissue of the wall, while the opening 54 is defined by an end of the second hollow body 56. FIG. 7 shows a first hollow body 58 with an opening 60 adapted to be joined to an opening 62 of a second hollow body 64, thereby forming a side-to-side anastomosis that places their lumens in communication. The openings 60, 62 are formed in the walls of the hollow bodies 58, 64, for example, as described above regarding opening 52. FIG. 8 shows a first hollow body 66 with an opening 68 adapted to be joined to an opening 70 of a second hollow body 72 to form an end-to-side anastomosis. Each opening 68, 70 is defined by an end its associated hollow body 66, 72.

Figure 9:
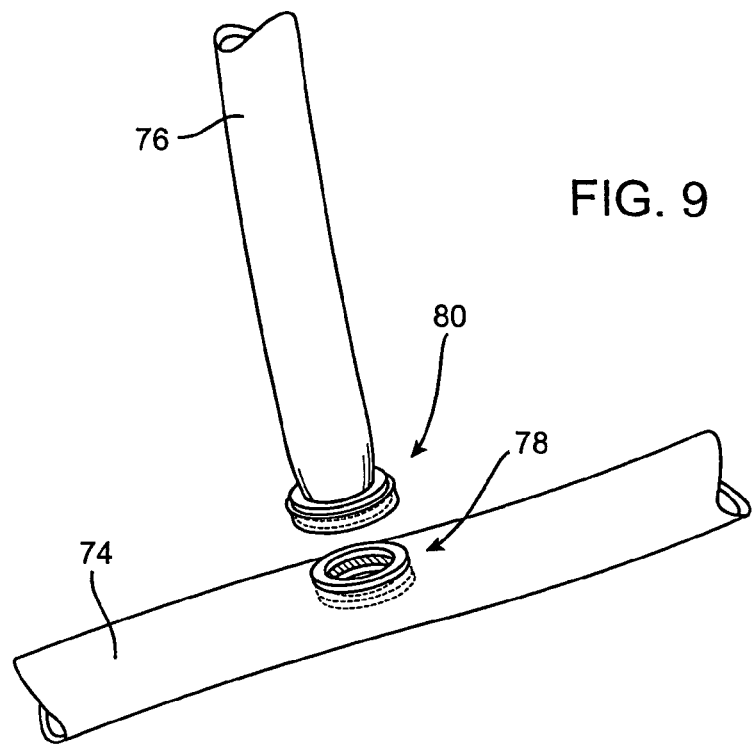
FIG. 9 is a perspective view of the two hollow bodies shown in FIG. 6 along with an anastomotic system including anastomotic securing components constructed according to one embodiment of the invention.
Figure 9A:
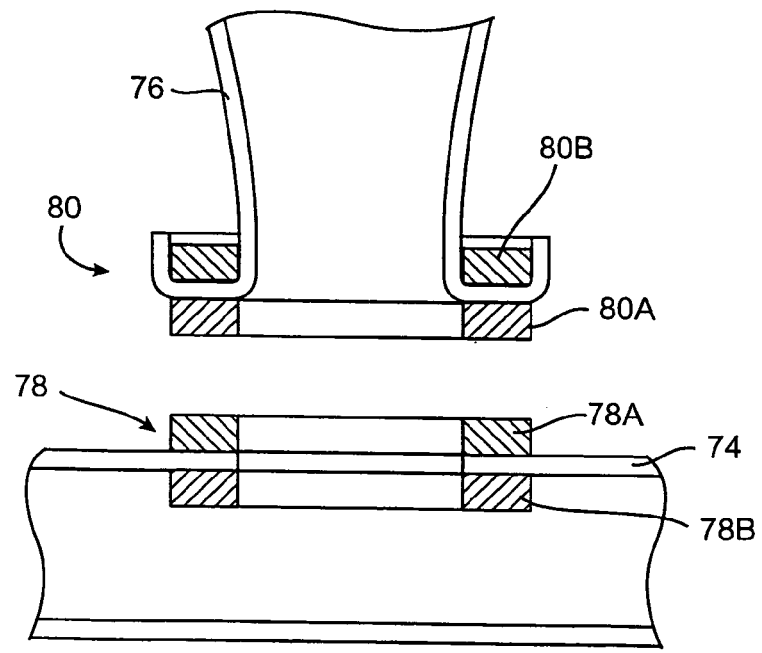
FIG. 9A is a sectional view taken along line A-A in FIG. 9.

FIGS. 9 and 9A show first and second hollow bodies 74, 76 respectively provided with first and second anastomotic securing components 78, 80 which are used to create an exemplary end-to-side anastomosis according to one embodiment of the invention. As shown best in FIG. 9A, the securing component 78 includes two members 78A, 78B disposed on opposite surfaces of a wall of the first hollow body 74. The securing component 80 includes two members 80A, 80B disposed on opposite surfaces of an everted end of the second hollow body 76. The members forming each securing component 76, 78 may be held in a desired and preferably fixed relative position by magnetic force, with magnetic force also being used to hold the two securing components in position. The securing components 78, 80 are moved together from the position of FIG. 9A to create a fluid-tight anastomosis.

Figure 10A:
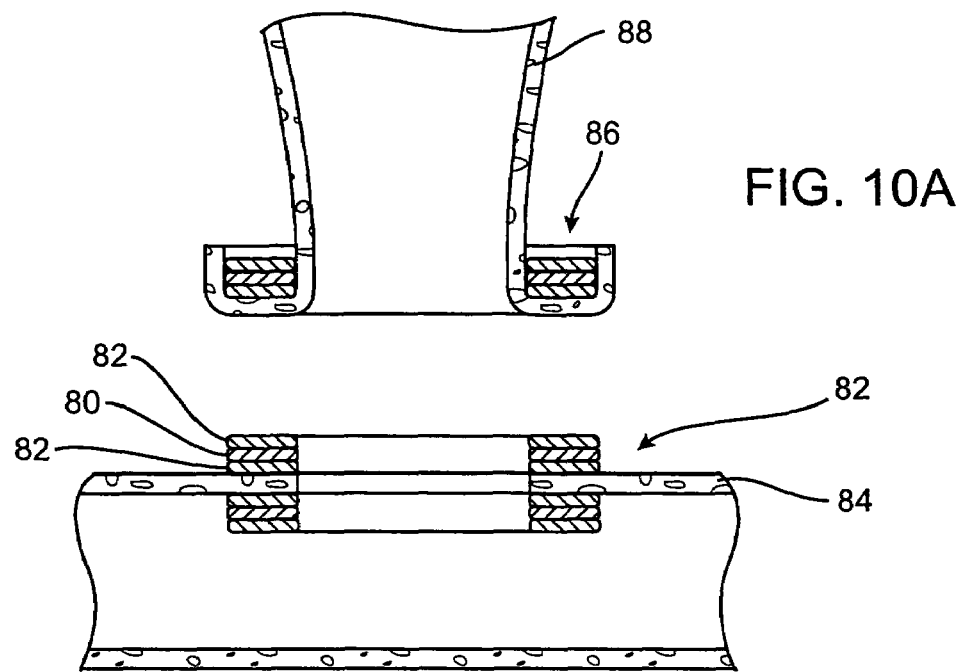
FIG. 10A is a section view similar to FIG. 9A but including alternative anastomotic securing components used to join the two hollow bodies.

FIGS. 10A-10D depict additional end-to-side anastomoses formed according to other embodiments of the invention. FIG. 10A shows a first securing component 82 coupled to a first hollow body 84 and a second securing component 86 coupled to a second hollow body 88. The securing components 82, 86 have a laminated structure comprising one layer of material capable of producing a magnetic field disposed between two outer layers of different material. In order to produce a magnetic field the components may comprise, for example, permanent magnetic, ferromagnetic, ferrimagnetic or electromagnetic materials or assemblies. Some exemplary materials that may be used include metals, polymers, ceramics, etc.

One example of this embodiment of the invention comprises a securing component having a middle layer of permanent magnetic material (e.g., NdFeB) and two outer layers of ferromagnetic material (e.g., 300 or 400 series stainless steel). The outer layers may be attached to the middle layer by suitable adhesive or magnetic force. One specific example of a securing component constructed according to this embodiment comprises a 0.008" thick inner magnetic layer and two 0.001" thick outer stainless steel layers. It will be understood that this aspect of the invention may be practiced using other materials or assemblies.

A benefit of a laminated construction is that it allows the thickness of the magnetic layer to be reduced because the other layer(s) will provide the assembly with the necessary strength and integrity, even if the magnetic layer is very thin (which typically makes the brittle magnet more easily fractured). In the above example, the steel layers may be very thin yet still able to absorb the load, e.g., the tensile forces that arise during movement of the hollow body or adjacent tissue. The particular overall dimensions of the securing component, as well as the dimensions of individual layer (or layers if a multilayer construction is used) will of course depend on the application. (As examples, for the securing component 22 shown in FIG. 3, the thickness is preferably less than 0.040", and more preferably less than 0.020", e.g., approximately 0.015" or even less, e.g., 0.008".)

The ability to form a very thin securing component allows formation of an anastomosis between relatively small hollow bodies, e.g., coronary blood vessels. Further, the anastomosis can be formed between blood-carrying hollow bodies with one or more of the securing components located in the blood flow path while minimizing the foreign material exposed to blood.

Figure 10B:
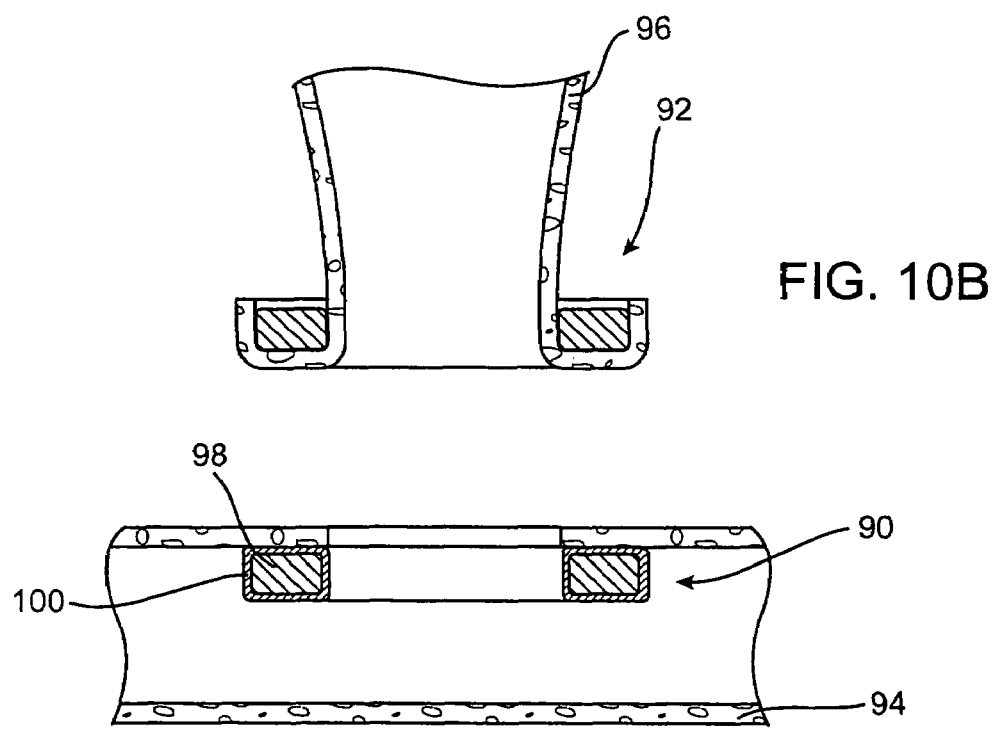
FIG. 10B is a section view similar to FIG. 10A including other alternative anastomotic securing components for joining the two hollow bodies.

FIG. 10B shows first and second securing components 90, 92 coupled to first and second hollow bodies 94, 96. The first securing component 90 comprises a single member 98 positioned within the lumen of the first hollow body 94 against the interior surface of the wall of the body adjacent an opening therein. The member 98 has a coating 100 substantially, and preferably completely, surrounding its exterior surface. It may be desirable in some applications to apply a suitable coating, or alternatively, a suitable surface treatment, to all or part of the anastomotic securing component. For example, if the first hollow body 94 represents a blood vessel such as a coronary or peripheral artery, the securing component 90 will be exposed to the blood flow path. As such, depending on the material used to the form the member 98, it may be desirable or necessary to coat or otherwise treat its surface to promote better thrombogenicity and/or improve flow past the anastomosis site. Some exemplary materials that may be used to coat or otherwise treat an anastomotic securing component constructed according to the invention include Gold, Platinum, Titanium Nitride, Parylene, Silicone, Urethane, Epoxy, Teflon and Polypropylene.

FIG. 10C shows an embodiment wherein first and second securing components 102, 104 are coupled to first and second hollow bodies 106, 108. Each component 102, 104 comprises a single member formed, as explained above, of a magnetic, ferromagnetic, or electromagnetic material. This embodiment, instead of everting an end of one of the hollow bodies 106, 108, provides the first securing component 102 with a portion 110 configured to attach the end of the first hollow body 106. The portion 110 may take various forms, for example, a DACRON® suture ring or bioadhesive. It will be recognized that the portion for attaching the hollow body may be located at different areas of the second securing component 104 than shown in FIG. 10C.

FIG. 10D shows an embodiment of the invention similar to that of FIG. 10C with first and second securing components 112, 114 coupled to first and second hollow bodies 116, 118. The means for attaching the first securing component 112 to the first hollow body 116 in this embodiment comprises an expandable member 120, such as a stent, disposed within the lumen of the first hollow body. The member 120 forces the end of the first hollow body 116 against the first securing component 112 to attach the elements in a fluid-tight fashion. It will be appreciated that the embodiments of FIGS. 10C and 10D are only two of the various ways in which a securing component may be coupled to a hollow body with everting tissue of the hollow body.

Figure 11A:
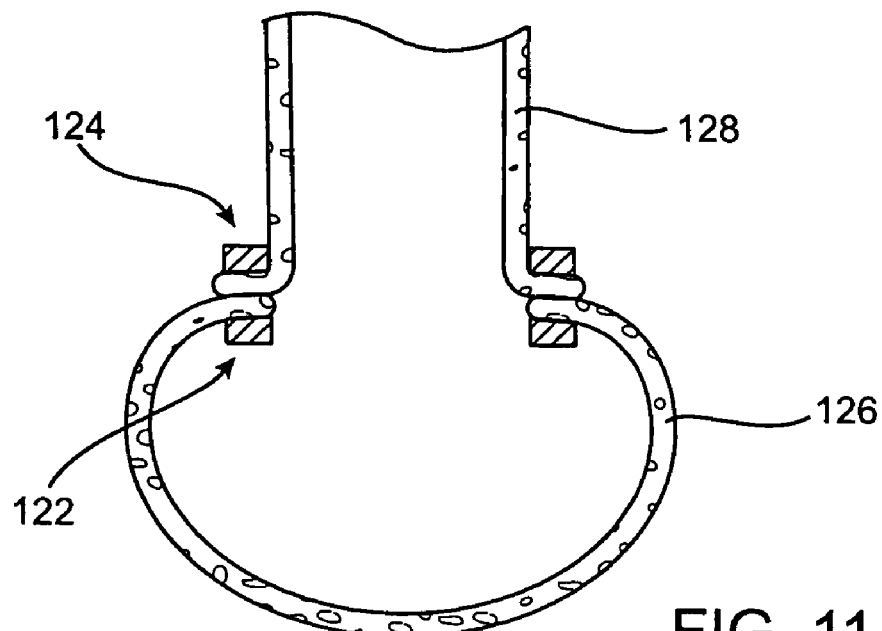
FIG. 11A is a transverse sectional view taken through an end-to-side anastomosis formed according to one embodiment of the invention.
Figure 11B:
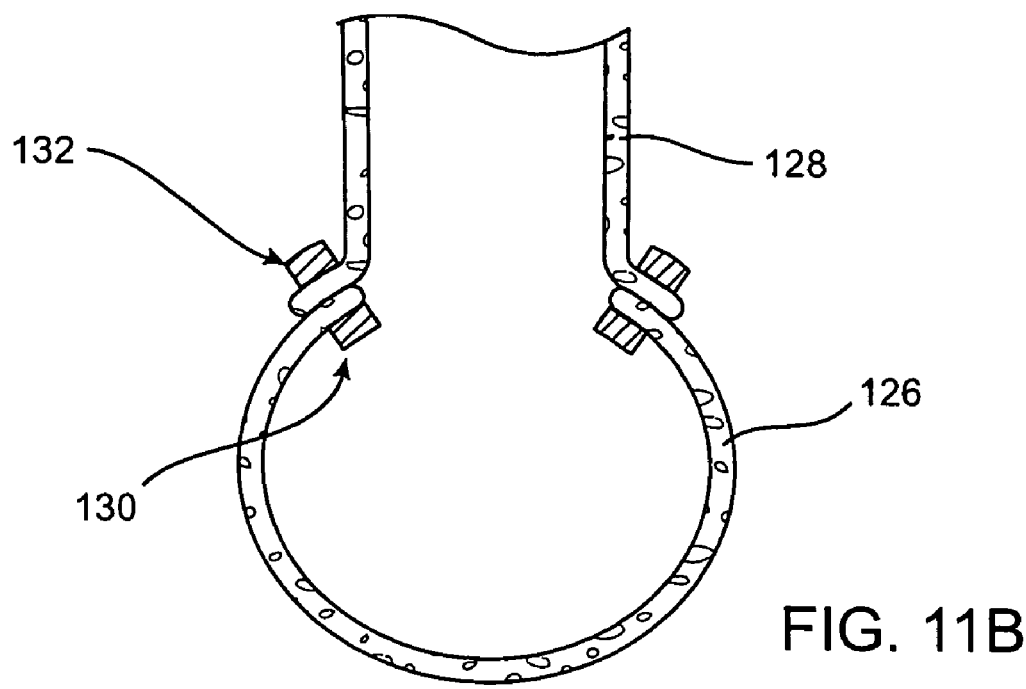
FIG. 11B is a transverse sectional view taken through an end-to-side anastomosis formed according to another embodiment of the invention.

FIG. 11A is a transverse sectional view taken through an end-to-side anastomosis created by first and second securing components 122, 124 which are positioned adjacent openings of first and second hollow bodies 126, 128. The securing components 122, 124 are plate-shaped (as described above) and generally flat. FIG. 11B shows first and second securing components 130, 132 constructed according to an alternative embodiment of the invention positioned adjacent the openings of first and second hollow bodies 126, 128. The securing components 130, 132 are also plate-shaped but, rather than being generally flat, are arcuate or curved. As can be seen, the curvature of the securing components 130, 132 maintains the first hollow body 126 in a substantially round configuration as compared to the more flattened-out shape it assumes when used with the flat securing components 122, 124.

The arcuate securing components 130, 132 preferably have complementarily or substantially complementarily radii of curvature to provide an even distribution of force and good sealing. The securing components of the invention could, however, have different degrees of curvature, the curvature of each being either constant or changing over the body of the component. Also, while the illustrated securing components 130, 132 extend over approximately 120°, other configurations that extend between 0° and 360° could be used if desired, for example, 180°. Finally, while FIGS. 11A and 11B show, respectively, a pair of flat components and a pair of arcuate components, the securing components of each pair used to create the anastomosis may have dissimilar configurations to varying degrees.

Figure 12:
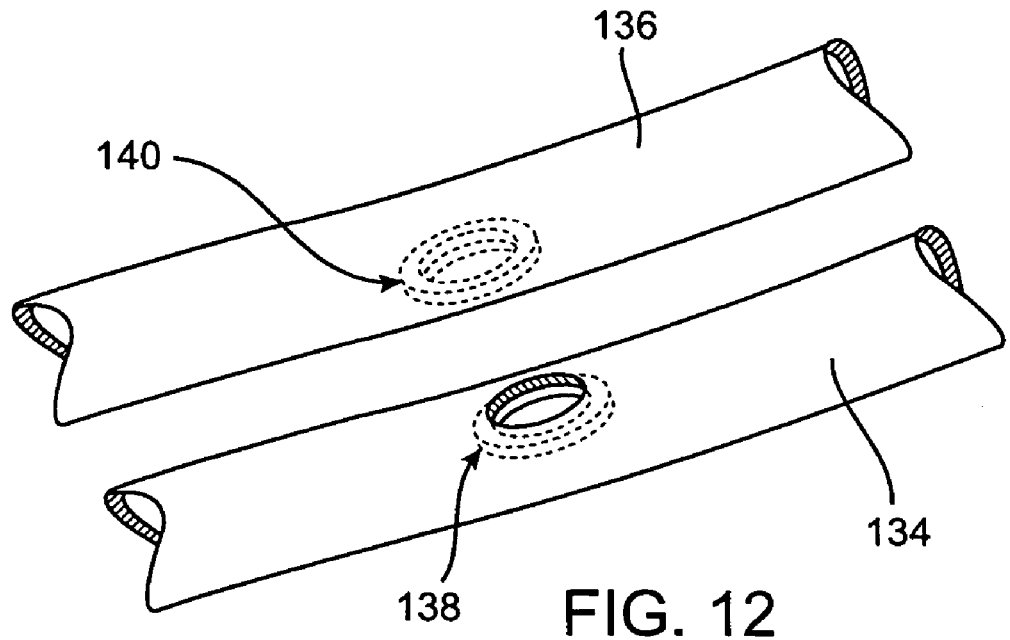
FIG. 12 is a perspective view showing two hollow bodies provided with anastomotic securing components constructed according to one embodiment of the invention, the two bodies adapted to be joined via a side-to-side anastomosis.
Figure 13:
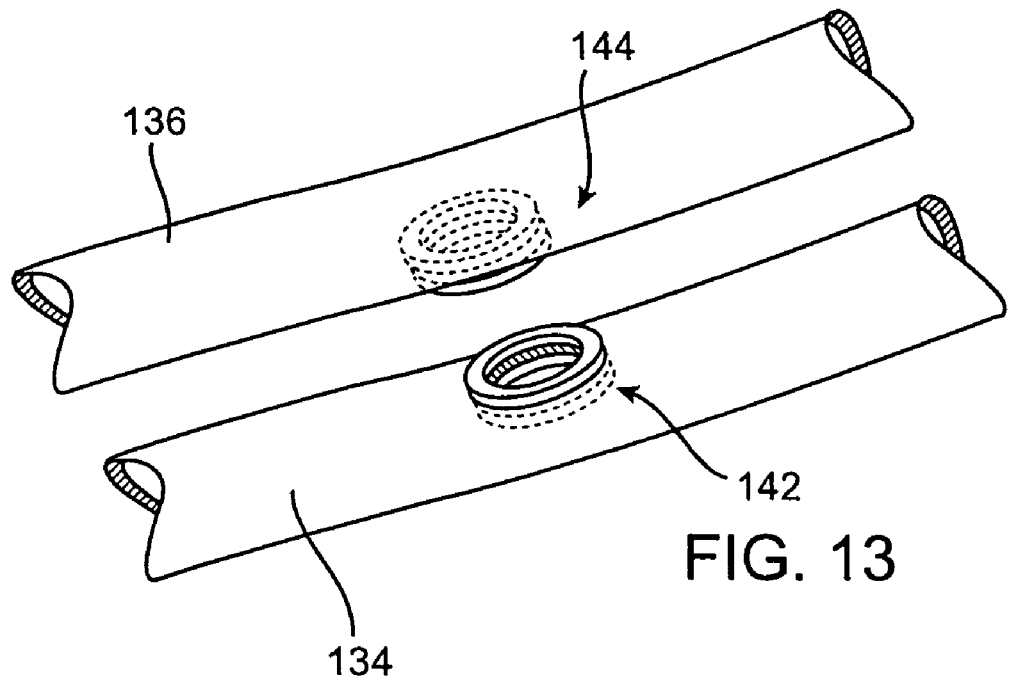
FIG. 13 is a perspective view showing the two hollow bodies of FIG. 12 provided with anastomotic securing components constructed according to another embodiment of the invention.
Figure 14A:
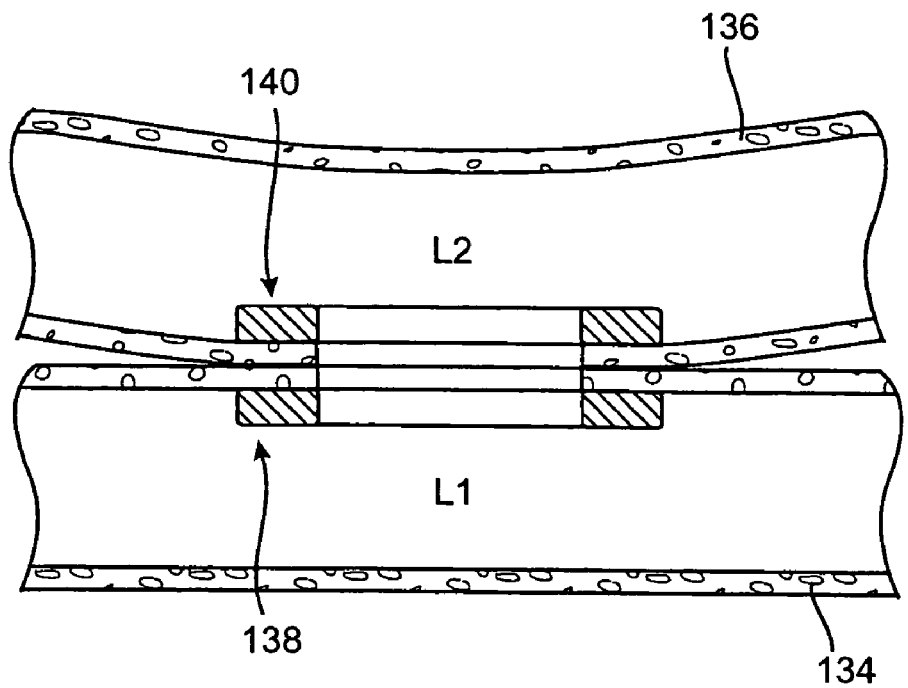
FIG. 14A is a longitudinal sectional view taken through the side-to-side anastomosis formed according to the embodiment shown in FIG. 12.
Figure 14B:
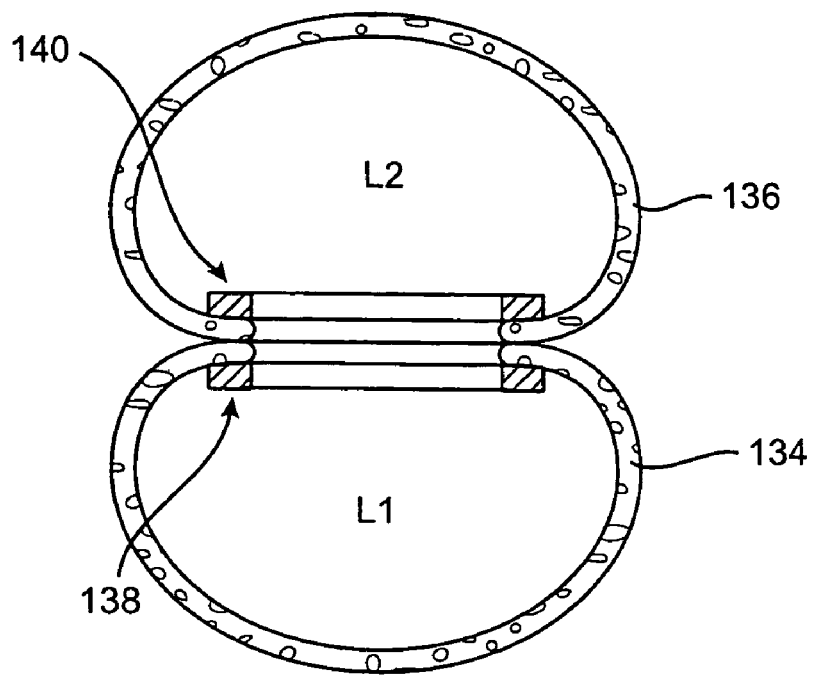
FIG. 14B is a transverse sectional view taken through the side-to-side anastomosis formed according to the embodiment shown in FIG. 12.

FIGS. 12 and 13 show other embodiments of the invention wherein first and second hollow bodies 134, 136 are respectively provided with securing components in order to create an end-to-side anastomosis. The embodiment of FIG. 12 utilizes first and second securing components 138, 140 respectively positioned adjacent openings in the hollow bodies 134, 136. Each securing component 134, 136 includes a single member that may comprise one or more materials and one or more layers, as described above. The components may be fixed by adhesive or other means or remain in position via magnetic force, as explained above. The securing components 138, 140 are positioned through openings formed in the wall of the hollow bodies 134, 136 and are located within the respective lumens L1, L2 thereof, as shown in FIGS. 14A and 14B. Once joined the components 138, 140 form a fluid-tight anastomosis that places the first and second hollow bodies 134, 136 in communication. If the hollow bodies 134, 136 are blood (or other fluid) carrying structures, the anastomosis places them in fluid communication and provides a fluid-tight seal.

The embodiment of FIG. 13 uses first and second securing components 142, 144 which are respectively positioned adjacent openings in the hollow bodies 134, 136 so as to be partially disposed within the lumens thereof. The opening in each hollow body may be formed by making a surgical incision, removing tissue with a punch, etc. Each securing component 142, 144 includes a pair of members, and each member may comprise one or more materials and one or more layers. One member of each securing component 142, 144 is positioned within the lumen of its hollow body while the other member of the securing component is positioned on the exterior of the hollow body with tissue in between.

Figure 15:
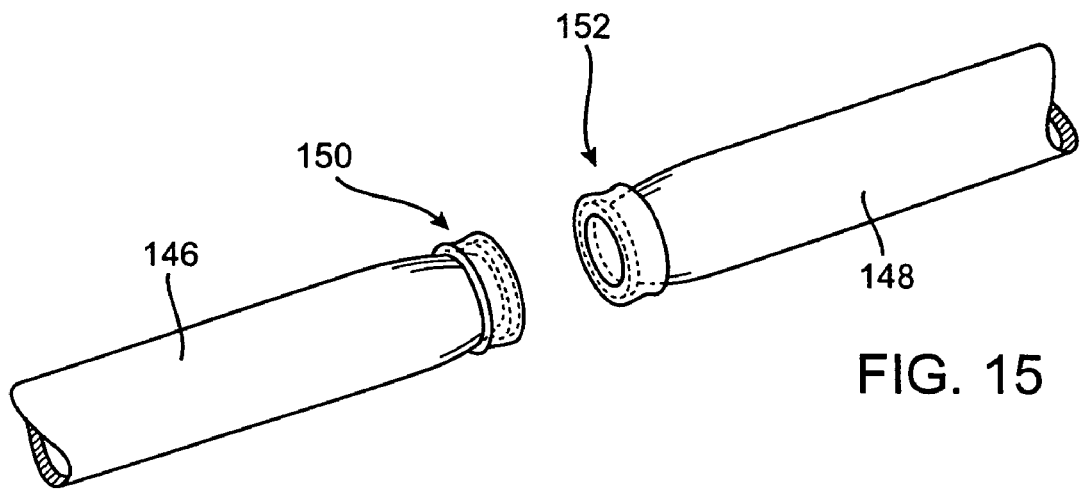
FIG. 15 is a perspective view showing two hollow bodies provided with anastomotic securing components constructed according to one embodiment of the invention, the two bodies adapted to be joined via an end-to-end anastomosis.
Figure 16:
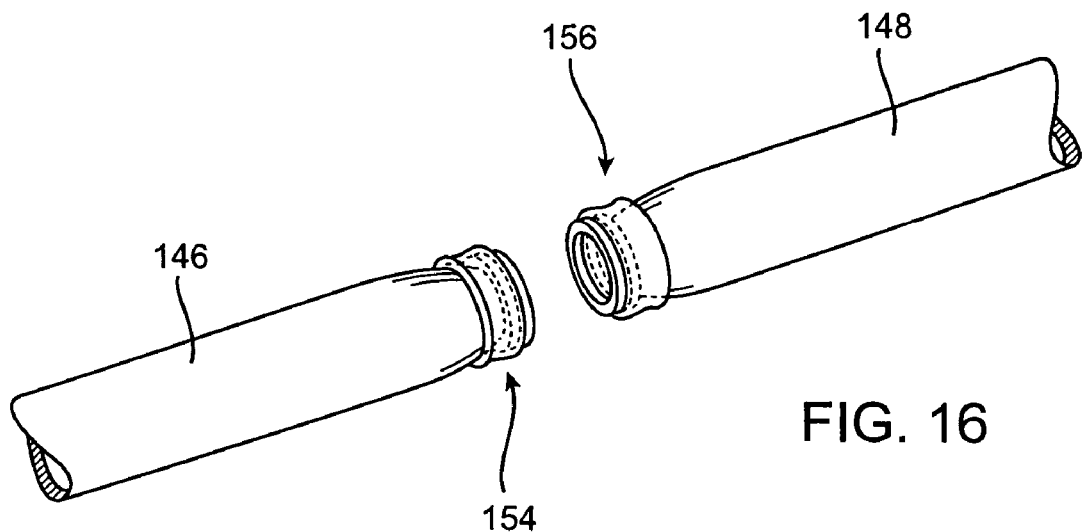
FIG. 16 is a perspective view showing the two hollow bodies of FIG. 15 provided with anastomotic securing components constructed according to another embodiment of the invention.

FIGS. 15 and 16 show further embodiments of the invention wherein first and second hollow bodies 146, 148 are respectively provided with first and second anastomotic securing components in order to create an end-to-end anastomosis. FIG. 15 shows first and second securing components 150, 152 positioned adjacent respective openings of the hollow bodies 146, 148, each opening being defined by an end of a hollow body and extending into the lumen thereof.

Each securing component 150, 152 includes a single member that may be constructed as described above. An end of each hollow body 146, 148 is passed through the opening defined in by a respective securing component and then is everted over the exterior of the component. As a result, joining the first and second securing components 150, 152 in end-to-end fashion places the everted ends of the hollow bodies 146, 148 in sealed contact. In a case where the hollow bodies are natural blood vessels, such an anastomosis places the intimal surfaces of the vessels in contact.

The embodiment of FIG. 16 includes first and second securing components 154, 156 positioned adjacent the openings of hollow bodies 146, 148, respectively. The securing components 154, 156 each comprise a pair of members constructed as described above. The first securing component 154 includes one member 154A positioned around the exterior of the first hollow body 146 (with the end thereof everted), and another member 154B positioned around the opening defined by the end of the hollow body 146, the members 154A, 154B being held in place by magnetic force. The second securing component 156 has the same or a similar construction and includes members 156A, 156B which are positioned adjacent the end of the second hollow body 148. In the embodiments of FIGS. 15-16 the securing components are not located within the lumen of either hollow body and thus are not exposed to fluid or other substances contained therein or moving therethrough.

Figure 17A:
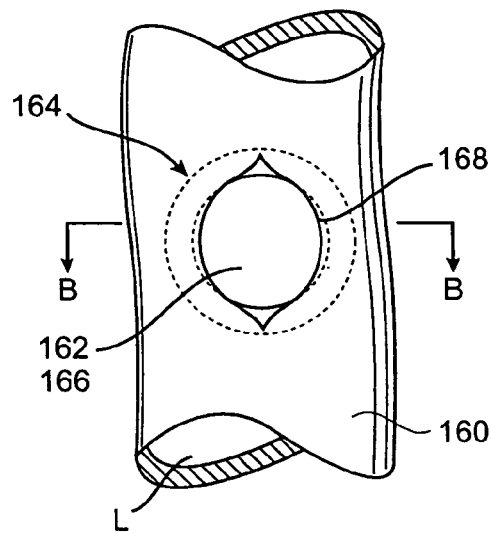
FIG. 17A is a plan view of one of the hollow bodies and securing components shown in FIG. 12.
Figure 17B:
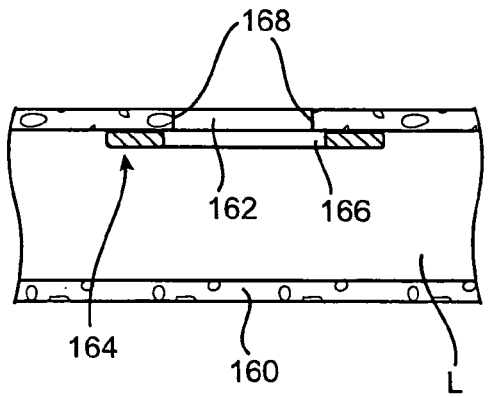
FIG. 17B is a longitudinal sectional view of the hollow body and securing component shown in FIG. 17A.

Another embodiment of the invention will be described with reference to FIGS. 17A-17B. FIG. 17A shows a hollow body 160 with an opening 162 and an anastomotic securing component 164 positioned adjacent the opening. The securing component 164 is positioned within the lumen L of the hollow body 160 and has an opening 166. The opening 166 is aligned with the opening 162 in the wall of the body 160 as shown. In some instances, for example, when the securing component is forced through an incision in the wall, the tissue defining the opening 162 may move over the opening 166 of the securing component 164, as shown in FIG. 17B. As indicated by reference numeral 168 in FIG. 17B, this reduces the effective area of the securing component 164 that is available to communicate with a second hollow body to which the hollow body 160 is anastomosed (not shown).

Figure 18A:
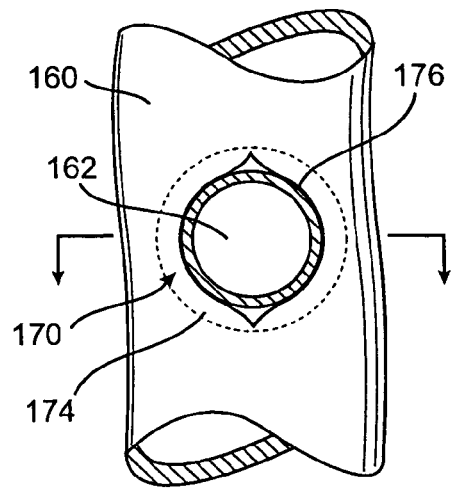
FIG. 18A is a plan view of the hollow body of FIGS. 17A-17B and a securing component constructed according to an alternative embodiment of the invention.
Figure 18B:
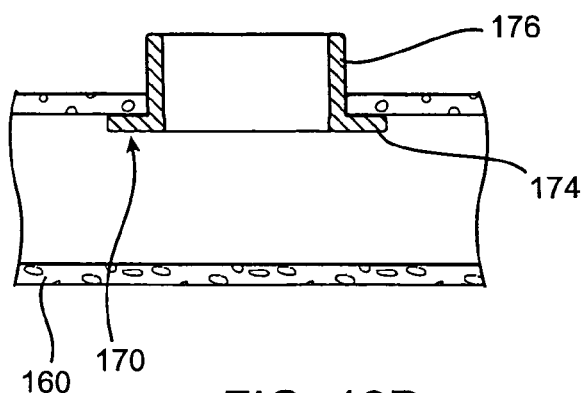
FIG. 18B is a longitudinal sectional view of the hollow body and securing component shown in FIGS. 18A.

FIG. 18A-18B show the hollow body 160 with the opening 162 of FIGS. 17A-17B, however, a securing component 170 constructed according to another embodiment of the invention is positioned adjacent the opening 162. The securing component 170 has an opening 172 and has a feature for maintaining the opening 162 open to flow. The securing component 170 comprises a flange 174 and an extension 176 coupled thereto (or formed integrally therewith). As can be seen, the extension 174 prevents tissue defining or adjacent the opening 162 of hollow body 160 from migrating or springing back after delivery to reduce the cross-sectional flow area of the securing component 170.

Figure 19A:
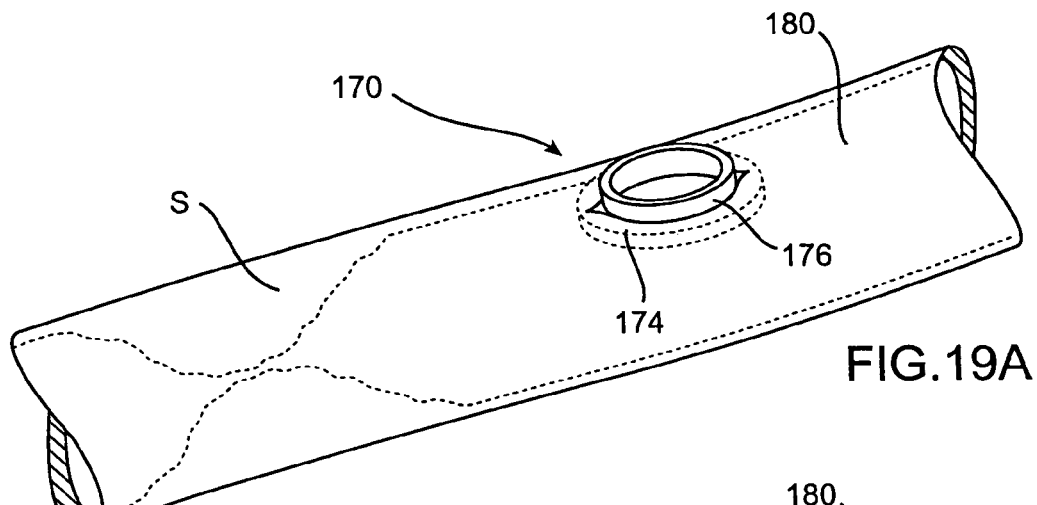
FIG. 19A is a perspective view of the anastomotic securing component shown in FIGS. 18A-18B, the component positioned in an opening in a hollow body with a lumen having a stenosis disposed proximal to the opening.
Figure 19B:
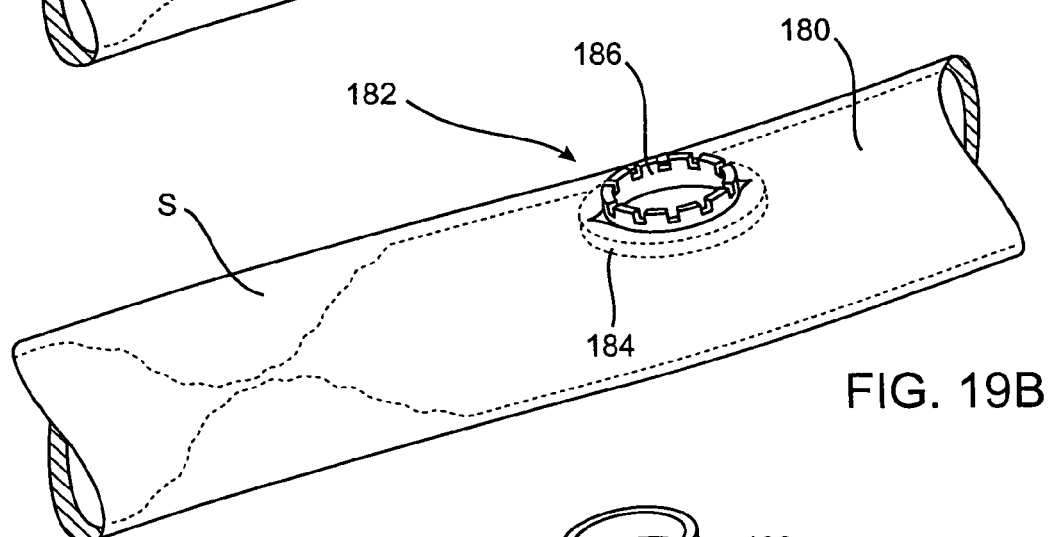
FIGS. 19B-19C show anastomotic securing components constructed according to further alternative embodiments of the invention, the components being shown positioned in the hollow body of FIG. 19A.
Figure 19C:
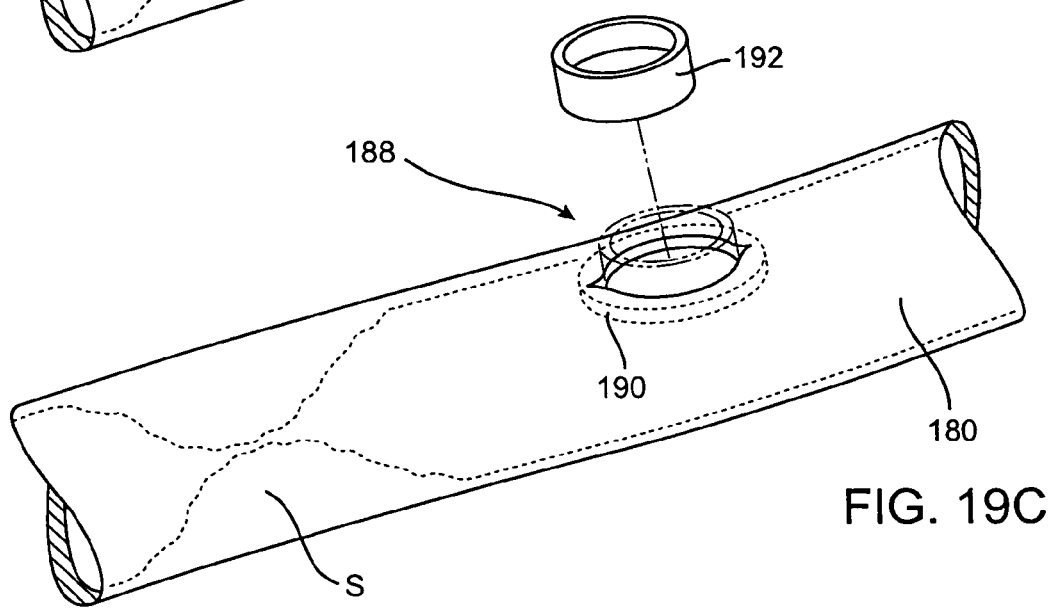

FIGS. 19A-19C show a hollow body 180 which may, for example, represent a patient's coronary or peripheral artery the lumen of which is stenosed at S. In FIG. 19A, the hollow body 180 is provided with the anastomotic securing component 170 of FIGS. 18A-18B by coupling the securing component to an opening in the wall of the artery, thereby forming a site for creating an end-to-side or side-to-side anastomosis. In FIG. 19B, the hollow body 180 is provided with an alternatively configured anastomotic securing component 182 which includes a flange 184 and a discontinuous or segmented extension 186 passing all or partly through the opening in the wall of the hollow body. FIG. 19C shows a securing component 188 with a multi-part construction including a flange 190 and a separate extension 192 which is received in the opening of the hollow body 180. It should be understood that these are only a few of the various constructions that may be employed in practicing this aspect of the invention.

Figure 20A:
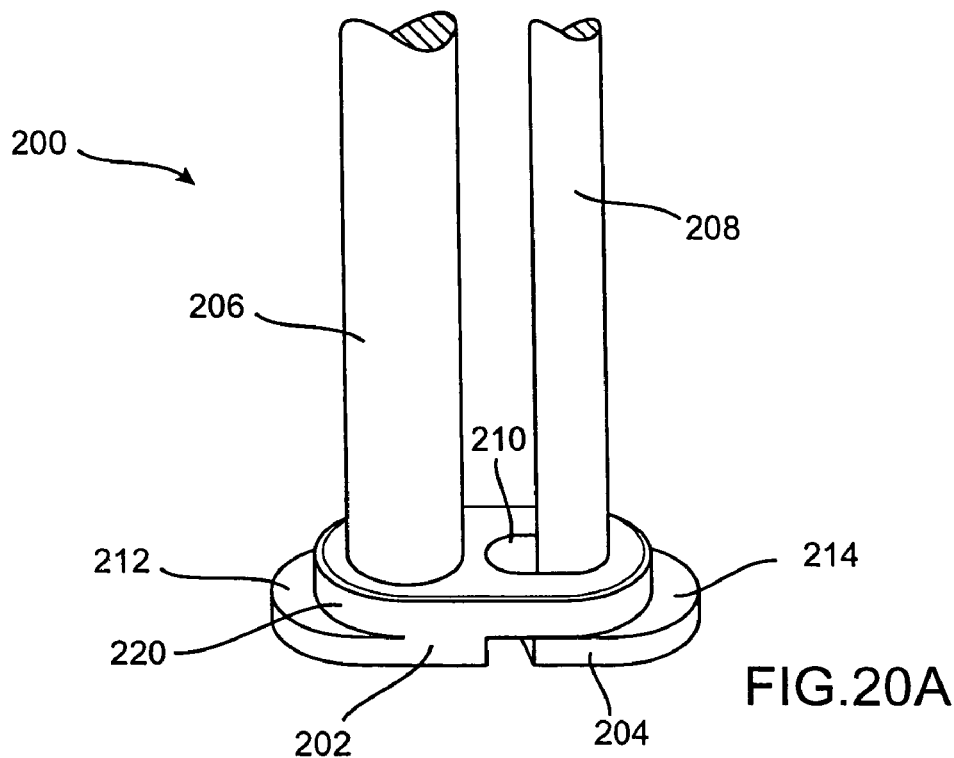
FIG. 20A is a perspective view of a delivery device constructed to one embodiment of the invention, the device being shown in a first position.

The anastomotic securing components of the invention may be delivered and deployed in various ways. FIGS. 20A-20B and 21A-21B depict somewhat schematically an exemplary delivery device 200 including a first portion 202 operatively coupled to a second portion 204. The first portion 202 is fixed to a shaft 206 while the second portion 204 is fixed to shaft 208 passing through a slot 210 in the portion 202. The first portion 202 defines a support ledge 212 and the second portion 202 similarly defines a support ledge 214. FIG. 20A shows the device 200 in a first position for retaining an anastomotic securing component of the invention. This position is shown in FIG. 21A wherein the ledges 212, 214 support a securing component 216 with the opening 218 of the component surrounding a boss 220 that extends upwardly from the ledges. The boss 220 is preferably used to help align the securing component on the support ledges 212, 214 and, if used in an application with an opening formed in a side wall of a hollow body, to restrain the surrounding tissue during placement.

Figure 20B:
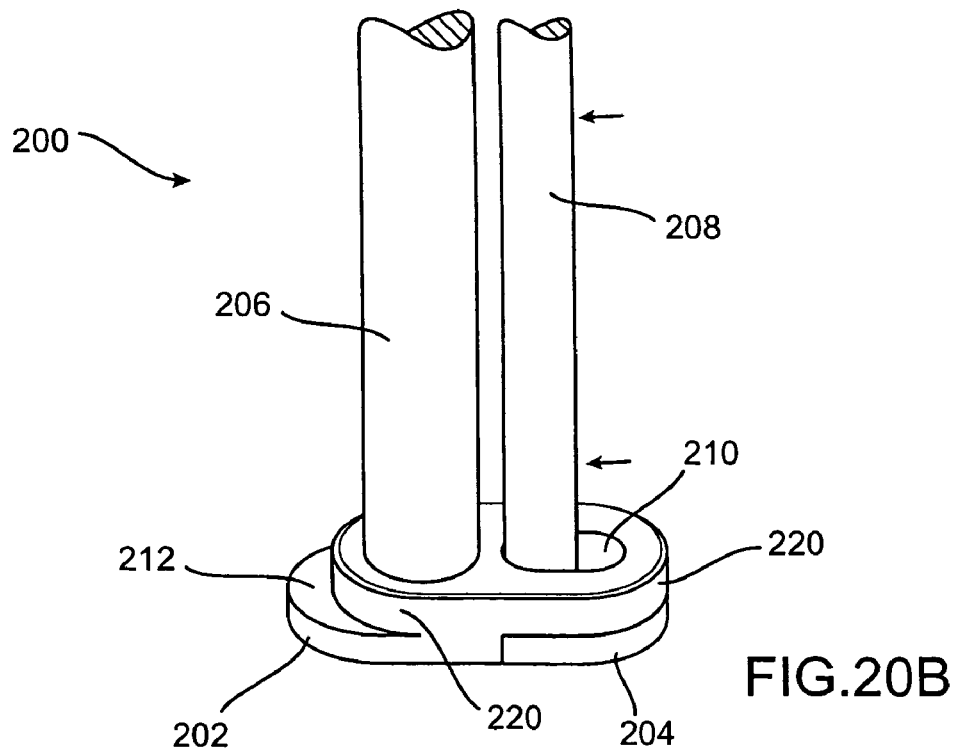
FIG. 20B is a perspective view of the delivery device shown in FIG. 20A, the device being shown in a second position.
Figure 21A:
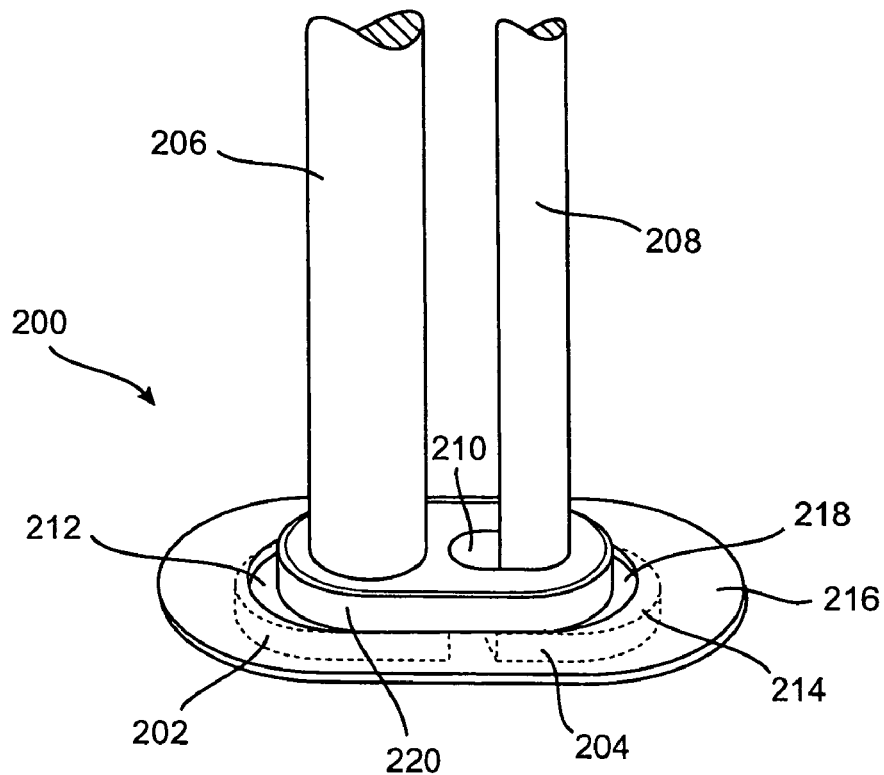
FIG. 21A is a perspective view of the delivery device shown in FIG. 20A with a securing component constructed to one embodiment of the invention mounted thereon, the delivery device being shown in the first position.
Figure 21B:
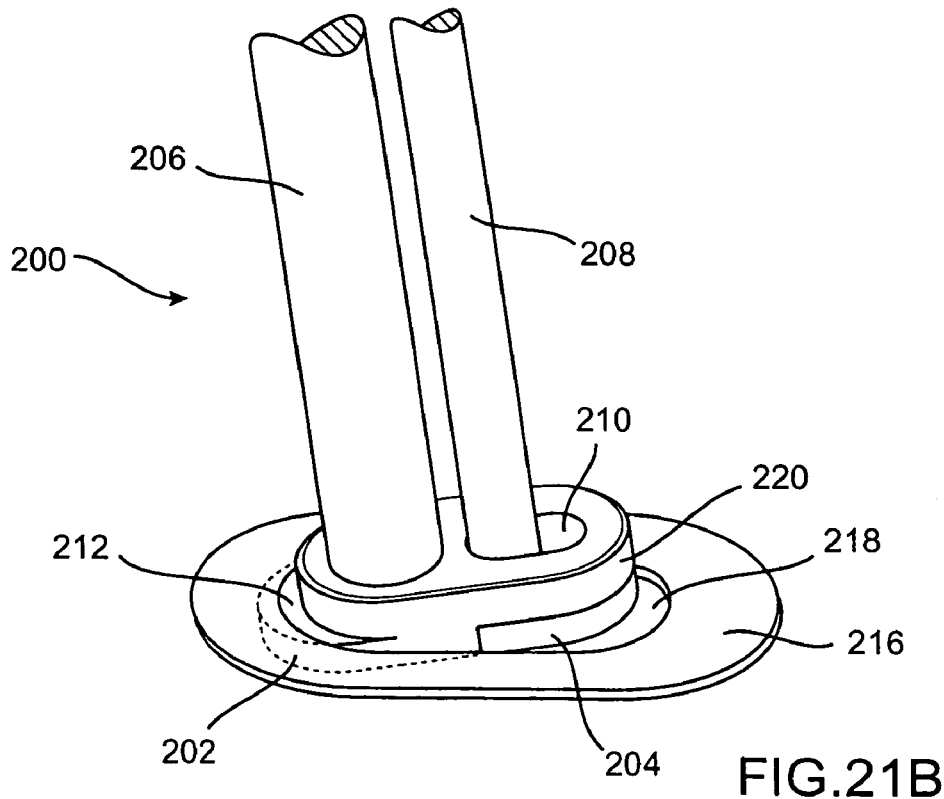
FIG. 21B is a perspective view of the delivery device shown in FIG. 21A, wherein the device is shown in the second position as it is being manipulated to release the securing component.

FIGS. 20B and 21B show the device 200 after it has been moved to a second position from the position of FIGS. 20A and 21A. This is achieved by moving the shaft 208 in the direction of the arrows to slide the second portion 204 with respect to the first portion 202, which moves the support ledge 214 within the opening 218 of the anastomotic securing component 216 (FIG. 21B). This allows the user to separate the device 200 from the securing component 216 once the latter has been positioned at the desired location. As shown, depending on the relative dimensions and shapes of the respective components it may be necessary to rock or otherwise manipulate the device 200 relative to the securing component 216 in order to separate them.

It will be understood that the illustrated delivery device 200 is only one possible device suitable for use in placing the anastomotic securing components of the invention, and that it may be modified or replaced with a different delivery device or system. For example, the delivery device 200 could be altered so that both support ledges 212, 214 are moved with respect to the boss 220 (if used) in order to move fully out of contact with and release the securing component. Any suitable material(s) may be used to construct the delivery device 200, it being appreciated using magnetic or ferromagnetic materials may result in magnetic interaction with the securing components, which may be desired to facilitate delivery of the components. The delivery device could also be constructed of nonmagnetic or ferromagnetic materials such as titanium, polymers, etc.

Figure 22A:
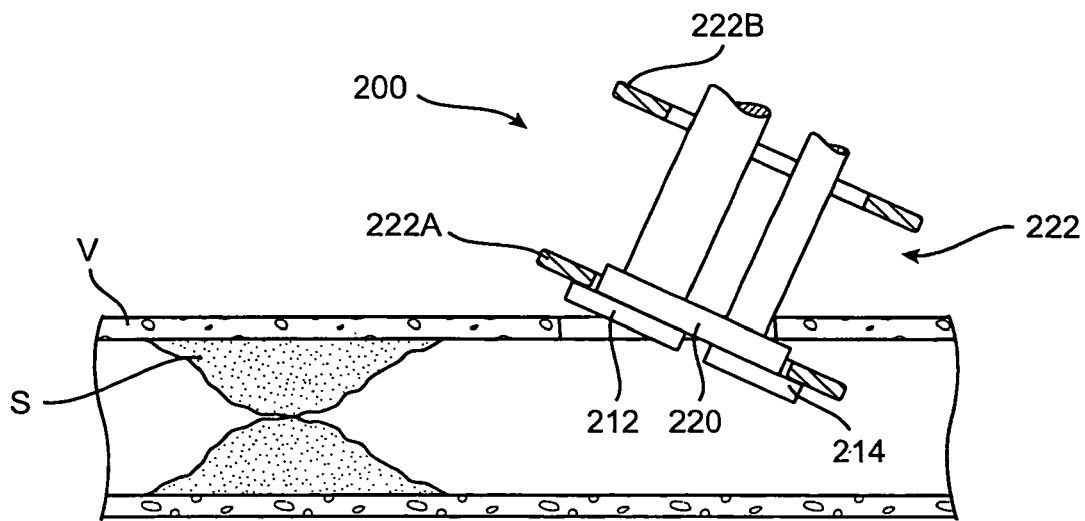
FIGS. 22A-22F are sectional views schematically illustrating the delivery device shown in FIGS. 20A-20B being used to deploy anastomotic securing components to form an end-to-side anastomosis according to one embodiment of the invention.

For sake of example, the creation of an anastomosis using the delivery device 200 and first and second securing components of the invention will be described with respect to FIGS. 22A-22F. FIG. 22A shows the delivery device 200 with a first securing component 222 comprising two members 222A, 222B, the former member being supported by the ledges 212, 214 of the device 200 while the latter member is held above the ledges (e.g., by magnetic attraction to the device 200). The member 222A is being inserted into an opening in the wall of a blood vessel V with a stenosis S. The member 222A may be shaped or otherwise treated to ease insertion into the vessel lumen; for example, the leading edge of the member 222A may be formed as shown in the embodiment of FIG. 5.

Figure 22B:
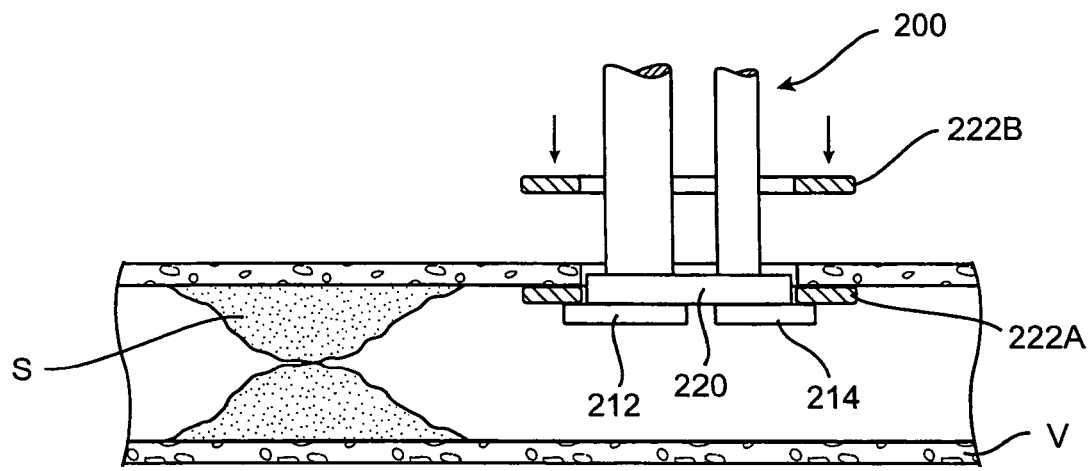
Figure 22C:
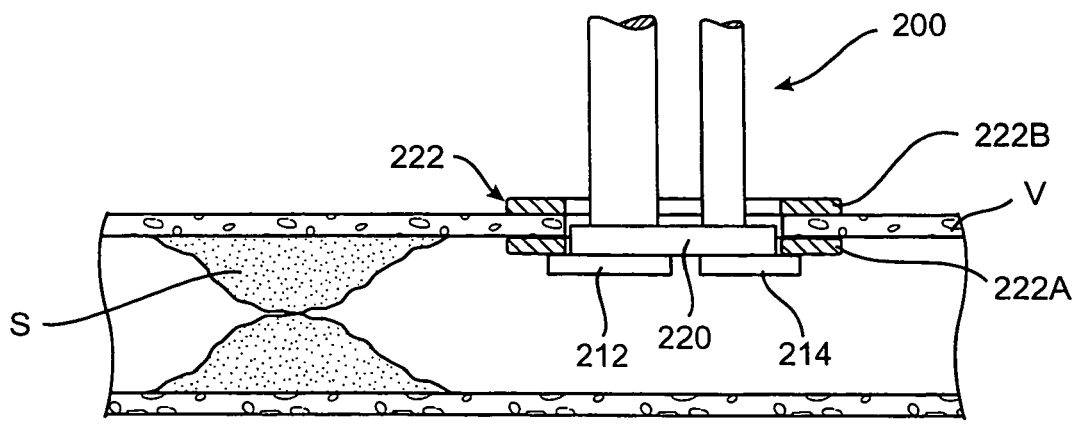
Figure 22D:
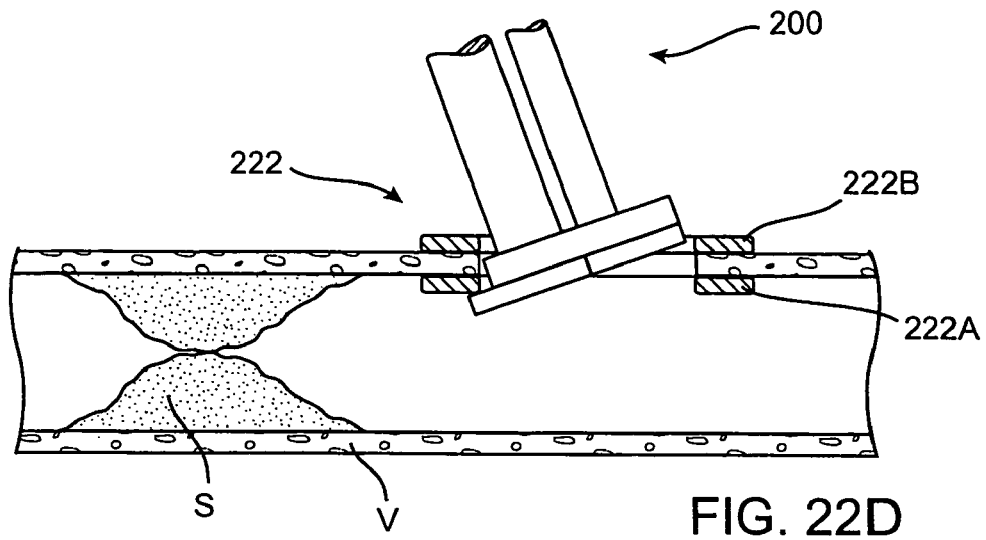
Figure 22E:
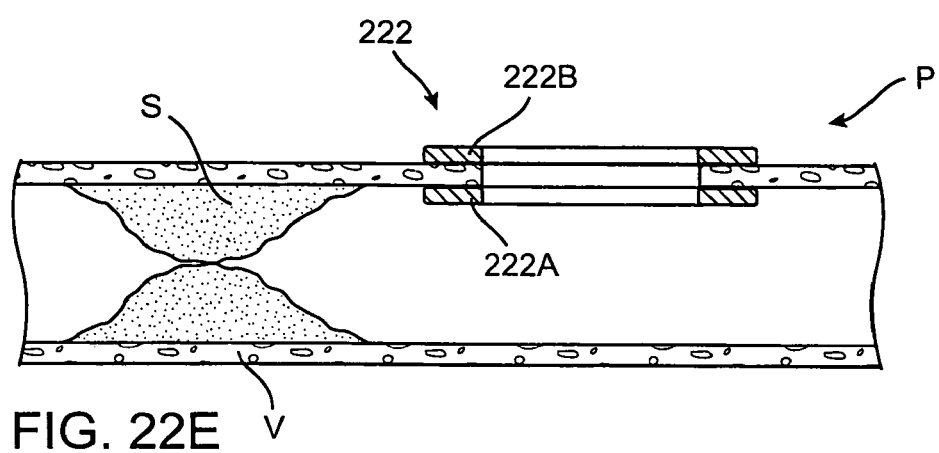

FIG. 22B shows the one member 222A of securing component 222 positioned against the interior surface of the wall of the vessel and the other member 222B being moved toward the vessel wall. FIG. 22C shows the members 222A, 222B in position with the delivery device 200 remaining. FIG. 22D shows the device 200 being removed through first securing component 222, and FIG. 22E shows the securing component 222 remaining in the vessel wall to form what may be characterized as a magnetic port P. The securing component(s) may be provided with a surface treatment, such as coatings, roughened or treated areas, or mechanical projections, to enhance engagement with the wall of the hollow body.

Figure 22F:
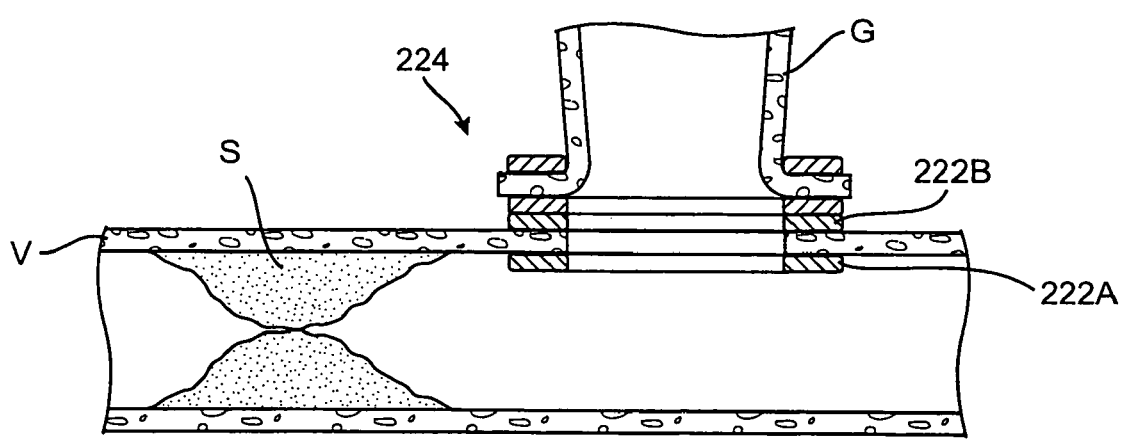

The illustrated securing component 222 defines the magnetic port P and produces a magnetic field that may be used to couple another vessel to the port. In FIG. 22F, a graft vessel G provided with a second securing component 224 (which itself includes two members) is anastomosed to the port P with magnetic force holding the first and second securing components 222, 224 in a desired relative position. The invention may also be practiced using means for fixing the relative distance between the first and second securing components, for example, to prevent tissue being forced or squeezed from the space between the components due to the application of the magnetic force over time. Such means could comprise projections that extend directly between the components and act as a stop, or an intermediate element coupled to the components to restrain them against further movement. It will be recognized that forming a magnetic port according to the invention may also be used in non-vascular applications, as well as applications not requiring an anastomosis to another vessel, for example, to provide an access to an area of a patient's body.

Figure 23:
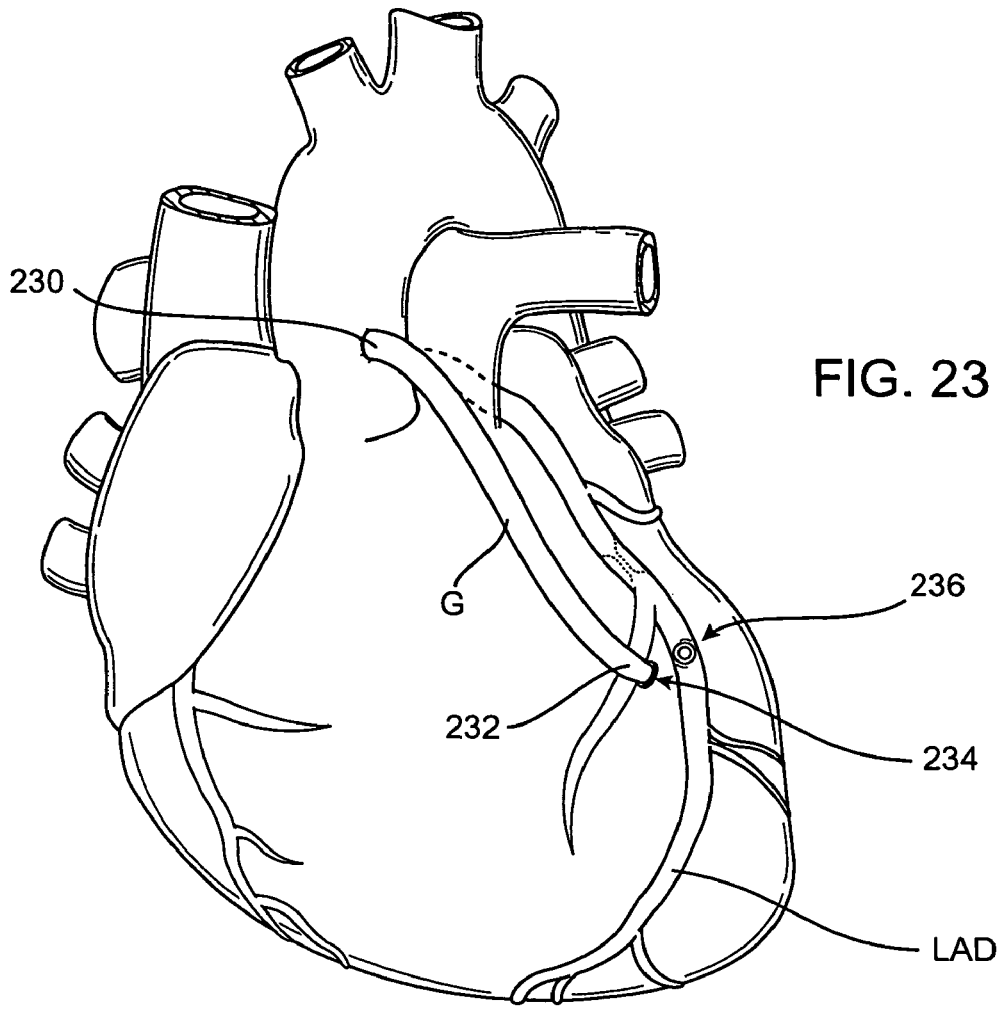
FIG. 23 is a perspective view of an exemplary application according to one embodiment of the invention.
Figure 23A:
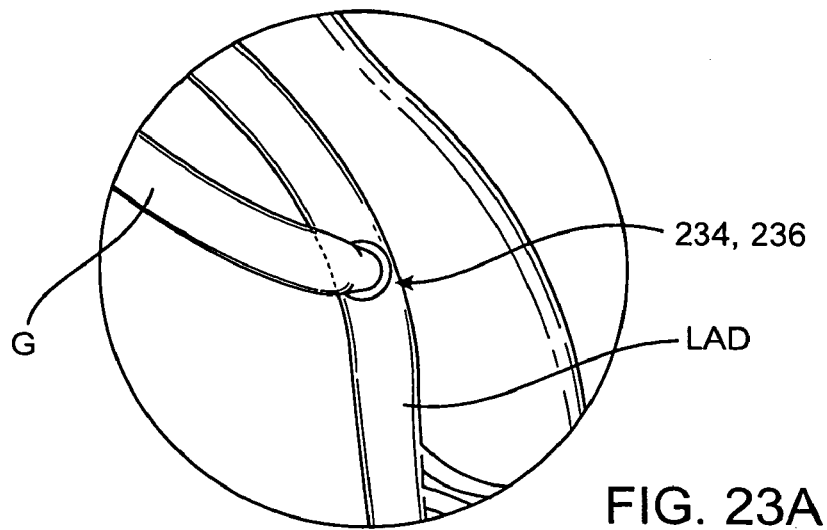
FIG. 23A is an enlarged view of a portion of the embodiment of FIG. 23 but showing a completed anastomosis.

Several exemplary applications of the invention will be described with reference to FIGS. 23-23A, 24-24A and 23-25A. FIG. 23 is an anterior view of a human heart with a graft vessel G having one end 230 attached to the aorta, e.g., by a sutured anastomosis, and another end 232 prepared to be anastomosed to an occluded LAD. One securing component 234 is coupled to the end 232 of the graft G by any of the methods described above, and another securing component 236 is coupled to the LAD adjacent an opening therein. The securing components 234, 236 are formed (at least in part) of materials capable of producing a magnetic field so that they may be attached as shown in FIG. 23A, thereby placing the graft G in fluid communication with the lumen of the LAD. The graft G could alternatively be attached to the aorta by an anastomotic system constructed according to the invention.

Figure 24:
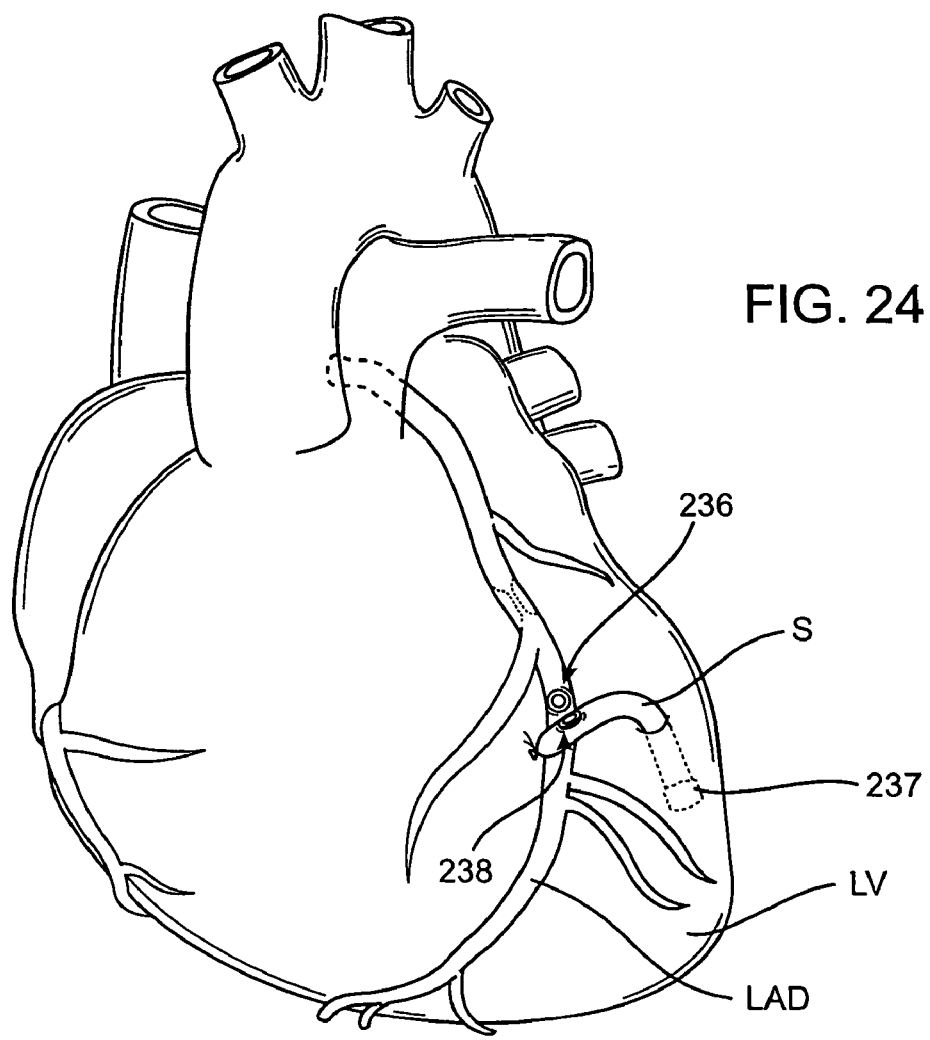
FIG. 24 is a perspective view of another exemplary application according to another embodiment of the invention.
Figure 24A:
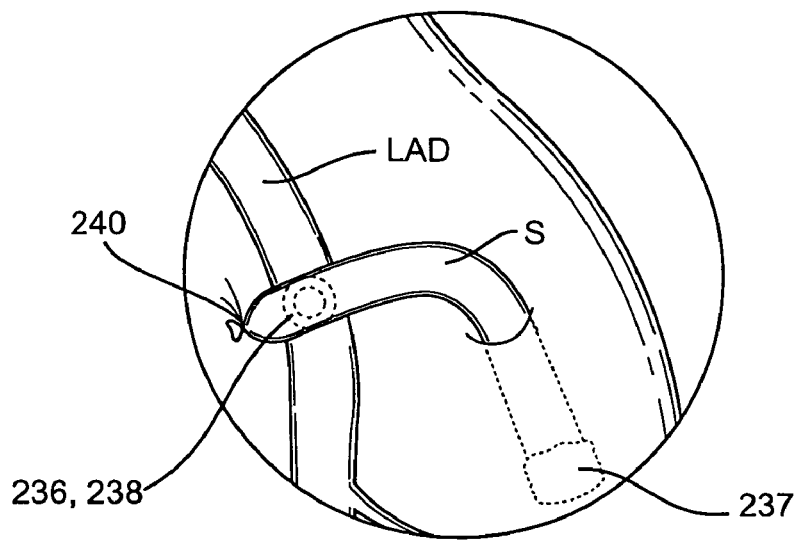
FIG. 24A is an enlarged view of a portion of the embodiment of FIG. 24 but showing a completed anastomosis.

FIG. 24 shows another exemplary application of the invention applied to the heart shown in FIG. 23. A ventriculocoronary shunt S has one end 237 placed in the myocardium in fluid communication with the left ventricle LV. The shunt S is provided with a securing component 238 adjacent its other end while the LAD is provided with the securing component 236 of FIG. 23. The shunt S is adapted to be coupled to the LAD via a side-to-side anastomosis, therefore the securing component 238 is positioned in an opening in the side wall of the shunt (and the free end of the shunt is tied off at 240). FIG. 24A shows the completed anastomosis once the securing components 236, 238 have been coupled and remain in position via the magnetic field produced according to the teachings of the invention.

Figure 25:
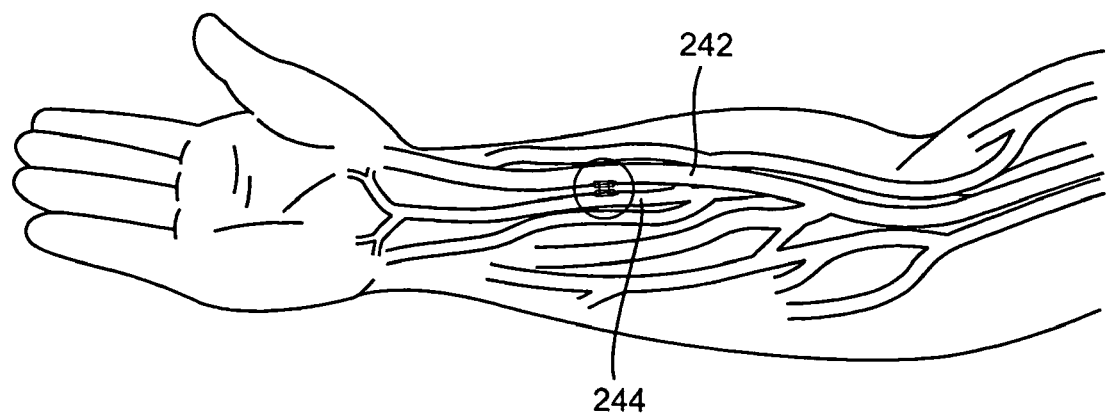
FIG. 25 is a perspective view of an exemplary application according to still another embodiment of the invention.
Figure 25A:
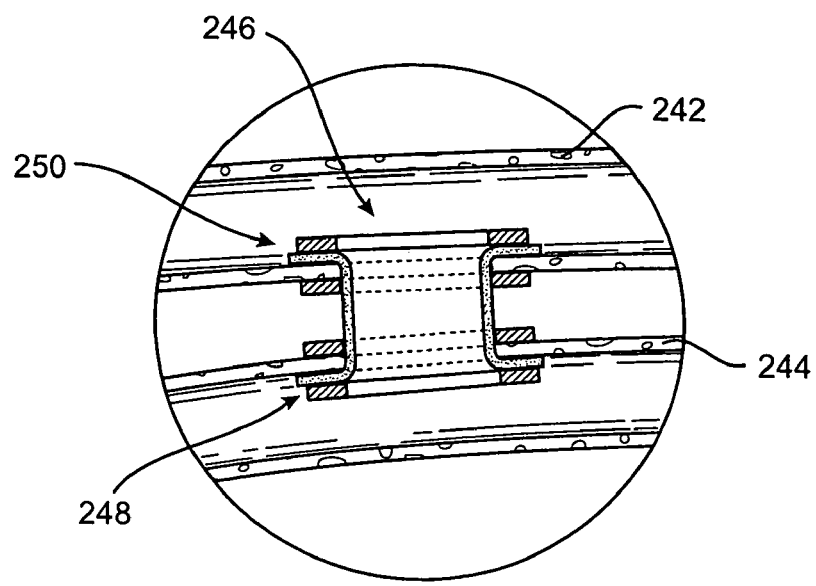
FIG. 25A is an enlarged view of a portion of the embodiment of FIG. 25 but showing a completed AV shunt with two anastomoses.

FIGS. 25-25A illustrate yet another example of the many different applications of the invention, namely, the creation of an AV shunt. FIG. 25 shows a patient's arm including a number of the blood vessels located therein. An artery 242 is shown disposed in relatively close proximity to a vein 244. AV shunts are often created between an artery and vein in order to provide a site for repeatedly accessing a patient's vascular system, for example, to treat dialysis patients. The shunt itself is typically formed of synthetic graft material and can withstand repeated needle sticks much better than a natural vein. An AV shunt 246 is created between the artery 242 and vein 244 by forming a side-to-side anastomosis using first and second securing components 248, 250. The shunt 246 is preferably formed of ePTFE, DACRON® or another suitable synthetic graft material.

It should be appreciated that the applications of FIGS. 23-23A, 24-24A and 23-25A represent several of many different uses for the invention. Other applications for the invention include, for example, neurological, urological and gastrointestinal procedures. As a further example, the invention could be used to form an anastomosis with an existing CABG graft that has partially or completely occluded over time, for instance, by placing the anastomotic securing components in the graft distal to the occlusion in short, it will be recognized that the invention may be modified in varying degrees from the preferred embodiments illustrated and described specifically herein.

As noted above, it will be recognized that the invention may be used in many different procedures, for example, femoral-femoral, femoral-popliteal, femoral-tibial, iliofemoral, axillary-femoral, subclavian-femoral, aortic-bifemoral, aorto-iliac, aorto-profunda femoris and extra-anatomic bypasses. In sum, the invention may be used to create an anastomosis with many different vessels, including, without limitation, the renal arteries, mesenteric vessel, inferior mesenteric artery, eroneal trunk, peroneal and tibial arteries.

Figure 26A:
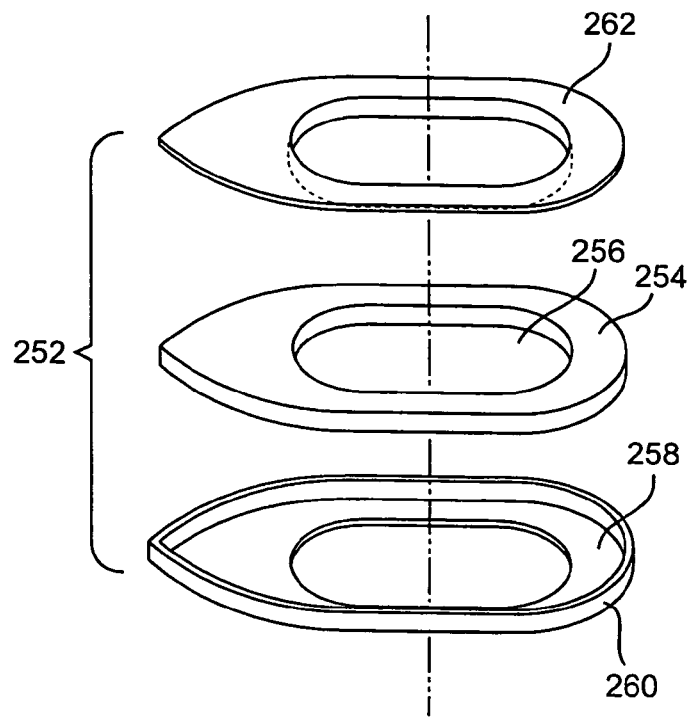
FIGS. 26A-26B are exploded perspective views of a device constructed according to one embodiment of the invention for forming a magnetic port in a hollow body having a lumen.

Another embodiment of the invention will be described with respect to FIGS. 26A-26D. A device for forming a port into a vessel (or for forming part of an anastomotic coupling) is indicated generally by the reference numeral 252 in FIG. 26A. The device 252 includes a member capable of producing a magnetic field, for example, permanent magnet 254, which preferably has an opening 256 adapted to communicate with a vessel lumen or other hollow body. The magnet 254 is received in a housing that, in this embodiment, comprises two elements configured for attachment to each other so as to enclose the magnet. One housing element 258 is generally dish-shaped with a rim 260 while the other housing element 262 is generally lid-shaped (as seen in FIG. 26A).

Figure 26B:
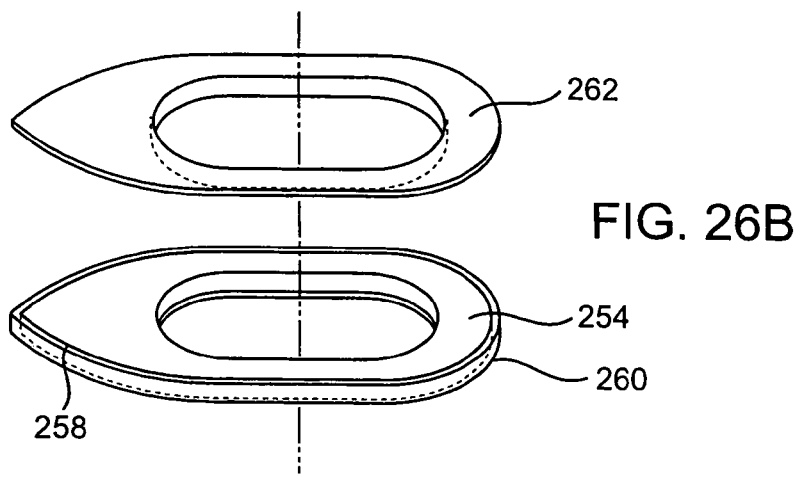
Figure 26C:
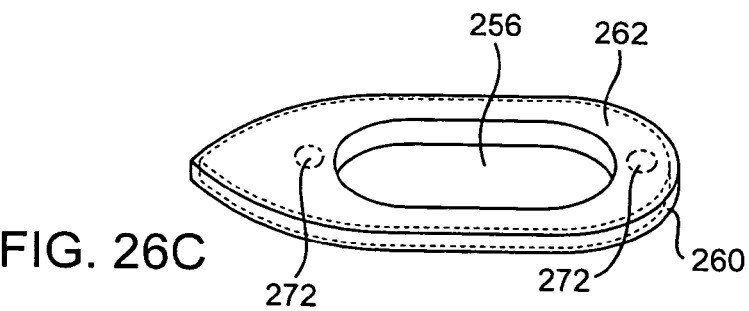
FIG. 26C is an assembled perspective view of the device shown in FIGS. 26A-26B.

FIG. 26B shows the magnetic member 254 disposed in the element 258 with the element 262 positioned above the assembly. FIG. 26C shows the element 262 affixed to the element 254 to form the housing and provide a sealed enclosure containing the magnetic member 254. This enclosure preferably forms a hermetically sealed environment that will protect the member 254 from external elements, e.g., blood or various bodily fluids, upon implanting the device 252 in a patient. The illustrated housing elements 258, 262 may be attached by any suitable means. For example, if constructed of metal laser welding may be used to join the housing elements. Other attachment means include adhesives, fasteners, etc.

Figure 27B:
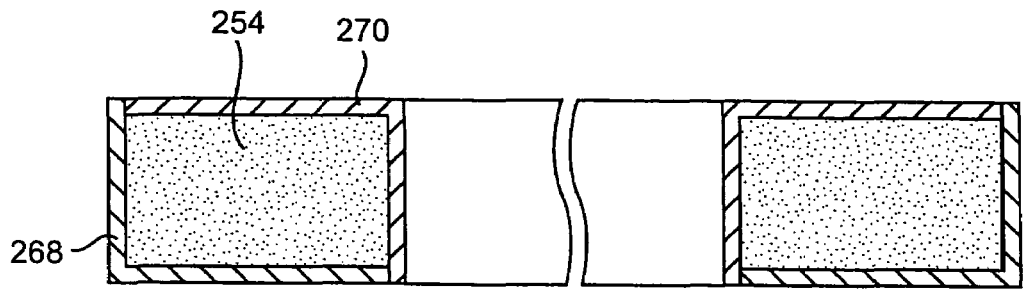
FIGS. 27A-27B are sectional views illustrating alternative constructions of the device shown in FIGS. 26A-26D.
Figure 27A:
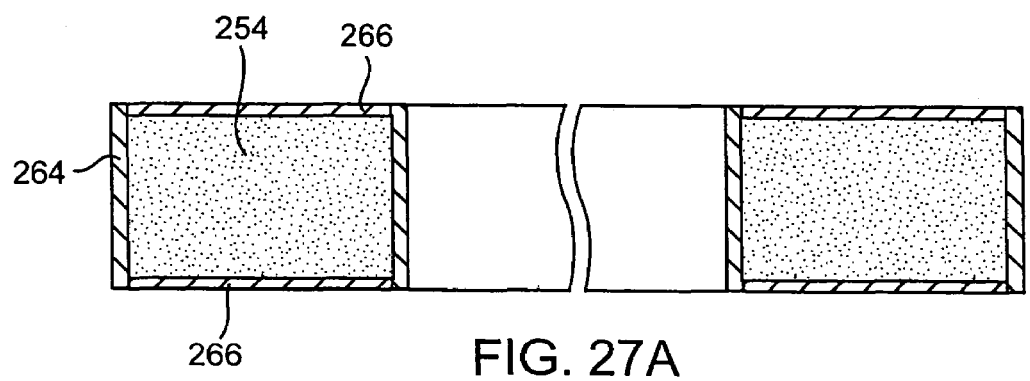
Figure 26D:
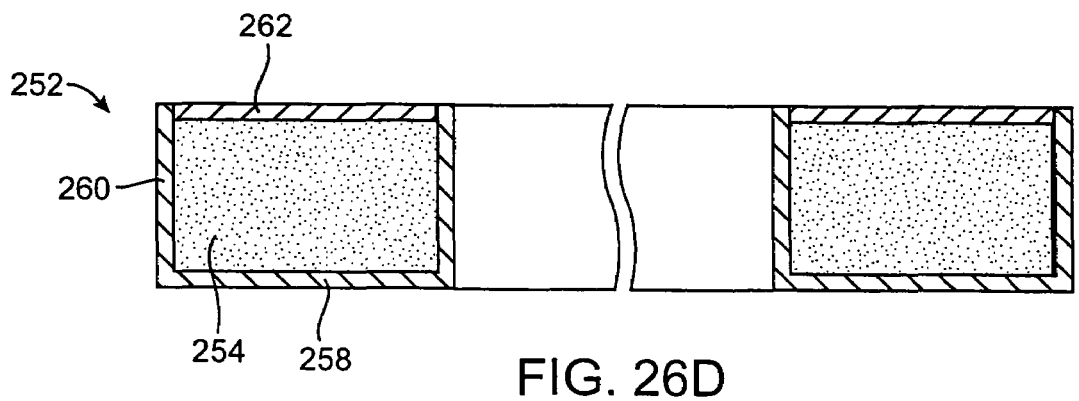
FIG. 26D is a sectional view taken along line D-D in FIG. 26C.

The housing enclosing the magnetic member may of course be formed of a unitary piece of suitable material, for example a metallic blank, or more than two pieces of material joined as described above. FIG. 26D is a sectional view of the device 252 shown in FIG. 26C illustrating the internal construction of the device, with lid element 262 resting on and secured to the rim 260 of dish element. FIG. 27A shows an alternative construction wherein the member 254 is enclosed in a housing defined by a spool-shaped element 264 and a pair of lid-shaped elements 266 secured thereto, for example as described above. FIG. 27B shows yet another construction wherein the member 254 is enclosed in a housing defined by mating channel-shaped elements 268, 270 which are secured together to form the enclosure for the member 254. The housing enclosing the magnetic member is preferably formed of a material that is a good to excellent conductor of magnetic flux. Exemplary materials are discussed above with respect to FIGS. 26A-26C, as well as below in connection with FIGS. 28-31.

FIG. 26C also shows (in phantom) a schematic representation of means for indicating the polarity of the magnetic member 254. The illustrated indicator 272 may take the form of any suitable writing, color, etc., to indicate the polarity of the magnetic field produced by the member 254. For example, the indicator 272 may simply comprise the printed letters "N" or "S." This feature allows a user to confirm proper orientation of the device 252 relative to another device, thereby ensuring that the devices will attract each other (or repel each other, if that is desired). Other possible ways of ensuring proper orientation include pre-mounting the component(s) on a delivery instrument in a selected position, or providing a mechanism that automatically orients the component in the selected position. It may also be desirable to allow the component to be removed and remounted on the delivery device if its orientation is incorrect.

Figure 28:
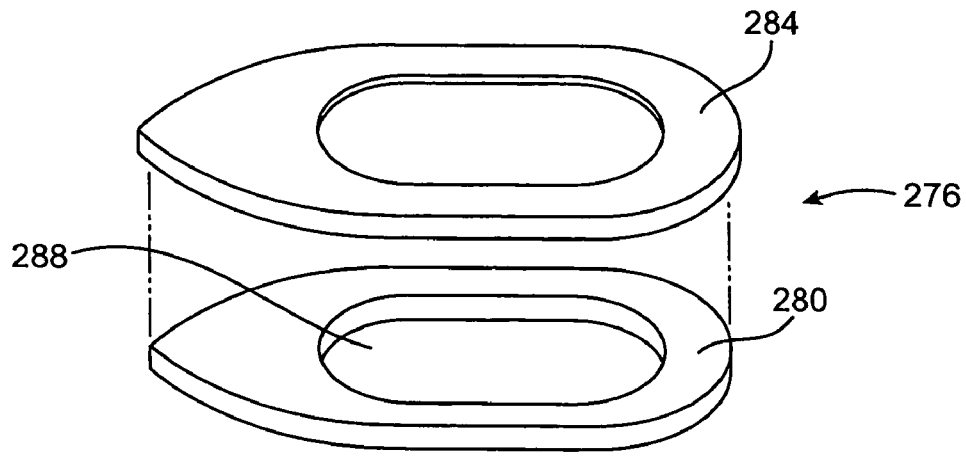
FIG. 28 is an exploded perspective view of two devices which are constructed according to another embodiment of the invention and are adapted to be coupled to tissue using magnetic force for forming a magnetic port in a hollow body having a lumen.
Figure 28:
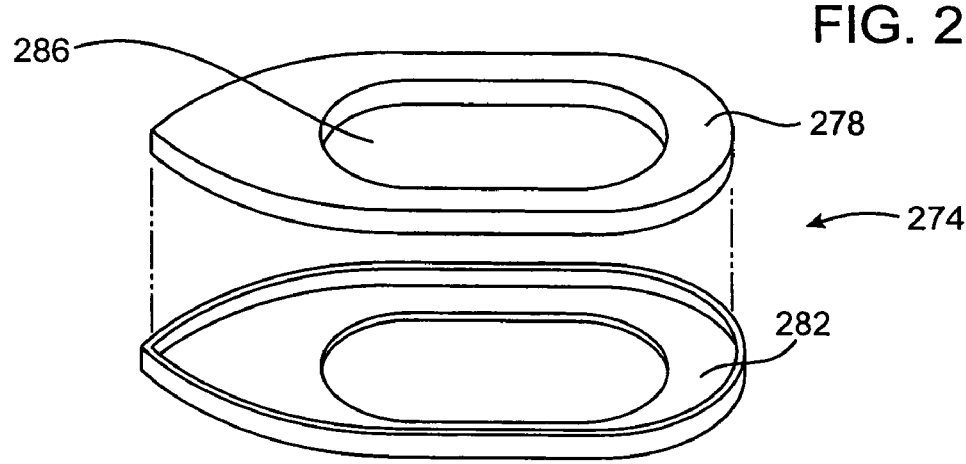

Turning to FIGS. 28-31, another embodiment of the invention will be described and includes methods and devices for increasing the magnetic attracting force between two components. FIG. 28 shows first and second components 274, 276 adapted to be coupled to a target vessel via magnetic attraction. The first and second components 274, 276 comprise, respectively, members 278, 280 which are capable of producing a magnetic field, as well as mechanisms 282, 284 for increasing the magnetic attraction force between the components. That is, when provided with the mechanisms 282, 284 and placed in proximity the components 274, 276 produce a higher magnetic force than when placed in proximity without the mechanisms.

Figure 29:
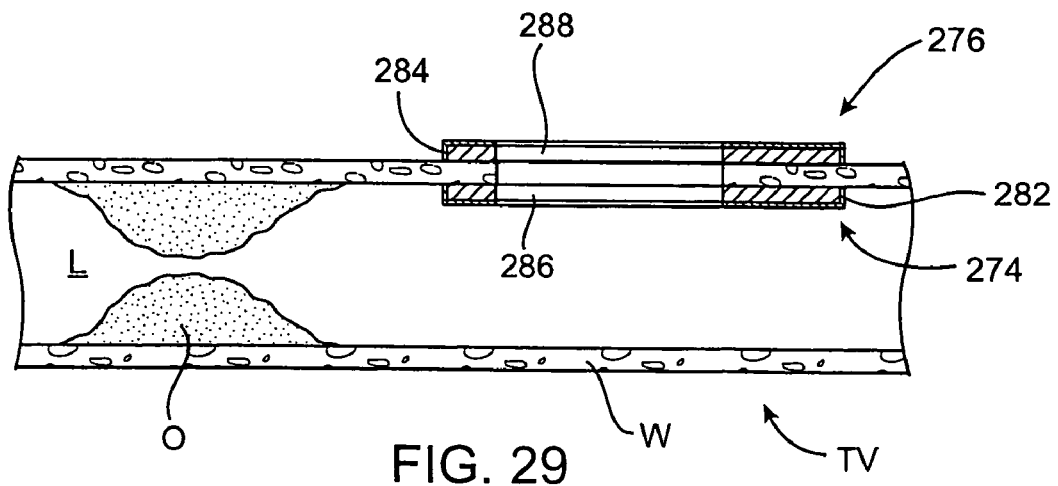
FIG. 29 is a sectional view taken through a vessel having a lumen, wherein the devices shown in FIG. 28 are coupled to the tissue of the vessel wall.

FIG. 29 shows the components 274, 276 positioned on opposite surfaces of the wall W of a target vessel TV and coupled thereto by magnetic force. As shown, in order to form a port that communicates with the vessel lumen L, which is partially occluded at O, the components may have openings, such as respective openings 286, 288 in components 274, 276. These openings preferably are aligned with complementary openings in the mechanisms 282, 284 to form a port extending into the lumen. The mechanisms 282, 284 enhance the magnetic attraction between the components 274, 276, thereby more securely attaching the assembly to the vessel wall W than if the mechanisms were omitted.

Figure 30:
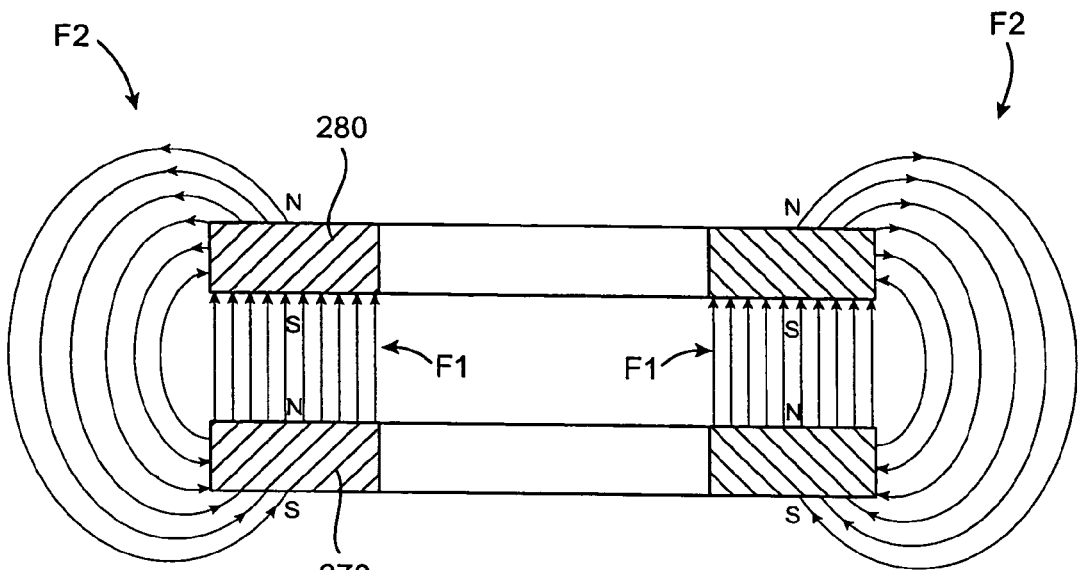
FIG. 30 is a sectional view of two magnets positioned in proximity to each other schematically illustrating the magnetic flux lines associated with the magnets.
Figure 31:
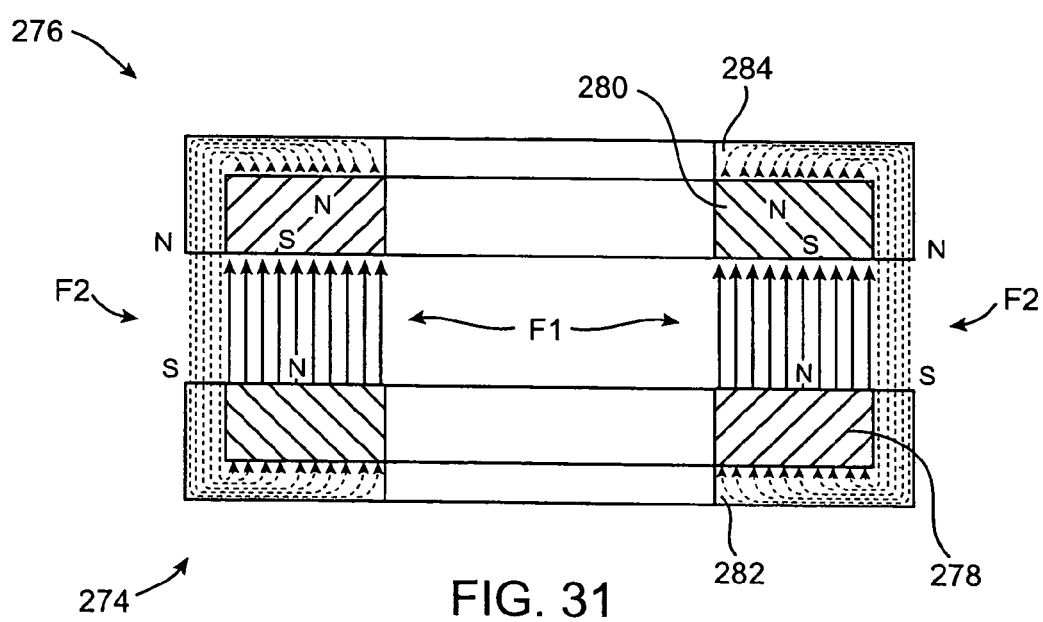
FIG. 31 is a sectional view showing the two magnets of FIG. 30 provided with flux concentration mechanisms constructed according to another embodiment of the invention and schematically illustrating the magnetic flux lines associated with the magnets of the invention.

Referring to FIGS. 30-31, the concept underlying this aspect of the invention will be described with respect to the specific embodiment of FIGS. 28-29. FIG. 30 shows the first and second members 278, 280 (which may be viewed as a pair of permanent bar magnets) in relatively close proximity, the poles of the magnetic members being oriented so that the components attract each other. FIG. 30 also schematically depicts the magnetic field produced by the magnetic members 278, 280. The magnetic field F1 located between the members 278, 280 is essentially uniform given the relatively large surface areas of and the small separation gap between the members. The number of lines present between the members 278, 280 is roughly indicative of the strength of field F1.

As shown, the magnetic field F2 located at the edges of the members 278, 280 fringes out, which dissipates or weakens the field F2. The field F2 fails to significantly increase the attraction force between the members 278, 280 due to its location and the fact that it is relatively weak (as it contains fewer, more spaced apart flux lines than the field F1). Put another way, the magnetic flux density or magnetic induction B (which is a measure of magnetic field strength) of field F1 is greater than the magnetic flux density of field F2. The invention provides means for utilizing the field F2 to increase the magnetic attraction force between two components. It will be noted that for sake of clarity FIG. 30 omits the portion of the magnetic field that would extend inward toward the center of each component.

FIG. 31 shows the members 278, 280 along with the mechanisms 282, 284 in fairly close proximity. The magnetic field F1 located between the members 278, 280 is essentially uniform as described above in connection with FIG. 30. As can be seen, though, the mechanisms 282, 284 alter the location and flux density of the magnetic field F2. Specifically, rather than fringing out as in FIG. 30, the field F2 is concentrated by the mechanisms 282, 284 between the components 274, 276. As such, the magnetic flux density increases, which in turn increases the attracting force between the components.

The specific manner of increasing the magnetic attraction force may vary from that shown. The illustrated mechanisms 282, 284 are configured to alter the construction of the magnetic members 278, 280 in order to increase magnetic flux density and hence raise the attraction force produced thereby. The mechanisms 282, 284 are separate elements coupled to the members 278, 280; however, means for increasing the magnetic force may comprise an integral portion of the magnetic member, a layer or coating applied to the member, etc. Further, the preferred mechanisms are channel-shaped to form an extension of the magnetic member that effectively channels the magnetic field F2 and concentrates the magnetic flux between the components 274, 276 (and more specifically, between the confronting edges of the mechanisms 282, 284). It will, however, be appreciated that this aspect of the invention may be practiced using mechanisms having alternative configurations.

The mechanisms 282, 284 have a magnetic permeability higher than air in order to concentrate the magnetic flux and increase the magnetic flux density and attracting force. That is, the mechanisms provide a path of least resistance as compared to air so that the magnetic flux flows into the mechanisms rather than the air. This in effect forms a magnetic circuit that captures a significant amount of the magnetic field F2 that otherwise would not contribute to the attracting force between the two components. One benefit of this aspect of the invention is that it allows a thinner magnetic member to be used for the component without sacrificing (or even increasing) magnetic field strength. In some applications, such as creating anastomoses on small vessels, it is typically desirable (e.g., for thrombogenecity reasons) to minimize the amount of foreign material located within or against the vascular tissue.

The material used to form the mechanism for increasing magnetic force preferably has a high magnetic permeability μ in order to concentrate a desired amount of magnetic flux in one or more desired areas. The mechanism is preferably formed of ferromagnetic material having a μ that is greater than the μ of air. More preferably, the material has a μ that is greater than 1.0, and even more preferably, significantly greater than 1.0 or as high as possible. Exemplary ranges of μ values include from about 1.0 to about 250,000, and from about 1.0 to about 1000. While ferromagnetic materials are preferably used to form the flux concentration mechanisms, other materials may be used instead. For example, ferrimagnetic, paramagnetic or diamagnetic materials may be used (although the results they achieve may be inferior to those obtained using a ferromagnetic material).

Tests have shown that, depending on the size, material and separation gap of the respective components having magnetic properties, the flux concentration mechanisms of the invention may be used to produce a magnetic attraction force that is from about 5% to about 75% higher than that obtained without flux concentration mechanisms. More preferable, though, is a flux concentration mechanism that increases the force from about 20% to about 75%. The exact amount of magnetic force used in practicing the invention, for example, to secure the components to a vessel, will depend on various factors, such as the sized of the vessel, the force limit prior to causing necrosis, etc.

It will be apparent that this feature of the invention provides ample benefits including a firm attachment to tissue via magnetic force, the ability to alter the construction of a component to customize the amount or location of flux concentration, and the ability to reduce the size of the magnetic component while maintaining sufficient magnetic force to form the anastomosis.

Figure 32A:
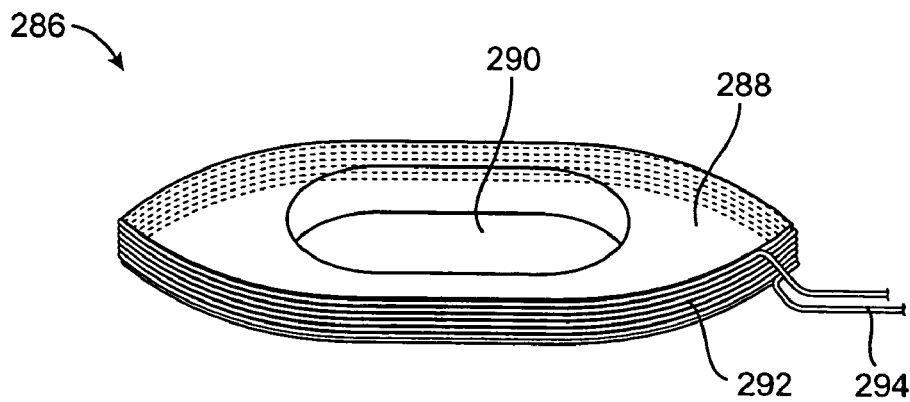
FIG. 32A is a perspective view of a device constructed according to another embodiment of the invention which is adapted to be coupled to tissue using electromagnetic force to form a magnetic port.
Figure 32B:
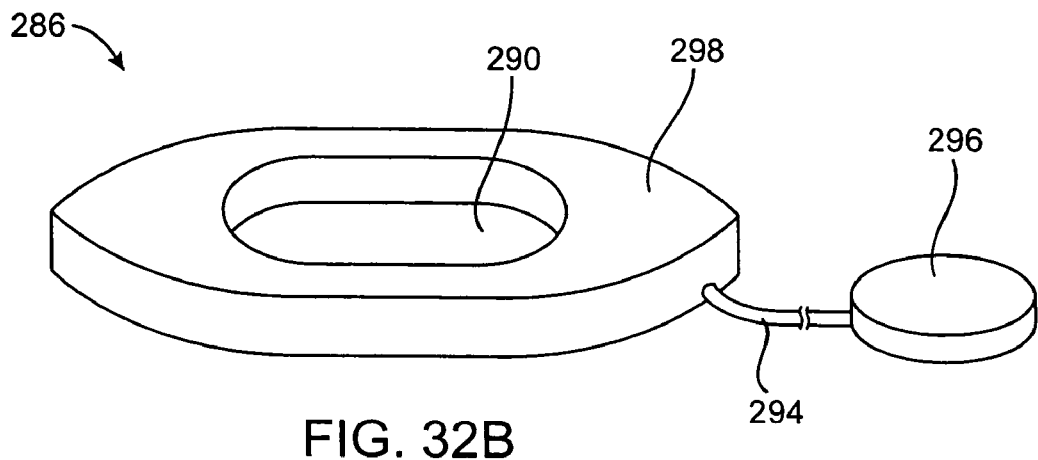
FIG. 32B is a perspective view of the device shown in FIG. 32A enclosed in a protective housing.

FIGS. 32A-32B show an anastomotic component 286 in the form of an electromagnet assembly including a core 288 having an opening 290. A coil 292 is wrapped around the sidewall of the core 288 and has leads 294 running to a power source, such as battery 296 (FIG. 32B). FIG. 32B shows the component 286 after it has been placed in a protective housing 298 by suitable means, for example, a coating or structural enclosure as described above. The housing 296 is preferably formed of a strong, leak-tight biocompatible material.

Figure 33:
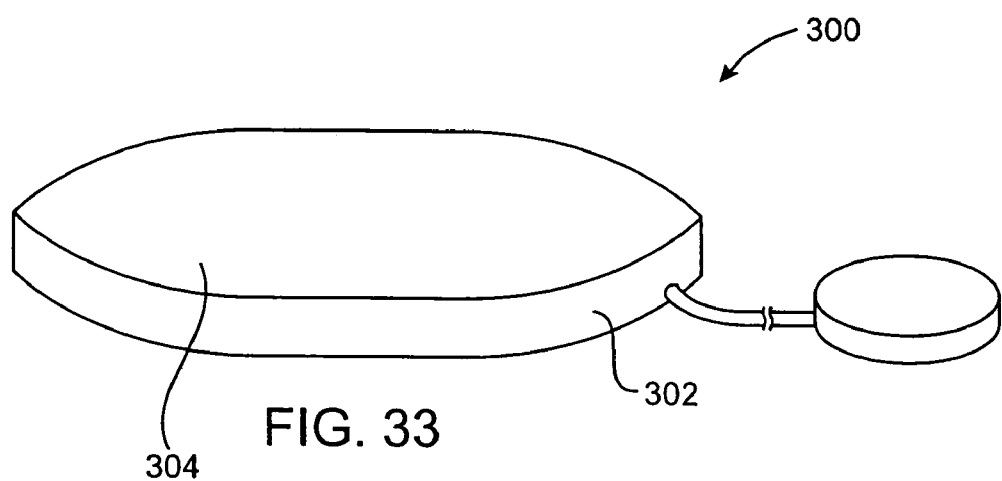
FIG. 33 is a perspective view of a device constructed according to yet another embodiment of the invention which is adapted to close an opening using electromagnetic force.

FIG. 33 shows an electromagnetic component 300 for use in closing an opening, for example, an opening in tissue such as an ASD, VSD, PDA, etc. As can be seen the component 300 includes a housing 302 with at least one occlusion surface 304 adapted to seal against tissue or an anastomotic component.

Figure 34A:
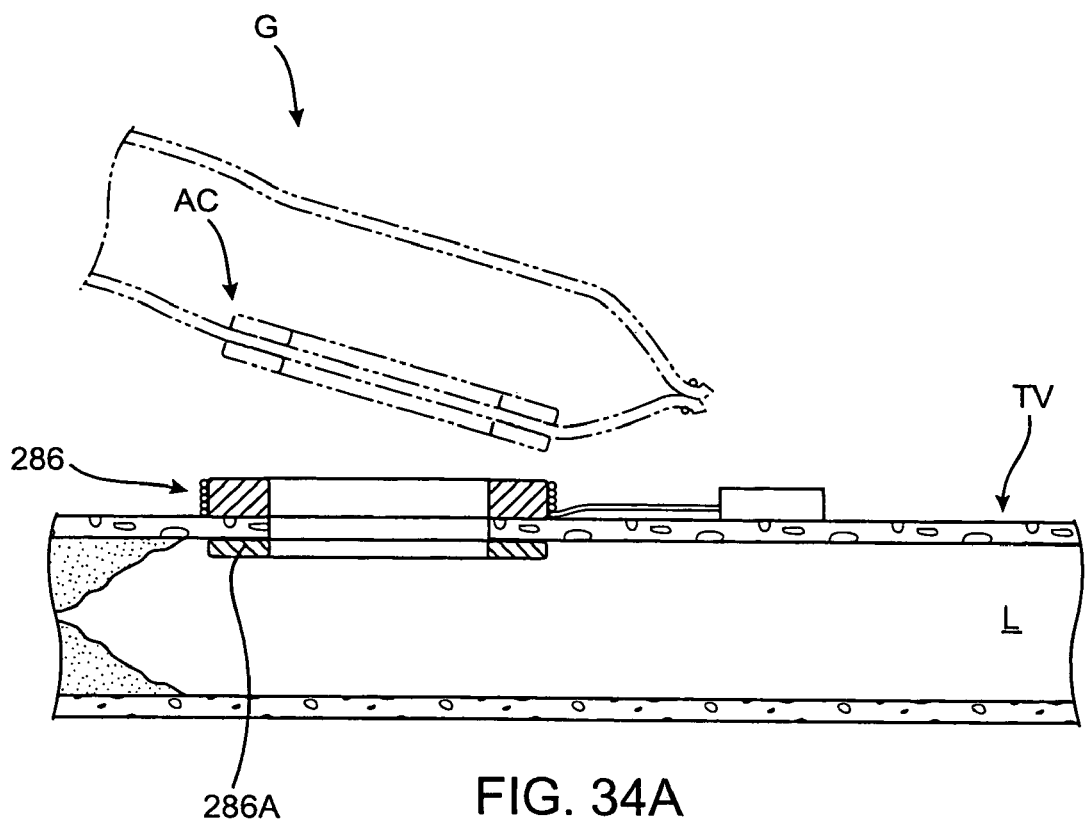
FIG. 34A is a sectional view taken through a target vessel having a lumen showing the device of FIG. 32B coupled thereto with a graft vessel shown (in phantom) prior to being anastomosed to the device.
Figure 34B:
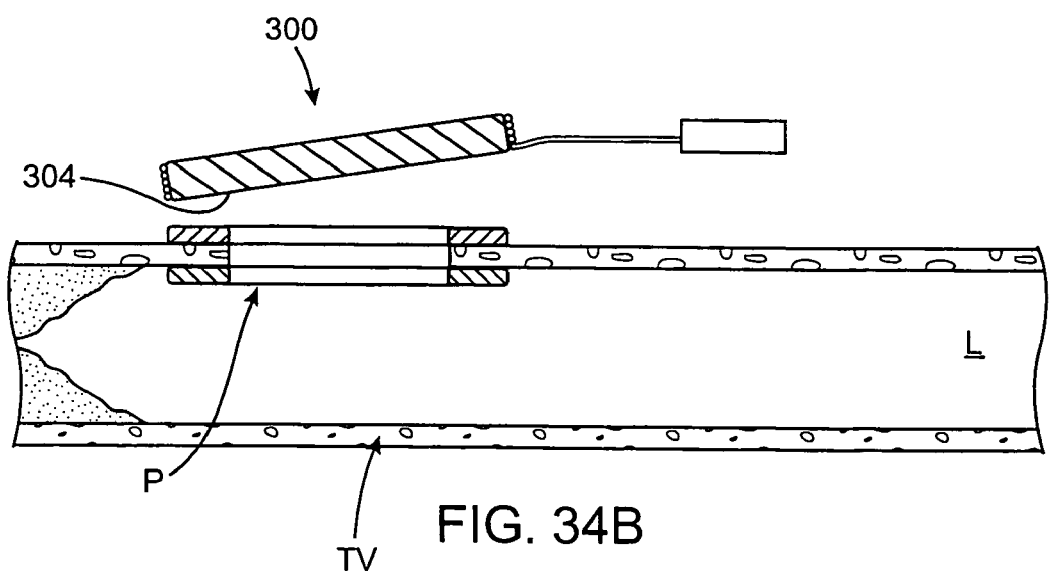
FIG. 34B is a sectional view taken through a target vessel having a port defined by an anastomotic component communicating with the vessel lumen with the device of FIG. 33 positioned above the port prior to being used to close the opening.

FIG. 34A is an example of the component 286 coupled to an anastomotic component 286A positioned on the opposite surface of the of a target vessel TV with a lumen L. A graft vessel G is shown (in phantom) just above the component 286 and includes an anastomotic component AC oriented to magnetically attract (or be attracted to) the electromagnetic assembly of component 286. FIG. 34B shows the occluding surface 304 of component 300 being used to close, either temporarily or permanently, a magnetic port P which communicates with the lumen L of the target vessel TV.

Figure 35A:
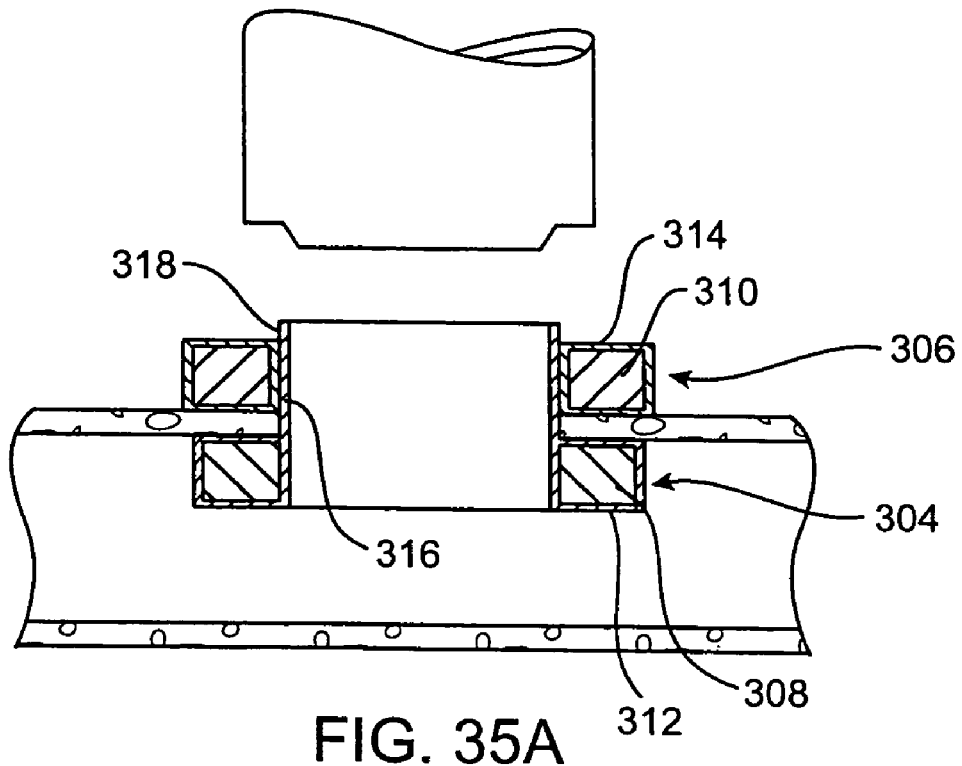
FIGS. 35A-35B are sequential sectional views taken through a target vessel having a lumen showing an anastomotic component constructed according to another embodiment of the invention being coupled to the wall of the vessel.
Figure 35B:
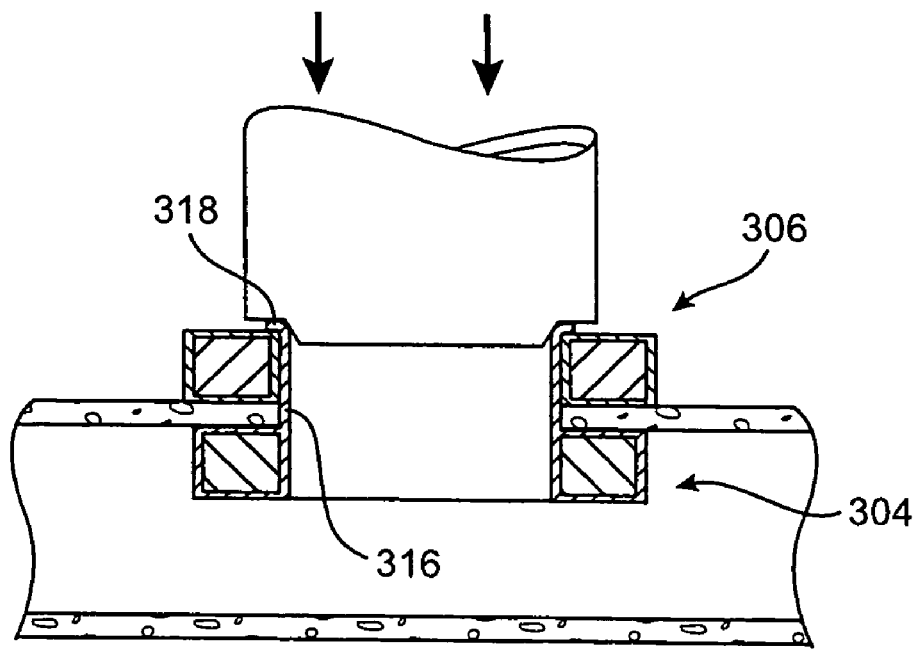
Figure 36A:
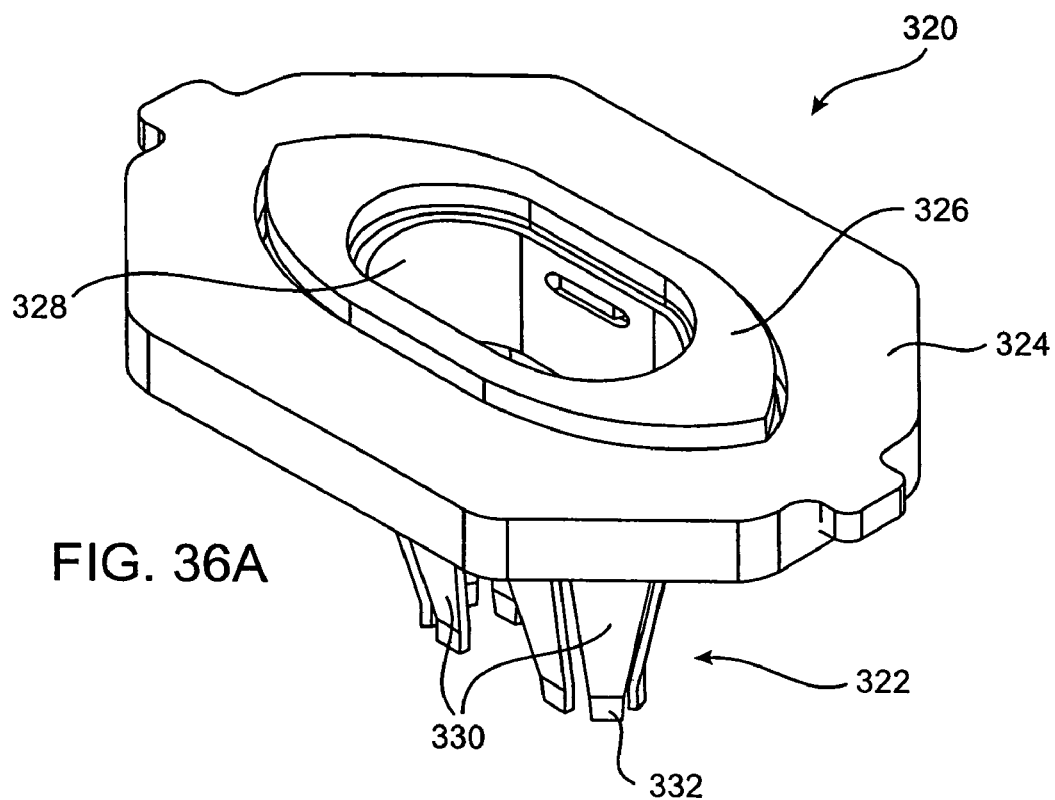
FIGS. 36A-36B are, respectively, upper and lower perspective views of a device constructed according to another embodiment of the invention for forming a port in a vessel having a lumen, wherein the device has a mechanical attachment portion shown in a low profile or collapsed orientation.
Figure 36B:
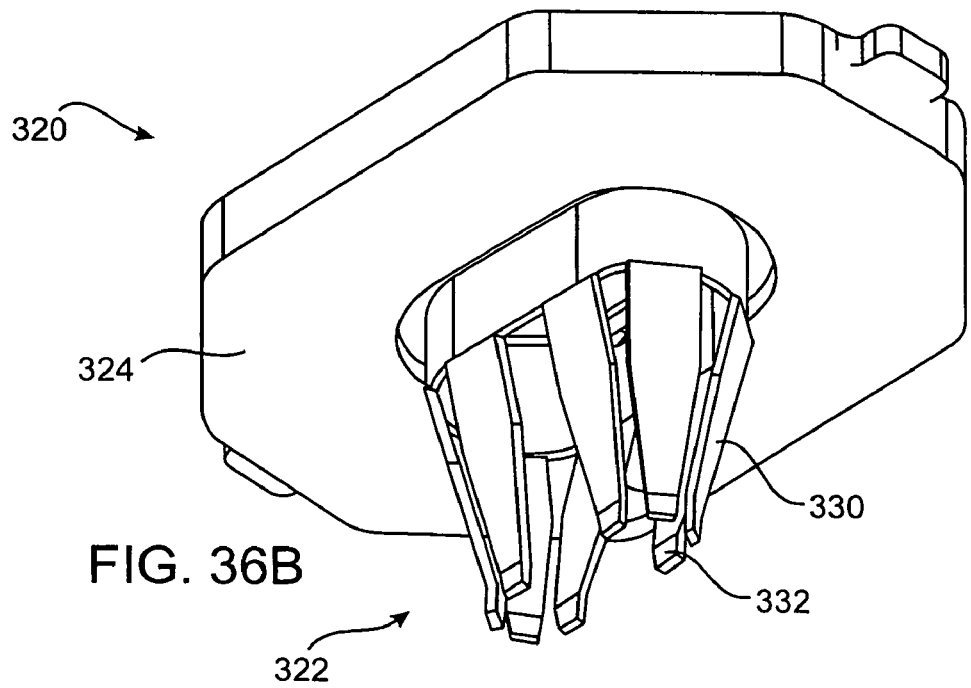
Figure 37A:
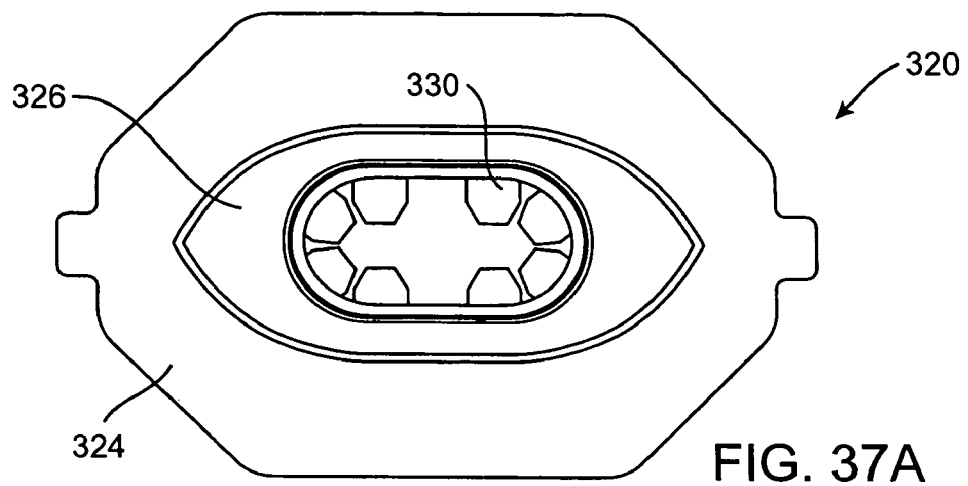
FIGS. 37A-37C are, respectively, upper plan, side elevation, and lower plan views of the device shown in FIGS. 36A-36B.
Figure 37B:
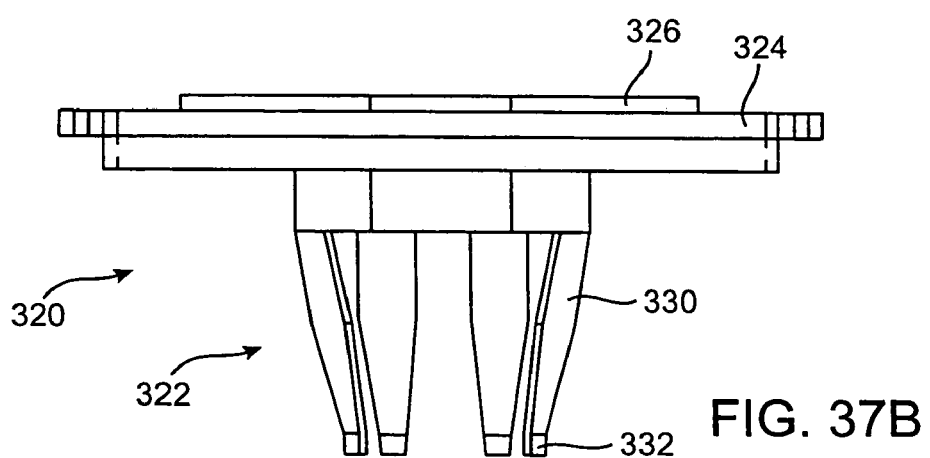
Figure 37C:
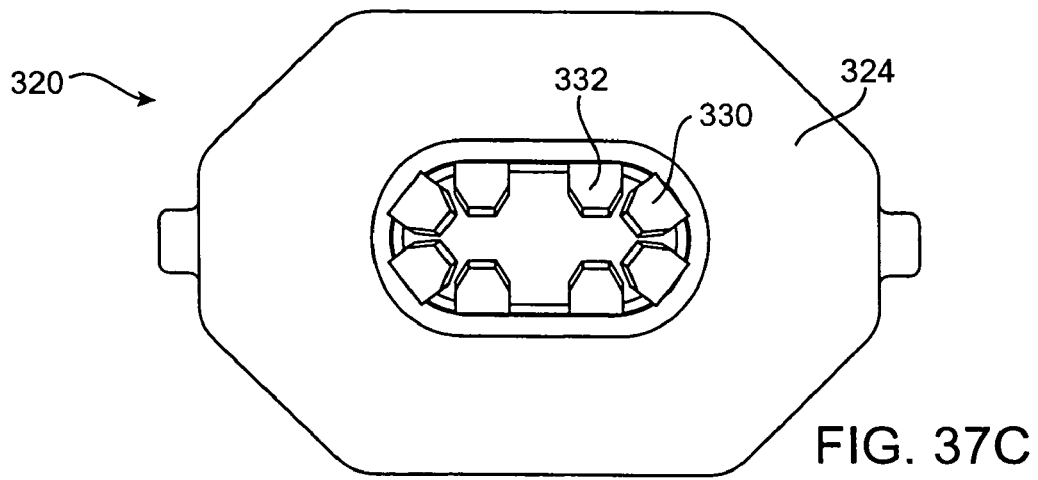
Figure 38A:
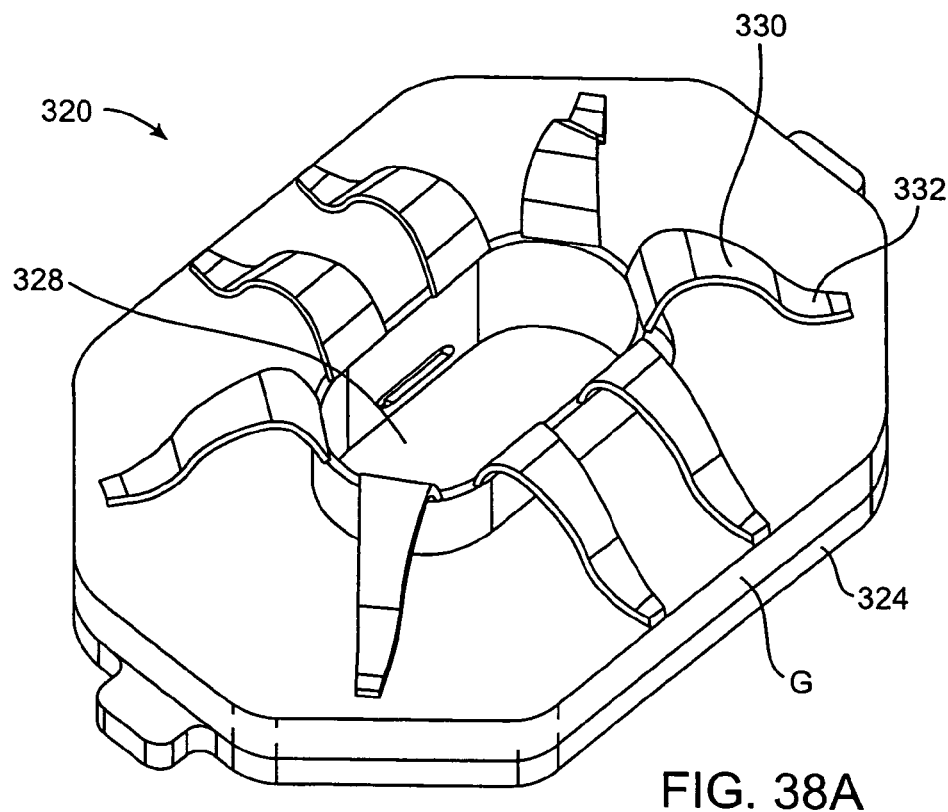
FIGS. 38A-38B are, respectively, upper and lower perspective views of the device shown in FIGS. 36A-36B, wherein the mechanical attachment portion of the device is shown in a wide profile or expanded orientation.
Figure 38B:
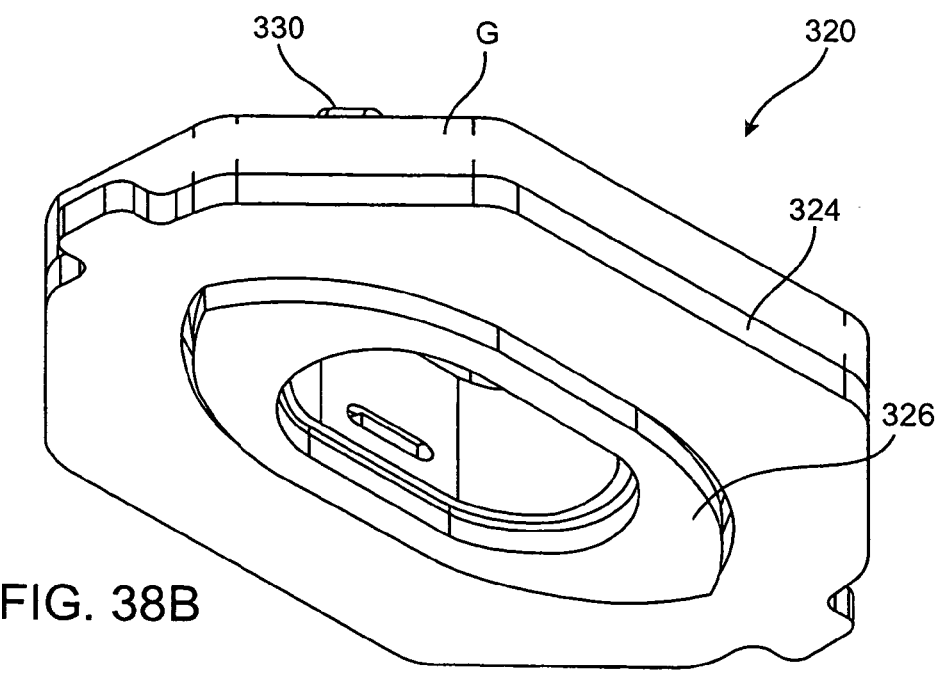

The invention may be practiced using magnetic, mechanical, or any other force-creating means to secure a component to tissue or to another component. FIG. 35A shows two anastomotic components 304, 306 including first and second magnetic members 308, 310 enclosed in housings 312, 314. The first component 304 has a sleeve portion 316 (which in FIG. 35A is an extension of the housing 314) having an end 318 that projects beyond the second component 306. Any suitable means may be used to collapse or other manipulate the end 318 relative housing 314 of second component 306, for example, the instrument represented schematically in FIG. 35A. As shown in FIG. 35B, the instrument is moved in the direction of the arrows to collapse the end 318 and mechanically couple the securing components 304, 206. As a result, this embodiment joins the components by both magnetic and mechanical forces.

FIGS. 36A-39C show another embodiment in the form of a component 320 to be coupled to tissue by a mechanical attachment portion 322. The component 320 includes a base 324 and a member 326 for producing a magnetic field. An opening 328 passes through the component 320 and is placed in communication with a target vessel, for example, a coronary or peripheral artery. FIGS. 36A-36B and 37A-37C show the component 320 in a low profile or collapsed configuration for delivery. The illustrated attachment portion 322 includes a plurality of arms 330 adapted to engage tissue of the target vessel wall, which results in the vessel wall being sandwiched between the ends 332 of the arms 330 and the base 324. The component 320 may comprise separate members, as in the illustrated embodiment, or it may comprise an integral structure with or without a magnetic portion.

Figure 39A:
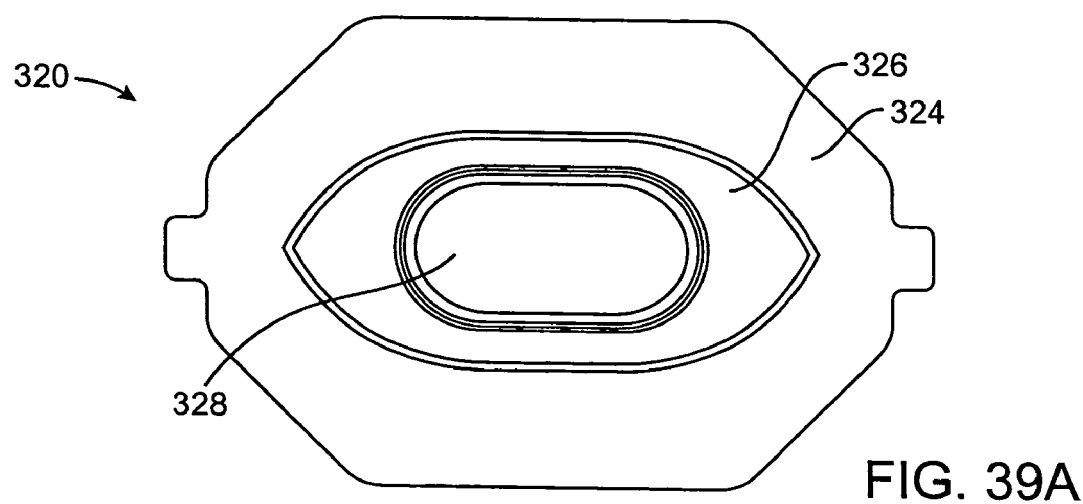
FIGS. 39A-39C are, respectively, upper plan, side elevation, and lower plan views of the device as shown in FIGS. 38A-38B.
Figure 39B:
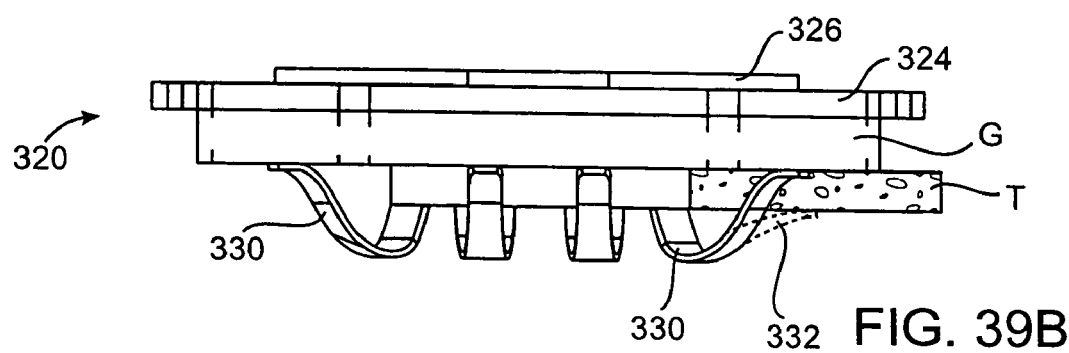
Figure 39C:
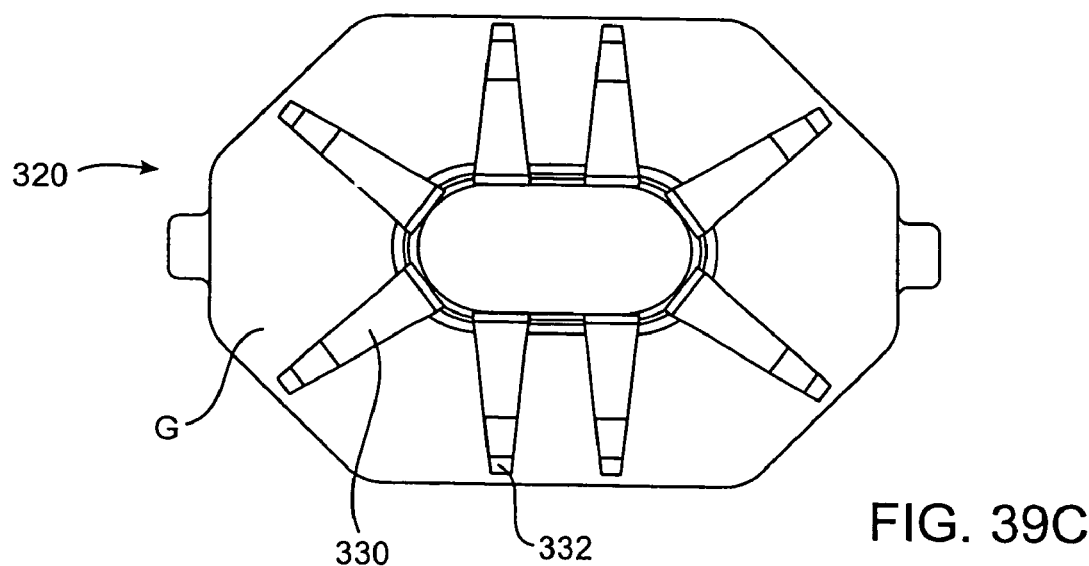

FIGS. 38A-38B and 39A-39C show the component 320 in a raised profile or expanded configuration corresponding to its deployed, tissue-engaging position. FIG. 39B shows (in phantom) tissue T engaged by the expanded arm 332. These Figures show, however, an optional feature of this embodiment, namely, a biocompatible layer G adapted to be placed in contact with the tissue. Exemplary uses for such as layer, which may be formed of any suitable material, include sealing the vessel opening and promoting tissue ingrowth at the site. This embodiment of the invention uses mechanical force to couple a component to the tissue but forms a magnetic port (via member 326) that may be anastomosed to another component having the same or a different construction. It will be recognized that the component 320, rather than presenting a magnetic port for docking a vessel, could present an alternative structure for attaching a graft, such as a stent, staples or fasteners, adhesive, etc.

FIGS. 40A-40C shows an exemplary use of the device illustrated in FIGS. 36A-39C. A delivery device 334 is schematically shown and includes a tip 336 which is preferably configured to incise and dilate tissue. The tip 336 may be mounted on a shaft 338 and has a recess that receives the ends 332 of the arms 330 (FIG. 40A) and retains them in their collapsed configuration. The delivery device 334 also has an end 340 for contacting the magnetic member 326 of the component 320 to prevent movement of the arms 330 relative to the delivery device.

FIG. 40A shows the device 334 after the tip 336 has cut through tissue of a vessel wall W and the component has been properly positioned against the surface of the wall. FIG. 40B shows the device 334 after the shaft 338 has been moved distally to release the ends 332 of component arms 330 and allow them to expand into contact with the tissue T. Next, as shown in FIG. 40C, the delivery device 334 with shaft 338 is removed proximally through the opening 328 of component 320.

It will of course be appreciated that this embodiment of the invention may take many constructions other than those specifically illustrated herein. For example, rather than having individual arms 330 which engage the tissue T, a continuous or semi-continuous surface could be used, the surface being planar, concave-convex, etc.

Figure 41A:
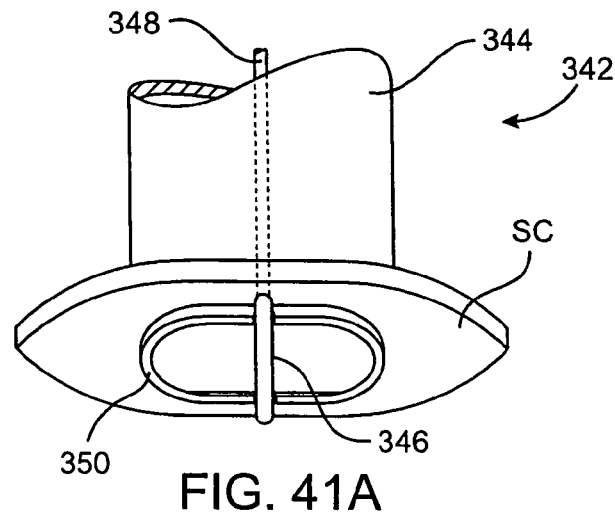
FIG. 41A is a perspective view of a delivery device constructed according to another embodiment of the invention, wherein the device has a retaining portion shown in a first position to retain an anastomotic component.
Figures 41B, 41C:
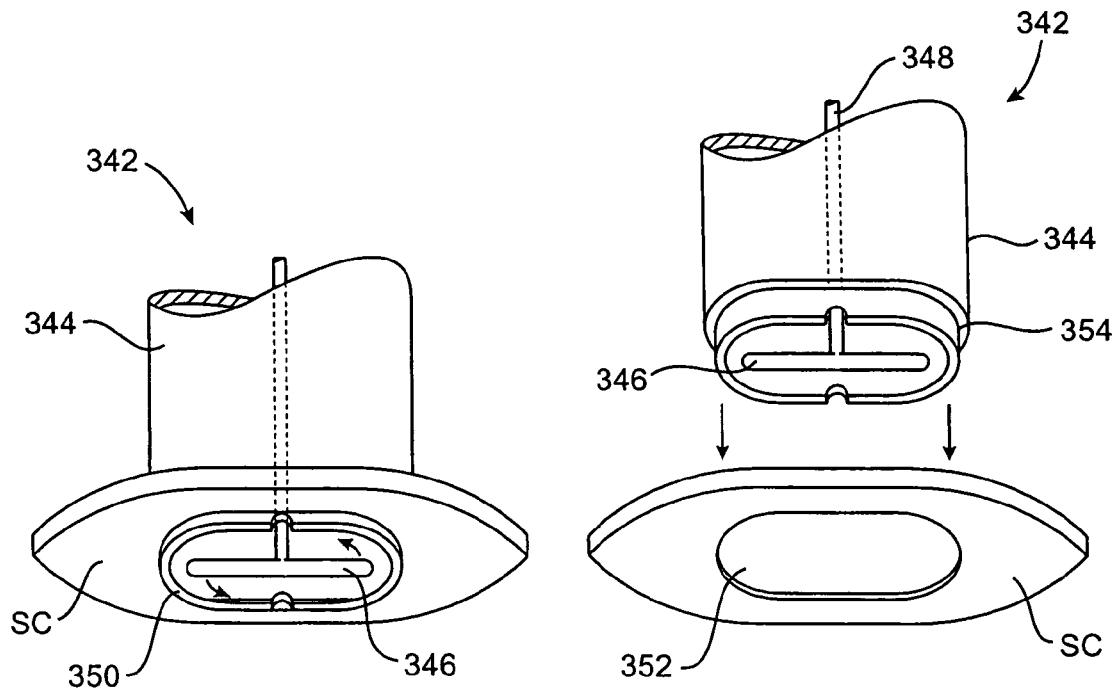
FIGS. 41B-41C are perspective views of the device shown in FIG. 41A but sequentially illustrating the retaining portion being moved to release the component.

FIGS. 41A-41C show a delivery device constructed according to yet another embodiment of the invention. The delivery device 342 includes a support portion 344 and a retaining portion or mechanism 346 for retaining a securing component SC on the device. The illustrated retaining portion 346 is carried by a shaft 348 and engages a flange 350 formed on (or attached to) the securing component SC around its opening 352. The flanged securing component SC is preferably magnetic and may be constructed as described above regarding previous embodiments (e.g., FIGS. 19A-19C). FIG. 41A shows the delivery device 342 in a first position in which the retaining portion 346 is in its first position to retain the securing component SC. It will be noted that the device 342 may also be used to deliver a non-flanged securing component(s).

FIG. 41B shows the delivery device 342 after the retaining portion 346 has been moved out of the first position to release the securing component 342. In this embodiment the retaining portion is rotated 90° from the first position, although other motions may be used to release and engage the securing component. FIG. 41C shows the delivery device 342 after it has been withdrawn proximally through the opening 352 in the securing component 342. FIG. 41C also shows the particular construction of the support portion 344 of device 342. A step 354 is formed to receive the opening 352 of the securing component 342. The step 354 helps align the securing component and aids in even delivery to the tissue surface.

Figure 42A:
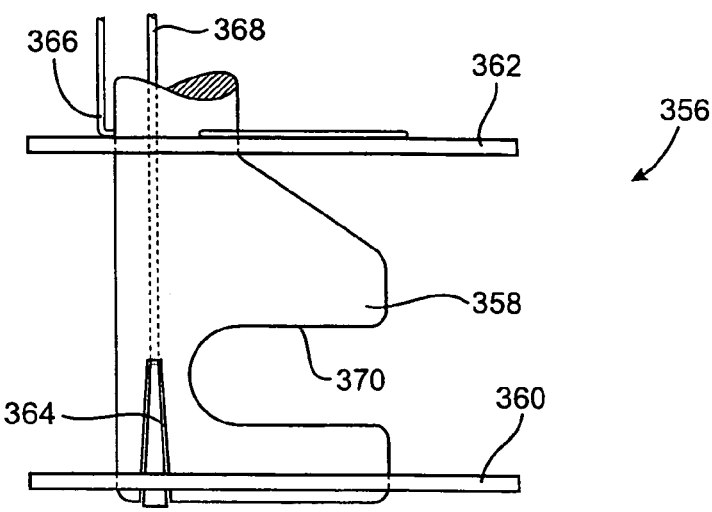
FIG. 42A is a perspective view of a delivery device constructed according to still another embodiment of the invention, wherein the device has a retaining portion shown in a first position to retain an anastomotic component.
Figure 42B:
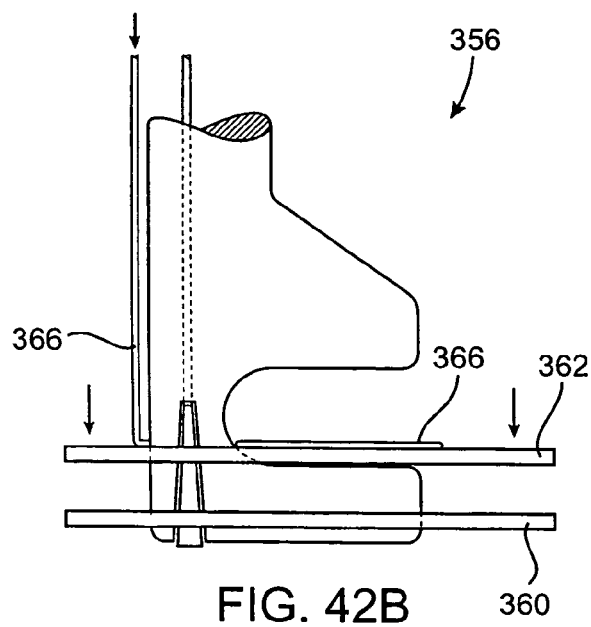
FIGS. 42B-42C are perspective views of the device shown in FIG. 42A sequentially illustrating the retaining portion being moved to release the component.
Figure 42C:
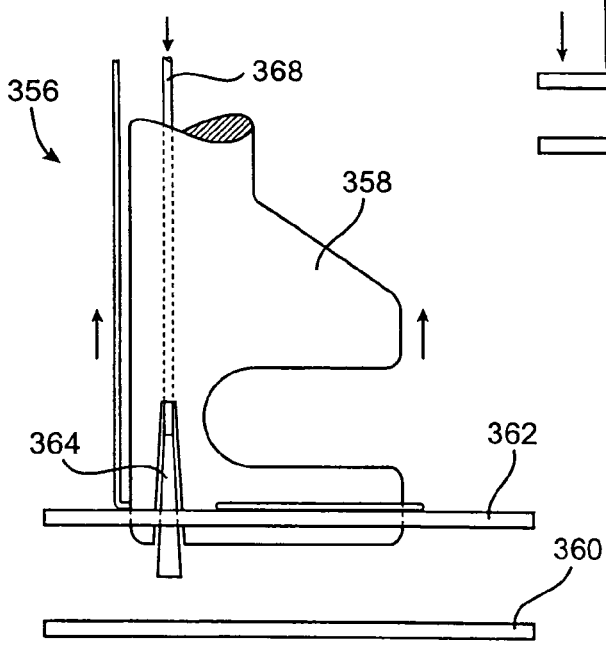

FIGS. 42A-42C show a delivery device 356 constructed according to yet another embodiment of the invention. The device 356 includes a body 358 which to some extent acts as a support portion for first and second components 360, 362. A first retaining portion or mechanism 364 is movable relative to the body 358 and engages the first component 360 to retain it in place prior to and during delivery. A second retaining portion or mechanism 366 is also movable and engages the second component 362 to retain it in place. A shaft 368 supports the first retaining portion 364, and the body 358 has a notch 370 which facilitates introducing the components into a vessel lumen, as described below.

FIG. 42B shows the device 356 after the second retaining portion 366 has been moved toward first component 360 to drive the second component 362 to its desired position, for example, against an opposite surface of the vessel wall. FIG. 42C shows the device 356 after the first retaining portion 364 has been moved distally relative to the body 358 of the device. The portion 364 is wedge-shaped and this motion moves the portion 364 out of contact with the first component 360, thereby releasing it from the device. Magnetic attraction maintains the two components 360, 362 in place.

Figure 43A:
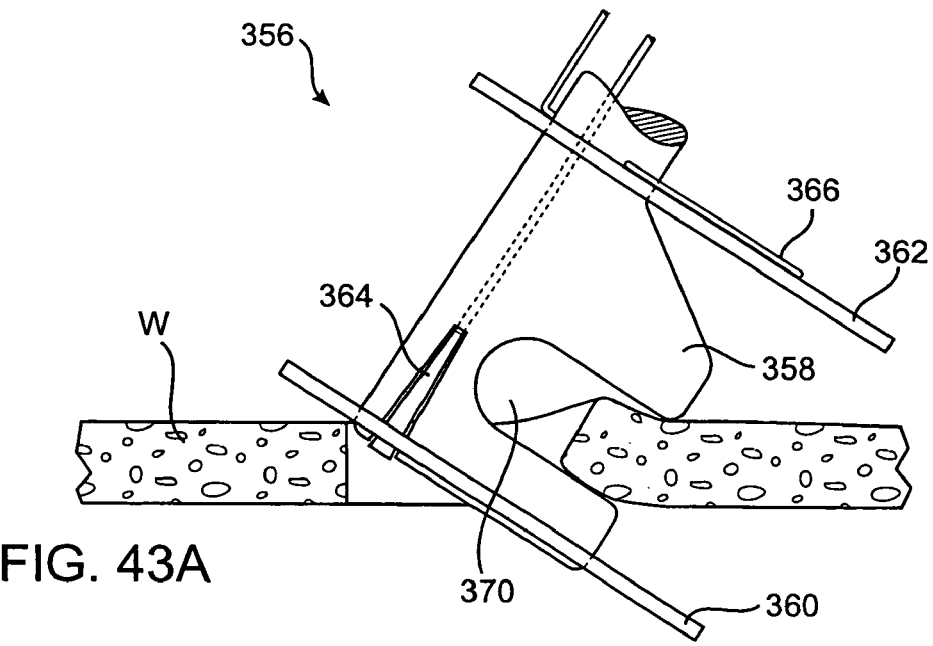
FIGS. 43A-43B are partial sectional views of the device shown in FIGS. 42A-42C sequentially illustrating the device being used to couple an anastomotic component to a vessel.
Figure 43B:
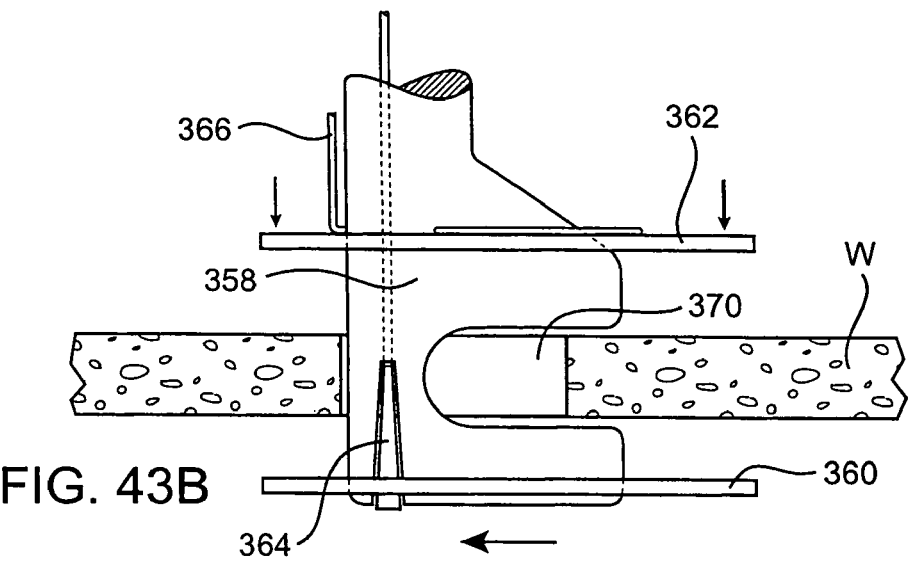
Figure 43C:
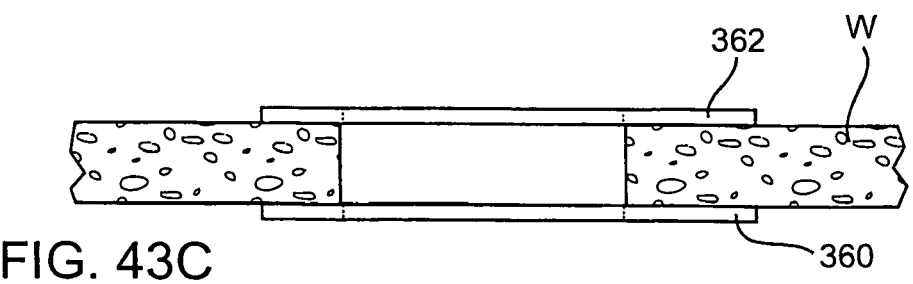
FIG. 43C is a partial sectional view showing the anastomotic component in its final position.

FIGS. 43A-43C show the delivery device 356 being used to couple the first and second components 360, 362 to a vessel wall W. As shown in FIG. 43A, the notch 370 can be used to guide the first component 360 through an incision in the wall W. It should be noted now that another aspect of this embodiment provides an offset structure for easier introduction of the leading end of a component. As can be seen in FIG. 43A, this feature allows the longer component 360 to be introduced through a shorter incision. The term offset means that the body 358, i.e., the delivery end of the device 356, extends laterally in one direction to give the device an asymmetrical configuration. For example, in the illustrated embodiment the body 358 extends to one side and defines the notch 370, but does not extend laterally in the opposite direction. Put another way, the delivery end of the device 356 is offset with respect to a longitudinal axis of the device.

FIG. 43B show the first component 360 passed through the incision and the second component 362 being lowered to a position that achieves the desired amount of magnetic attracting force. FIG. 43C shows the resulting position of the two components with their openings generally aligned with the incision in the wall W.

Figure 44:
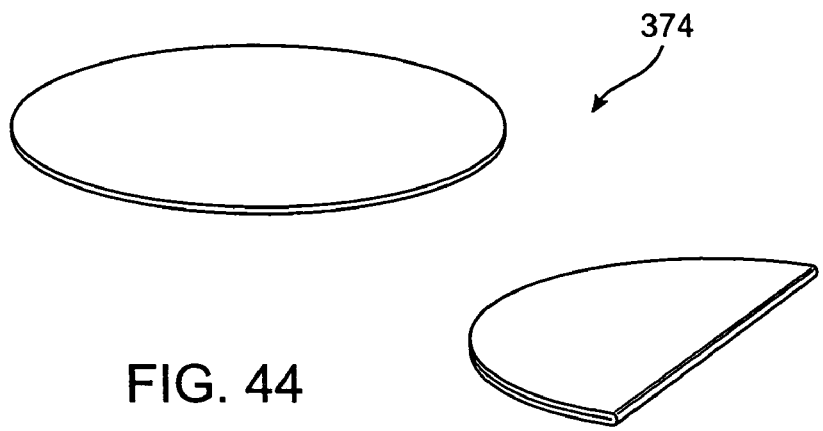
FIG. 44 is a perspective view sequentially showing a flexible magnetic component constructed according to one embodiment of the invention being collapsed.
Figure 45A:
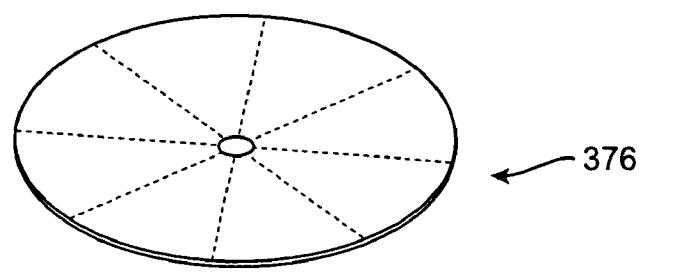
FIGS. 45A-45B are perspective views illustrating a flexible magnetic component constructed according to one embodiment of the invention in its expanded and collapsed orientations, respectively.
Figure 45B:
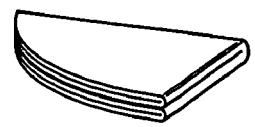
Figure 45B:
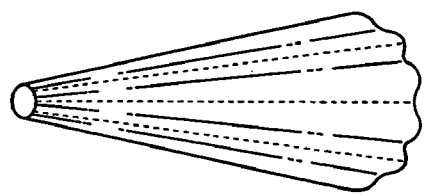

As mentioned above with respect to FIG. 5, the invention may be practiced using flexible components that are capable of producing a magnetic field. FIG. 44 shows another embodiment comprising a component 374 in the form of a foldable sheet being collapsed, for example, in order to deliver the component percutaneously. FIGS. 45A-45B show, respectively, expanded and collapsed orientations of a component 376 constructed according to another embodiment. FIGS. 46A-46B show, respectively, components 378, 380 having magnets 382 disposed partially therein so as to allow at least partial collapsing of the components in accordance with yet another embodiment.

FIG. 46C shows a component 384 constructed according to another embodiment in its expanded state. A frame 386 supports a web or body 388 and is capable of producing a magnetic field while being collapsible for easier delivery. The web 388 may be used to occlude an opening. FIG. 46D shows a collapsible component 390 that may be used to form a magnetic port or an anastomosis. The component 390 preferably comprises a magnetic core covered by a superelastic or shape memory housing and has ends 392 that permit the component to be delivered in a straight, low-profile configuration. FIG. 46E shows an exemplary catheter C retaining the component 390 in a low-profile orientation.

FIGS. 47A-47C show yet another embodiment of the invention that provides a device 394 for closing an opening in tissue, such as any of the cardiovascular defects mentioned above. The device 394 could be used in other applications as well. In FIG. 47A a sheath or catheter 396 houses a pair of magnetic components 398, 400 on a shaft 402. The components 398, 400 may take any of the previously described constructions and are configured to attract each other across a body of tissue with an opening to be closed. FIG. 47B shows the device 394 after relative movement has been imparted to the sheath 396 and the components 398, 400. The component 398 is out of the sheath 396 and fully expanded while the component 400 is partially out of the sheath and expanded. FIG. 47C shows the device 394 with the component 398 exploded from the shaft 402. The shaft 402 and component 398 have mating magnetic and/or mechanical interlocking means indicated at 404, such means securely holding the component 398 during delivery and then releasing it preferably via remote actuation upon reaching the target site.

FIGS. 48A-48C show an exemplary application of the embodiment illustrated in FIGS. 47A-47C wherein the device 394 is used to close a ventricular septal defect VSD in the septum S between the right and left ventricles RV, LV. FIG. 48 shows the device 394 introduced percutaneously into the right ventricle RV and the component 398 located and expanded in the left ventricle LV. The component 398 is forced against the septum S and the other component 400 is expanded as shown in FIG. 48B. Once expanded, component 400 is forced against the septum S (e.g., by using the sheath 396), attracts the component 398 to close the defect, and the device 394 is removed (FIG. 48C).

The preferred embodiments of the invention are described above in detail for the purpose of setting forth a complete disclosure and for sake of explanation and clarity. It will be readily understood that the scope of the invention defined by the appended claims will encompass numerous changes and modifications.

What is claimed is:

1. A method for forming a magnetic port in a first hollow body located within a patient, the first hollow body having a lumen, the method comprising steps of:
   (a) forming an opening in a wall of the first hollow body, the opening extending into the lumen of the first hollow body;
   (b) providing a first securing component that produces a magnetic field and having an opening adapted to be placed in communication with the opening in the wall of the first hollow body:
   (c) coupling the first securing component to the first hollow body by a mechanical attachment to form a magnetic port in the first hollow body, the mechanical attachment having an expandable structure, introducing the expandable structure in a collapsed condition through the opening in the wall of the first hollow body and expanding the expandable structure to engage the wall of the first hollow body;
   wherein the expandable structure comprises a plurality of arms that are generally coplanar for contacting the wall of the first hollow body when the arms are expanded; and wherein the arms are self-expanding.

2. The method of claim 1, wherein the first securing component is coupled to the first hollow body solely by a mechanical attachment.

3. The method of claim 1, further comprising the steps of providing a second securing component capable of producing or being attracted by a magnetic field, joining the second securing component to a second hollow body, and magnetically coupling the second securing component to the magnetic port created according to step (c) to form an end-to-side anastomosis between the first and second hollow bodies.

4. The method of claim 1, further comprising the steps of:
   (d) forming an opening in a wall of a second hollow body, the opening extending into the lumen of the second hollow body;
   (e) providing a second securing component capable of producing a magnetic field and having an opening adapted to be placed in communication with the opening in the wall of the second hollow body;
   (f) coupling the second securing component to the second hollow body by a mechanical attachment to form a magnetic port in the second hollow body, the mechanical attachment having an expandable structure, introducing the expandable structure in a collapsed condition through the opening in the wall of the second hollow body and expanding the expandable structure to engage the wall of the second hollow body; and
   (g) magnetically coupling the second securing component to the first securing component to form a side-to-side anastomosis between the first and second hollow bodies.

5. The method of claim 4, wherein the expandable structure of the first securing component comprises a plurality of arms that are generally coplanar for contacting the wall of the first hollow body when the arms are expanded and the expandable structure of the second securing component comprises a plurality of arms that are generally coplanar for contacting the wall of the second hollow body when the arms are expanded.

6. The method of claim 4, wherein the first securing component has a laminated structure and includes a layer of biocompatible material to enhance sealing of the opening in the wall of the first hollow body.

7. The method of claim 4, wherein the second securing component has a laminated structure and includes a layer of biocompatible material to enhance sealing of the opening in the wall of the second hollow body.

8. A method for forming a magnetic port in a first hollow body located within a patient, the first hollow body having a lumen, the method comprising steps of:
   (a) forming an opening in a wall of the first hollow body, the opening extending into the lumen of the first hollow body;
   (b) providing a first securing component capable of producing a magnetic field and having an opening adapted to be placed in communication with the opening in the wall of the first hollow body;
   (c) coupling the first securing component to the first hollow body by a mechanical attachment to form a magnetic port in the first hollow body, the mechanical attachment having an expandable structure, introducing the expandable structure in a collapsed condition through the opening in the wall of the first hollow body and expanding the expandable structure to engage the wall of the first hollow body;
   (d) forming an opening in a wall of a second hollow body, the opening extending into the lumen of the second hollow body;
   (e) providing a second securing component capable of producing a magnetic field and having an opening adapted to be placed in communication with the opening in the wall of the second hollow body;

(f) coupling the second securing component to the second hollow body by a mechanical attachment to form a magnetic port in the second hollow body, the mechanical attachment having an expandable structure, introducing the expandable structure in a collapsed condition through the opening in the wall of the second hollow body and expanding the expandable structure to engage the wall of the second hollow body; and (g) magnetically coupling the second securing component to the first securing component to form a side-to-side anastomosis between the first and second hollow bodies;

wherein the expandable structure of the first securing component comprises a plurality of arms that are generally coplanar for contacting the wall of the first hollow body when the arms are expanded and the expandable structure of the second securing component comprises a plurality of arms that are generally coplanar for contacting the wall of the second hollow body when the arms are expanded; and wherein the arms are self-expanding.

9. A method for forming a magnetic port in a first hollow body located within a patient, the first hollow body having a lumen, the method comprising steps of:

(a) forming an opening in a wall of the first hollow body, the opening extending into the lumen of the first hollow body;

(b) providing a first securing component that produces a magnetic field and having an opening adapted to be placed in communication with the opening in the wall of the first hollow body;

(c) coupling the first securing component to the first hollow body by a mechanical attachment to form a magnetic port in the first hollow body, the mechanical attachment having an expandable structure, introducing the expandable structure in a collapsed condition through the opening in the wall of the first hollow body and expanding the expandable structure to engage the wall of the first hollow body;

further comprising the steps of:

(d) providing a delivery device adapted to retain the expandable structure in a collapsed condition;

(e) delivering the expandable structure in a collapsed condition through the opening in the wall of the first hollow body; and (f) releasing the expandable structure from the delivery device thereby allowing the expandable structure to expand.

10. The method of claim 9, further comprising the steps of providing a second securing component capable of producing a magnetic field, joining the second securing component to a second hollow body, and magnetically coupling the second securing component to the magnetic port created according to step (c) to form an end-to-side anastomosis between the first and second hollow bodies.

11. The method of claim 9 wherein the delivery device includes a tip component adapted to cut through tissue.

12. A method of coupling a lumen of a first hollow body to a lumen of a second hollow body, the method comprising the steps of:

(a) forming an opening in a wall of the first hollow body, the opening extending into the lumen of the first hollow body;

(b) providing a first coupling component capable of producing a magnetic field and having an opening adapted to be placed in communication with the opening in the wall of the first hollow body;

(c) attaching the first coupling component to the first hollow body by expanding a portion of the first coupling component within the lumen of the first hollow body to engage the wall of the first hollow body;

(d) forming an opening in a wall of a second hollow body, the opening extending into the lumen of the second hollow body;

(e) providing a second coupling component capable of producing a magnetic field and having an opening adapted to be placed in communication with the opening in the wall of the second hollow body;

(f) attaching the second coupling component to the second hollow body by expanding a portion of the second coupling component within the lumen of the second hollow body to engage the wall of the second hollow body;

(g) magnetically coupling the first coupling component to the second coupling component to couple the lumen of the first hollow body to the lumen of the second hollow body;

wherein the first coupling component includes a plurality of arms that are generally coplanar for contacting the wall of the first hollow body when the arms are expanded; and wherein the arms of the first coupling component are self-expanding.

13. A method of coupling a lumen of a first hollow body to a lumen of a second hollow body, the method comprising the steps of:

(a) forming an opening in a wall of the first hollow body, the opening extending into the lumen of the first hollow body;

(b) providing a first coupling component capable of producing a magnetic field and having an opening adapted to be placed in communication with the opening in the wall of the first hollow body;

(c) attaching the first coupling component to the first hollow body by expanding a portion of the first coupling component within the lumen of the first hollow body to engage the wall of the first hollow body;

(d) forming an opening in a wall of a second hollow body, the opening extending into the lumen of the second hollow body;

(e) providing a second coupling component capable of producing a magnetic field and having an opening adapted to be placed in communication with the opening in the wall of the second hollow body;

(f) attaching the second coupling component to the second hollow body by expanding a portion of the second coupling component within the lumen of the second hollow body to engage the wall of the second hollow body;

(g) magnetically coupling the first coupling component to the second coupling component to couple the lumen of the first hollow body to the lumen of the second hollow body;

wherein the first coupling component includes a plurality of arms that are generally coplanar for contacting the wall of the first hollow body when the arms are expanded;

wherein the second coupling component includes a plurality of arms that are generally coplanar for contacting the wall of the second hollow body when the arms are expanded; and wherein the arms of the second coupling component are self-expanding.

* * * * *